(12) United States Patent
Barber

(10) Patent No.: US 12,134,605 B2
(45) Date of Patent: Nov. 5, 2024

(54) SUBSTITUTED 1,2,4-TRIAZOLES AND METHODS OF USE

(71) Applicant: STINGINN LLC, Miami, FL (US)

(72) Inventor: Glen N Barber, Miami, FL (US)

(73) Assignee: StingInn, LLC, Miami, FL (US)

( * ) Notice: Subject to any disclaimer, the term of this patent is extended or adjusted under 35 U.S.C. 154(b) by 873 days.

(21) Appl. No.: 17/127,797

(22) Filed: Dec. 18, 2020

(65) Prior Publication Data

US 2021/0188786 A1    Jun. 24, 2021

Related U.S. Application Data

(63) Continuation-in-part of application No. PCT/US2020/065756, filed on Dec. 17, 2020.

(60) Provisional application No. 63/126,517, filed on Dec. 16, 2020, provisional application No. 62/949,511, filed on Dec. 18, 2019.

(51) Int. Cl.
| | |
|---|---|
| C07D 249/12 | (2006.01) |
| A01N 43/82 | (2006.01) |
| C07D 271/06 | (2006.01) |
| C07D 401/04 | (2006.01) |
| C07D 401/14 | (2006.01) |
| C07D 417/12 | (2006.01) |

(52) U.S. Cl.
CPC ........... *C07D 249/12* (2013.01); *A01N 43/82* (2013.01); *C07D 271/06* (2013.01); *C07D 401/04* (2013.01); *C07D 401/14* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 7,041,301 | B1 | 5/2006 | Markovic |
| 9,045,483 | B2 | 6/2015 | Chen |
| 9,073,941 | B2 | 7/2015 | Wong |
| 10,821,142 | B2 | 11/2020 | Barber |
| 11,629,346 | B2 | 4/2023 | Barber |
| 2002/0156033 | A1 | 10/2002 | Bratzler |
| 2003/0091592 | A1 | 3/2003 | Barber |
| 2003/0114405 | A1 | 6/2003 | Linnik |
| 2004/0024063 | A1 | 2/2004 | Berge |
| 2004/0235770 | A1 | 11/2004 | Davis |
| 2009/0060912 | A1 | 3/2009 | Nuss |
| 2009/0317456 | A1 | 12/2009 | Karrasch |
| 2010/0284921 | A1 | 11/2010 | Gordon |
| 2011/0262485 | A1 | 10/2011 | Barber |
| 2013/0039890 | A1 | 2/2013 | Weichselbaum |
| 2013/0039933 | A1 | 2/2013 | Barber |
| 2013/0079342 | A1 | 3/2013 | Dransfield |
| 2013/0183328 | A1 | 7/2013 | Yu |
| 2014/0296129 | A1 | 10/2014 | Flammer |
| 2015/0011537 | A1 | 1/2015 | Baruch |
| 2015/0087973 | A1 | 3/2015 | Peyman |
| 2015/0368612 | A1 | 12/2015 | Palucka |
| 2016/0067334 | A1 | 3/2016 | Weiner |
| 2016/0331831 | A1 | 11/2016 | Revaud |
| 2017/0037400 | A1 | 2/2017 | Barber |
| 2017/0146519 | A1 | 5/2017 | Defilippis |
| 2019/0284557 | A1 | 9/2019 | Kasperkovitz |
| 2019/0314429 | A1 | 10/2019 | Barber |
| 2020/0392492 | A1 | 12/2020 | Barber |
| 2021/0017541 | A1 | 1/2021 | Barber |
| 2021/0046133 | A1 | 2/2021 | Barber |
| 2021/0188786 | A1 | 6/2021 | Barber |
| 2021/0324023 | A1 | 10/2021 | Barber |
| 2021/0364497 | A1 | 11/2021 | Barber |
| 2022/0184202 | A1 | 6/2022 | Barber |
| 2023/0241092 | A1 | 8/2023 | Barber |
| 2023/0242913 | A1 | 8/2023 | Barber |

FOREIGN PATENT DOCUMENTS

| | | |
|---|---|---|
| EP | 2980099 | 2/2016 |
| EP | 2583974 | 4/2017 |
| EP | 3301179 | 4/2018 |
| WO | WO2002059098 | 8/2002 |
| WO | WO2003048202 | 6/2003 |
| WO | WO2005097758 | 10/2005 |
| WO | WO2008084087 | 7/2008 |
| WO | WO2009066084 | 5/2009 |
| WO | WO2009078587 | 6/2009 |
| WO | WO2010093335 | 8/2010 |
| WO | WO2011127333 | 10/2011 |
| WO | WO2012/154403 | 11/2012 |

(Continued)

OTHER PUBLICATIONS

Tozkoparan et al. (Bioorganic & Medicinal Chemistry 15 (2007) 1808-1814).*
STN registry record: RN 2361800-07-7 (Entered date: Jul. 2, 2019).*
Mukai et al., Activation of STING requires palmitoylation at the Golgi, Nature (2016), 7, pp. 1-10.
Tang et al. "Single amino acid change in STING leads to constitutive active signaling." PloS one. Mar. 19, 2015, vol. 10, No. 3, p. e0120090.

(Continued)

*Primary Examiner* — Bong-Sook Baek
(74) *Attorney, Agent, or Firm* — SCI-LAW STRATEGIES, PC

(57) ABSTRACT

In an embodiment of the present invention, compounds of the present application or pharmaceutically acceptable salts thereof are capable of interacting with and activating the stimulator of interferon genes (STING) protein. In an embodiment of the present invention, pharmaceutical compositions and methods involving such compounds as STING modulators are additionally provided herein.

6 Claims, 16 Drawing Sheets

Specification includes a Sequence Listing.

(56) References Cited

FOREIGN PATENT DOCUMENTS

| WO | WO2013063458 | 5/2013 |
|---|---|---|
| WO | WO2013/166000 | 11/2013 |
| WO | WO2013033688 | 12/2013 |
| WO | WO2013185052 | 12/2013 |
| WO | WO2014/099824 | 6/2014 |
| WO | WO2016057834 | 4/2016 |
| WO | WO2016102431 | 6/2016 |
| WO | WO2016001871 | 11/2016 |
| WO | WO2017007027 | 1/2017 |
| WO | WO2017192856 | 11/2017 |
| WO | WO2018081459 | 5/2018 |
| WO | WO2018231752 | 12/2018 |
| WO | WO2019035901 | 2/2019 |
| WO | WO2019191070 | 10/2019 |
| WO | WO2019195285 | 10/2019 |
| WO | WO2019222290 | 11/2019 |
| WO | WO2022245986 | 11/2022 |
| WO | WO2022271995 | 12/2022 |

OTHER PUBLICATIONS

Unterholzner et al., IFI16 is an innate immune sensor for intracellular DNA, Nature Immunology, (2010) 11, pp. 997-1004.
Weiss et al., The STING agonist DMXAA triggers a cooperation between T lymphocytes and myeloid cells that leads to tumor regression, Oncoimmunology (2017) 6, pp. e1346765 2-11.
Xia et al., Deregulation of STING Signaling in Colorectal Carcinoma Constrains DNA Damage Responses and Correlates With Tumorigenesis. Cell Rep. (2016) 14, pp. 282-297.
Zhang et al., The helicase DDX41 senses intracellular DNA mediated by the adaptor STING in dendritic cells, Nature Immunology, (2011) 12, pp. 959-965.
Zhu et al., Cutting edge: STING mediates protection against colorectal tumorigenesis by governing the magnitude of intestinal inflammation. J Immunol (2014)193, pp. 4779-4782.
Monsurro et al. Anti-viral state segregates two molecular phenotypes of pancreatic adenocarcinoma: potential relevanc adenoviral gene therapy, J. Transl. Med. (2010) 8, 1-11.
PCT International Search Report, PCT/US2018/00169, dated Jan. 28, 2019, 3 pages.
PCT International Search Report, PCT/US2019/025380, dated Jun. 21, 2019, 2 pages.
Barber GN. Innate immune DNA sensing pathways: STING, AIMII and the regulation of interferon production and inflammatory responses. Curr Opin Immunol. (2011) 23, pp. 10-20.
Betancourt et al., Cutting Edge: Innate Immune Augmenting Vesicular Stomatitis Virus Expressing Zika Virus Proteins Confers Protective Immunity. J Immunol. (2017) 198, pp. 3023-3028.

Cai et al., The cGAS-cGAMP-STING pathway of cytosolic DNA sensing and signaling. Mol Cell, (2014) 54, pp. 289-296.

Crinelli et al., Design and characterization of decoy oligonucleotides containing locked nucleic acids. Nucleic Acids Res. (2002) 30 pp. 2435-2443.

Dai et al., Structures of the Zika Virus Envelope Protein and Its Complex with a Flavivirus Broadly Protective Antibody. Cell Host Microbe. (2016) 19, pp. 696-704.

Ishikawa H, Barber GN. The STING pathway and regulation of innate immune signaling in response to DNA pathogens. Cell Mol Life Sci. (2011) 68, pp. 1157-1165.

Jin, Lei et al. "MPYS, a novel membrane tetraspanner, is associated with major histocompatibility complex class II and mediates transduction of apoptotic signals." Molecular and cellular biology, 28 (2008) pp. 5014-5026.

Karayel et al., The TLR-independent DNA recognition pathway in murine macrophages: Ligand features and molecular signature. Eur J Immunol, (2009) 39, pp. 1929-1936.

Kato et al., Structural and functional analyses of DNA-sensing and immune activation by human cGAS. PLoS One, (2013) 8, pp. 1-9.

Onizuka et al., $CO_2$ response for expression of ribulose-1,5-bisphosphate carboxylase/oxygenase genes is inhibited by AT-rich decoy in the cyanobacterium. FEBS Lett., (2003) 542, pp. 42-46.

Ring A, Dowsett M. Mechanisms of tamoxifen resistance. Endocr Relat Cancer. Dec. 2004;11(4):643-58. doi: 10.1677/erc.1.00776. PMID: 15613444.

Renaud et al., Improved Genome Editing Efficiency and Flexibility Using Modified Oligonucleotides with TALEN and CRISPR-Cas9 Nucleases. Cell Rep. (2016) 14, pp. 2263-2272.

Rose et al. "Glycoprotein exchange vectors based on vesicular stomatitis virus allow effective boosting and generation of neutralizing antibodies to a primary isolate of human immunodeficiency virus type 1." J. of virology, 74, (2000) pp. 10903-10910.

Takayuki et al. "STING recognition of cytoplasmic DNA instigates cellular defense." *Molecular cell*, (2013) 50, pp. 5-15.

Xie et al., Design, Synthesis and Biological Evaluation of (2',5' and 3'5'-Linked) cGAMP Analogs that Activate Stimulator of Interferon Genes (STING). Molecules. (2020) 25, 5285-5299.

PubChem SID-382846631, https://pubchem.ncbi.nlm.nih.gov/substance/382846631, last visited Aug. 5, 2020.

Gajewski et al., Immunotherapy with a sting, Science, 369, (2020) 921-922.

Pan et al., An orally available non-nucleotide STING agonist with antitumor activity, Science, 369, (2020) eaba6098.

Chin et al., Antitumor activity of a systemic STING-activating non-nucleotide cGAMP mimetic, Science, 369, (2020) 993-999.

Ahn et al., STING signaling and host defense against microbial infection, Experimental & Molecular Medicine, 51 (2019) 155.

Ge et al., Discovery of Cdc25A Lead Inhibitors with a Novel Chemotype by Virtual Screening: Application of Pharmacophore Modeling Based on a Training Set with a Limited Number of Unique Components, ChemMedChem, 12 (2017) 438-447.

Li et al., Design, synthesis, and biological evaluation of novel alkylsulfany1-1,2,4-triazoles as cis-restricted combretastatin A-4 analogues, Eur. J. Med. Chem., 125 (2016) 1098-1106.

Kim et al., Anticancer Activities of Cdc25 Phosphatase Inhibitors in the Proliferation of Human Lung Cancer Cells, Bull. Korean Chem. Soc. 35 (2014) 319-321.

Abdul-Aziz et al., New nitric oxide donating 1,2,4-triazole/oxime hybrids: Synthesis, investigation of anti-inflammatory, ulceroginic liability and antiproliferative activities, Bioorg. & Med. Chem., 21 (2013) 3839-3849.

Park et al., Structure-based de 1-8, novo design and biochemical evaluation of 10-15 novel Cdc25 phosphatase inhibitors, Bioorg. & Med. Chem. Lett, 19 (2019) 4330-4334.

Muhi-Eldeen et al., Synthesis and antimicrobial evaluation of tert-amino-2-butynyl)thio and alkyl/alkenylthio-4,5-disubstituted-4H-1,2,4-triazoles, Eur. J. Med. Chem., 26 (1991) 237-241.

Shahzad et al., Identification of 1,2,4-triazoles as new thymidine phosphorylase inhibitors: Future anti-tumor drugs, Bioorg. Chem., 85 (2019) 209-220.

PCT International Search Report, PCT/US2010/017248, dated Feb. 23, 2010, 3 pages.

PCT International Search Report, PCT/US2013/038840, dated Sep. 5, 2013, 1 pages.

PCT International Search Report, PCT/US2016/037288, dated Nov. 30, 2016, 4 pages.

PCT International Search Report, PCT/US2017/031067, dated Jul. 28, 2017, 2 pages.

PCT International Search Report, PCT/US2018/036997, dated Sep. 12, 2018, 10 pages.

PCT International Search Report, PCT/US2020/065756, dated Sep. 9, 2020, 4 pages.

Extended European Search Report for 18817870 from PCT/US2018/036997, Feb. 8, 2021, 13 pages.

PCT International Search Report, PCT/US2022/034796, dated Nov. 29, 2022, 19 pages.

Extended European Search Report for 20903425.5 from PCT/US2020/065756 (EP4075980), Sep. 12, 2023, 20 pages.

Buijs et al., Oncolytic viruses: From bench to bedside with a focus on safety. Hum Vaccin Immunotherapeut, (2015) 11, pp. 1573-1584.

(56) References Cited

OTHER PUBLICATIONS

Corrales et. al. Direct Activation of STING in the Tumor Microenvironment Leads to Potent and Systemic Tumor Regression and Immunity. Cell Rep. (2015) 11, pp. 1018-1030.

Dai et al., MVV Ankara triggers type I IFN production in murine conventional dendritic cells via a cGAS/STING-mediated cytosolic DNA-sensing pathway. PLoS (2014) 10 e1003989.

Deimling T. "Recognition of cytosolic nucleotides by the innate immune system", Doctoral dissertation, Imu. Aug. 14, 2014.

Holm et. al. Influenza A virus targets a cGAS-independent STING pathway that controls enveloped RNA viruses. Nat Commun. (2016) 7, 10680.

Ishikawa et al., STING regulates intracellular DNA-mediated, type I interferon-dependent innate immunity, Nature, (2009) 461, pp. 788-792.

Konno et al., Pro-inflammation Associated with a Gain-of-Function Mutation (R284S) in the Innate Immune Sensor STING, Cell (20180) 23, pp. 1112-1123.

Li et al., Regulating STING in health and disease. J Inflamm (2017)14, pp. 12950-12971.

Liu et al., Activated STING in a Vascular and Pulmonary Syndrome, New England Journal of Medicine, (2014) 371, pp. 507-518.

Ma et al., The cGAS-STING Defense Pathway and Its Counteraction by Viruses. Cell Host Microbe (2016) 19, pp. 150-158.

PCT International Search Report, PCT/US2019/024039, dated Jul. 2, 2019, 5 pages.

PCT International Search Report, PCT/US2020/027649, dated Sep. 9, 2020, 3 pages.

\* cited by examiner

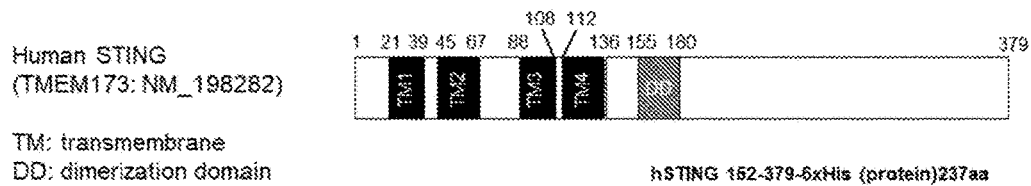
FIG. 8A
FIG. 9
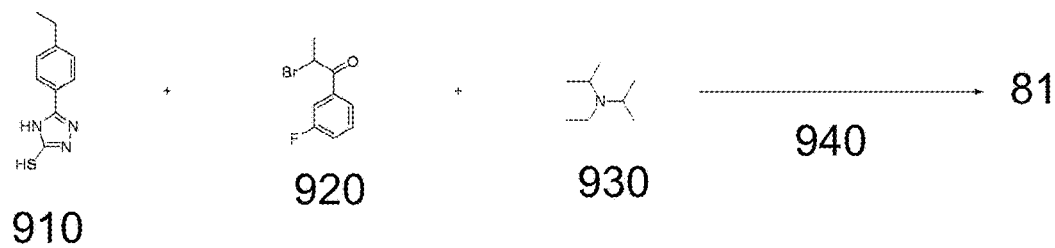
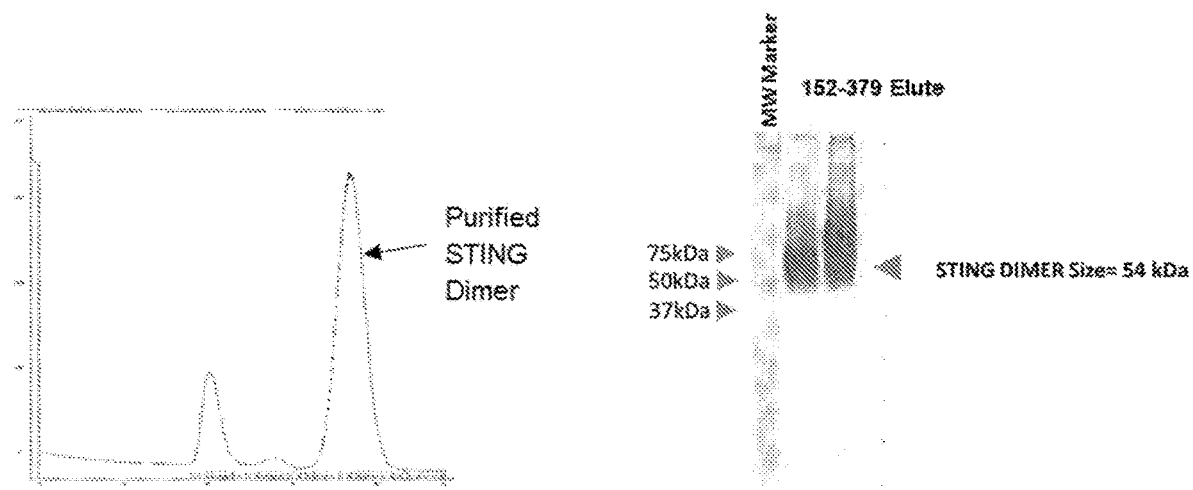
FIG. 8B

SEQUENCE LISTING

<160> NUMBER OF SEQ ID NOS: 1

<210> SEQ ID NO 1
<211> LENGTH: 237
<212> TYPE: PRT
<213> ORGANISM: Artificial Sequence
<220> FEATURE:
<223> OTHER INFORMATION: Synthetic polypeptide

<400> SEQUENCE: 1

```
Met Asn Phe Asn Val Ala His Gly Leu Ala Trp Ser Tyr Tyr Ile Gly
1               5                   10                  15

Tyr Leu Arg Leu Ile Leu Pro Glu Leu Gln Ala Arg Ile Arg Thr Tyr
                20                  25                  30

Asn Gln His Tyr Asn Asn Leu Leu Arg Gly Ala Val Ser Gln Arg Leu
            35                  40                  45

Tyr Ile Leu Leu Pro Leu Asp Cys Gly Val Pro Asp Asn Leu Ser Met
        50                  55                  60

Ala Asp Pro Asn Ile Arg Phe Leu Asp Lys Leu Pro Gln Gln Thr Gly
65                  70                  75                  80

Asp His Ala Gly Ile Lys Asp Arg Val Tyr Ser Asn Ser Ile Tyr Glu
                85                  90                  95

Leu Leu Glu Asn Gly Gln Arg Ala Gly Thr Cys Val Leu Glu Tyr Ala
            100                 105                 110

Thr Pro Leu Gln Thr Leu Phe Ala Met Ser Gln Tyr Ser Gln Ala Gly
        115                 120                 125

Phe Ser Arg Glu Asp Arg Leu Glu Gln Ala Lys Leu Phe Cys Arg Thr
130                 135                 140

Leu Glu Asp Ile Leu Ala Asp Ala Pro Glu Ser Gln Asn Asn Cys Arg
145                 150                 155                 160

Leu Ile Ala Tyr Gln Glu Pro Ala Asp Asp Ser Ser Phe Ser Leu Ser
                165                 170                 175

Gln Glu Val Leu Arg His Leu Arg Gln Glu Glu Lys Glu Glu Val Thr
            180                 185                 190

Val Gly Ser Leu Lys Thr Ser Ala Val Pro Ser Thr Ser Thr Met Ser
        195                 200                 205

Gln Glu Pro Glu Leu Leu Ile Ser Gly Met Glu Lys Pro Leu Pro Leu
    210                 215                 220

Arg Thr Asp Phe Ser Leu Glu His His His His His His
225                 230                 235
```

SUBSTITUTED 1,2,4-TRIAZOLES AND METHODS OF USE

PRIORITY CLAIM

This application is a continuation in part of (i) Patent Cooperation Treaty Application PCT/US20/65756, filed Dec. 17, 2020, which claims the priority benefit of (ii) U.S. Provisional Patent Application No. 62/949,511, filed Dec. 18, 2019 and (iii) U.S. Provisional Patent Application No. 63/126,517, filed Dec. 16, 2020; each of (i)-(iii) are herein incorporated by reference in their entireties and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file STNG-01005US2_ST25.TXT, created Dec. 18, 2020, 2,488 bytes, machine format IBM-PC, MS-Windows operating system, is hereby incorporated by reference.

BACKGROUND

Cellular innate immune sensors, such as STING, have evolved to detect microbial infection of the cell. STimulator of Interferon Genes (STING) is activated by cyclic dinucleotides (CDN's) such as cyclic di-GMP and cyclic-di-AMP secreted by intracellular bacteria following infection. Alternatively, STING can be activated by cyclic GMP-AMP (cGAMP) generated by a cellular cGAMP synthase cGAS (MB21D1) after association with aberrant cytosolic dsDNA species, which can include microbial DNA or self-DNA leaked from the nucleus. Association with CDN's enables STING to activate the transcription factors IRF3 and NF-κB which stimulate the production of type I interferon (IFN) and pro-inflammatory cytokines, which facilitate adaptive immunity. Aside from being critical for the protection against microbial infection, STING signaling has been shown to be important for facilitating anti-tumor T cell activity. Regulation of the immune system to facilitate robust anti-tumor cytotoxic T cell responses is proving to be a powerful approach for the effective treatment of a variety of cancers.

SUMMARY

In one aspect, the present application relates to a compound of Formula I:

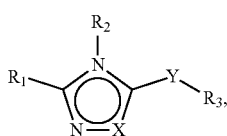

(I)

or a pharmaceutically acceptable salt or ester thereof, where X, Y, $R_1$, $R_2$, and $R_3$ are each defined herein.

In another aspect, the present application relates to a pharmaceutical composition including a therapeutically effective amount of a compound of the application, or a pharmaceutically acceptable salt or ester thereof, and a pharmaceutically acceptable carrier. In an embodiment of the present invention, a method of treating or preventing a disease includes stimulating a STING protein. The method comprises administering to a subject in need thereof an effective amount of a compound of the application or a pharmaceutically acceptable salt or ester thereof, or a pharmaceutical composition of the application. In one embodiment, the STING protein is a human STING protein.

In another embodiment of the invention, a method involves treating or preventing a disease, where the diseases is caused by, or associated with, STING expression, activity, and/or function (e.g., deregulation of STING expression, activity, and/or function). The method comprises administering to a subject in need thereof an effective amount of a compound of the application or a pharmaceutically acceptable salt or ester thereof, or a pharmaceutical composition of the application.

In a different embodiment of the invention, a method of treating or preventing a disease includes deregulation of one or more of the intracellular pathways in which a STING protein is involved (e.g., deregulation of intracellular dsDNA mediated type I interferon activation). The method comprises administering to a subject in need thereof an effective amount of a compound of the application or a pharmaceutically acceptable salt or ester thereof, or a pharmaceutical composition of the application.

In an embodiment of the invention, a kit including a compound of the application or a pharmaceutically acceptable salt or ester thereof, or a pharmaceutical composition of the application is supplied together with instructions for the use thereof for reducing metastasis and neoplastic growth in a mammal.

In another embodiment of the invention, a compound as described in Table II of the application or a pharmaceutically acceptable salt or ester thereof, or a pharmaceutical composition of the application, is used in the manufacture of a medicament for stimulating a STING protein, for treating or preventing a disease, where the diseases is caused by, or associated with, STING expression, activity, and/or function (e.g., deregulation of STING expression, activity, and/or function), or for treating or preventing a disease associated with deregulation of one or more of the intracellular pathways in which a STING protein is involved (e.g., deregulation of intracellular dsDNA mediated type I interferon activation).

In a different embodiment of the invention, a compound of the application or a pharmaceutically acceptable salt or ester thereof, or a pharmaceutical composition of the application, is used in the manufacture of a medicament for stimulating a STING protein, for treating or preventing a disease, where the diseases is caused by, or associated with, STING expression, activity, and/or function (e.g., deregulation of STING expression, activity, and/or function), or for treating or preventing a disease associated with deregulation of one or more of the intracellular pathways in which a STING protein is involved (e.g., deregulation of intracellular dsDNA mediated type I interferon activation).

In another different embodiment of the invention, a compound as described in Table II or a pharmaceutically acceptable salt or ester thereof, or a pharmaceutical composition of the application, is used in stimulating a STING protein, in treating or preventing a disease, where the diseases is caused by, or associated with, STING expression, activity, and/or function (e.g., deregulation of STING expression, activity, and/or function), or in treating or preventing a disease associated with deregulation of one or more of the intracellular pathways in which a STING protein is involved (e.g., deregulation of intracellular dsDNA mediated type I interferon activation).

In an embodiment of the invention, a compound of the application or a pharmaceutically acceptable salt or ester thereof, or a pharmaceutical composition of the application is used, in stimulating a STING protein, in treating or preventing a disease, where the diseases is caused by, or associated with, STING expression, activity, and/or function (e.g., deregulation of STING expression, activity, and/or function), or in treating or preventing a disease associated with deregulation of one or more of the intracellular pathways in which a STING protein is involved (e.g., deregulation of intracellular dsDNA mediated type-1 interferon activation).

The present application provides modulators of a STING protein that are therapeutic agents in the treatment or prevention of diseases such as cancer and immunological disorders. The details of the disclosure are set forth in the accompanying description below. Although methods and materials similar or equivalent to those described herein can be used in the practice or testing of the present application, illustrative methods and materials are now described. In the case of conflict, the present specification, including definitions, will control. In addition, the materials, methods, and examples are illustrative only and are not intended to be limiting. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

The contents of all references (including literature references, issued patents, published patent applications, and co-pending patent applications) cited throughout this application are hereby expressly incorporated herein in their entireties by reference. The references cited herein are not admitted to be prior art to the application.

BRIEF DESCRIPTION OF THE DRAWINGS

Various embodiments of the present invention will be described in detail based on the following Figures, where:

FIG. 8A shows a human STING protein structure. C-terminal portion from AA 152-379 (237aa long) was cloned into the pET26B vector NdeI-XhoI sites (STING152-379H);

FIG. 8B shows STING152-379H that was purified over a nickel column as described in materials and methods;

FIG. 9 shows a schematic illustrating the synthesis of Compound 81;

DETAILED DESCRIPTION

Figure 1F:
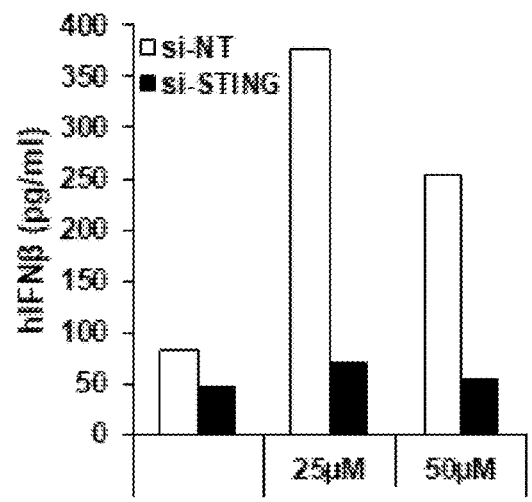
FIG. 1F shows that Compound 28 is STING specific and Compound 28 does not induce type I IFN production in the absence of STING (STING expression was suppressed in hTERT cells using sRNAi prior to the addition of Compound 28)

The present application relates to compounds of Formula I that are shown to potently and selectively modulate a STING protein (e.g., the human STING protein). In one embodiment, a compound of the present application is represented by Formula I:

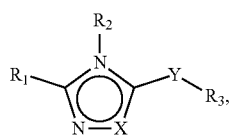

(I)

or a pharmaceutically acceptable salt, hydrate, solvate, prodrug, stereoisomer, or tautomer thereof, where $R_1$ is $(C_1-C_6)$ alkyl, $(C_3-C_6)$ cycloalkyl, $(C_5-C_{10})$ aryl, or 5-to 14-membered heterocyclyl including 1-5 heteroatoms selected from N, O and S, where the alkyl, cycloalkyl, aryl or heterocyclyl is optionally substituted with one or more $R_{1a}$; each $R_{1a}$ is independently $(C_1-C_6)$ alkyl, $(C_3-C_6)$ cycloalkyl, $(C_1-C_6)$ haloalkyl, $(C_1-C_6)$ alkoxy, $(C_1-C_6)$ haloalkoxy, $(C_2-C_6)$ alkenyl, $(C_2-C_6)$ alkynyl, halogen, nitro, CN, oxo, $B(OH)_2$, OH, COOH, SH, $NH_2$, $NH(C_1-C_4)$ alkyl, or $N((C_1-C_4)$ alkyl$)_2$; $R_2$ is H, $(C_1-C_4)$ alkyl, $SO_2$—$(C_1-C_{12})$-alkyl, or $(C_5-C_{10})$ aryl, where the alkyl or aryl is optionally substituted by OH, alkoxy, or halogen; X is —N— or —O—, provided when X is —O—, then $R_2$ is absent; Y is a direct bond, —$NR_{xa}$—, —O—, or —S—; where $R_{xa}$ is H, $(C_1-C_6)$ alkyl, $(C_3-C_6)$ cycloalkyl, $(C_5-C_{10})$ aryl, or 5-to 14-membered heterocyclyl including 1-5 heteroatoms selected from N, O and S; $R_3$ is $(C_3-C_6)$ cycloalkyl or $(C_1-C_6)$ alkyl, where the cycloalkyl is optionally substituted with one or more halogen, —$OR_4$, oxo, —$NHS(O)_2R_4$, or $R_4$; where each $R_4$ is independently H, $(C_5-C_{10})$ aryl, $(C_5-C_{10})$ cycloalkyl, $(C_5-C_{10})$ heteroaryl, or 5-to 14-membered heterocyclyl including 1-5 heteroatoms selected from N, O and S, where the aryl, heteroaryl, or heterocyclyl is optionally substituted with one or more $(C_5-C_{10})$ aryl, $(C_1-C_6)$ alkyl, $(C_3-C_6)$ cycloalkyl, $(C_1-C_6)$ haloalkyl, $(C_1-C_6)$ alkoxy, $(C_1-C_6)$ haloalkoxy, $(C_2-C_6)$ alkenyl, $(C_2-C_6)$ alkynyl, halogen, nitro, —CN, oxo, —$B(OH)_2$, —OH, —COOH, —SH, —$NH_2$, —$NH(C_1-C_4)$ alkyl, —$N((C_1-C_4)$ alkyl$)_2$, —NH—$SO_2$—$(C_1-C_{12})$-alkyl, or —$(CH_2)_nNC(O)(C_1-C_4)$ alkyl groups, where n is 0, 1, 2, or 3.

The compound of Formula (I) is a compound of Formula (Ia),

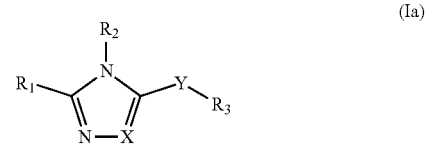

(Ia)

or a pharmaceutically acceptable salt, hydrate, solvate, prodrug, stereoisomer, or tautomer thereof.

The compound of Formula (I) is a compound of Formula (Ib),

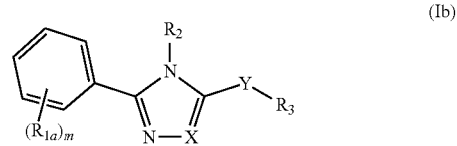

(Ib)

or a pharmaceutically acceptable salt, hydrate, solvate, prodrug, stereoisomer, or tautomer thereof, where m is 0, 1, 2, 3, 4 or 5.

The compound of Formula (I) is a compound of Formula (Ic),

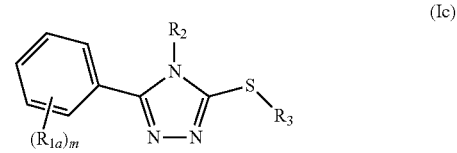

(Ic)

or a pharmaceutically acceptable salt, hydrate, solvate, prodrug, stereoisomer, or tautomer thereof.

The compound of Formula (I) is a compound of Formula (Id),

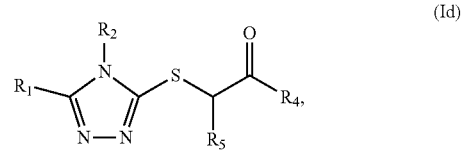

(Id)

or a pharmaceutically acceptable salt, hydrate, solvate, prodrug, stereoisomer, or tautomer thereof, where $R_5$ is H, $(C_1-C_6)$ alkyl, $(C_5-C_{10})$ aryl, where the alkyl, or aryl is optionally substituted with $(C_5-C_{10})$ aryl, $(C_1-C_6)$ alkyl, $(C_1-C_6)$ alkoxy, $(C_3-C_6)$ cycloalkyl, $(C_1-C_6)$ haloalkyl, $(C_1-C_6)$ alkoxy, halogen, or oxo.

The compound of Formula (I) is a compound of Formula (Ie),

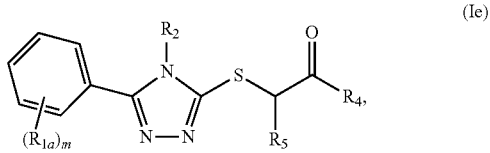

or a pharmaceutically acceptable salt, hydrate, solvate, prodrug, stereoisomer, or tautomer thereof, where $R_5$ is H, $(C_1-C_6)$ alkyl, $(C_5-C_{10})$ aryl, where the alkyl, or aryl is optionally substituted with $(C_5-C_{10})$ aryl, $(C_1-C_6)$ alkyl, $(C_3-C_6)$ cycloalkyl, $(C_1-C_6)$ haloalkyl, $(C_1-C_6)$ alkoxy, halogen, or oxo, and m is 0, 1, 2, 3, 4 or 5.

The compound of Formula (I) is a compound of Formula (If),

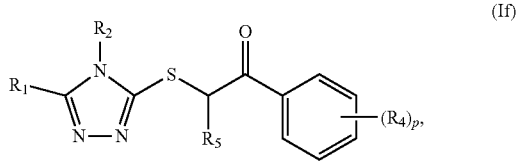

or a pharmaceutically acceptable salt, hydrate, solvate, prodrug, stereoisomer, or tautomer thereof, where p is 0, 1, 2, 3, 4, or 5.

The compound of Formula (I) is a compound of Formula (Ig),

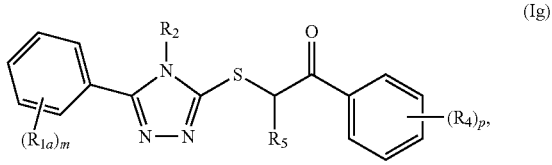

or a pharmaceutically acceptable salt, hydrate, solvate, prodrug, stereoisomer, or tautomer thereof where p is 0, 1, 2, 3, 4, or 5.

In an embodiment of the present invention, $R_1$ is $(C_1-C_6)$ alkyl, $(C_3-C_6)$ cycloalkyl, $(C_5-C_{10})$ aryl, or 5-to 14-membered heterocyclyl including 1-5 heteroatoms selected from N, O and S, where the alkyl, cycloalkyl, aryl or heterocyclyl is optionally substituted with one or more Ria.

In an embodiment of the present invention, $R_1$ is $(C_1-C_6)$ alkyl, $(C_5-C_{10})$ aryl, or 5-to 14-membered heterocyclyl including 1-5 heteroatoms selected from N, O and S, where the alkyl, aryl or heterocyclyl is optionally substituted with one or more $R_{1a}$.

In an embodiment of the present invention, $R_1$ is $(C_1-C_6)$ alkyl, $(C_5-C_{10})$ aryl, or 5-to 14-membered heterocyclyl including 1-5 heteroatoms selected from N, O and S, where the alkyl, cycloalkyl, aryl or heterocyclyl is optionally substituted with one or more $R_{1a}$.

In an embodiment of the present invention, $R_1$ is $(C_1-C_6)$ alkyl optionally substituted with one or more $R_{1a}$.

In an embodiment of the present invention, $R_1$ is $(C_1-C_6)$ alkyl. In an embodiment, $R_1$ is methyl. In an embodiment, $R_1$ is ethyl. In an embodiment, $R_1$ is propyl. In an embodiment, $R_1$ is butyl. In an embodiment, $R_1$ is pentyl. In an embodiment, $R_1$ is hexyl. In an embodiment, $R_1$ is isopropyl. In an embodiment, $R_1$ is isobutyl. In an embodiment, $R_1$ is isopentyl. In an embodiment, $R_1$ is isohexyl. In an embodiment, $R_1$ is sec-butyl. In an embodiment, $R_1$ is secpentyl. In an embodiment, $R_1$ is sec-hexyl. In an embodiment, $R_1$ is tert-butyl.

In an embodiment of the present invention, $R_1$ is $(C_5-C_{10})$ aryl optionally substituted with one or more $R_{1a}$.

In an embodiment of the present invention, $R_1$ is $(C_5-C_{10})$ aryl substituted with one $R_{1a}$. In an embodiment, $R_1$ is $(C_5-C_{10})$ aryl substituted with two $R_{1a}$. In an embodiment, $R_1$ is $(C_5-C_{10})$ aryl substituted with three $R_{1a}$. In an embodiment, $R_1$ is $(C_5-C_{10})$ aryl substituted with four $R_{1a}$. In an embodiment, $R_1$ is $(C_5-C_{10})$ aryl substituted with five $R_{1a}$.

In an embodiment, $R_1$ is 5-to 14-membered heterocyclyl including 1-5 heteroatoms selected from N, O and S, where the alkyl optionally substituted with one or more $R_{1a}$.

In an embodiment of the present invention, $R_1$ is

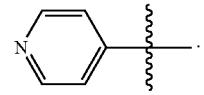

In an embodiment of the present invention, $R_1$ is $(C_1-C_6)$ alkyl, $(C_3-C_6)$ cycloalkyl, $(C_5-C_{10})$ aryl, or 5-to 14-membered heterocyclyl including 1-5 heteroatoms selected from N, O and S, where the alkyl, cycloalkyl, aryl or heterocyclyl is substituted with one or more $R_{1a}$.

In an embodiment of the present invention, $R_1$ is $(C_1-C_6)$ alkyl, $(C_3-C_6)$ cycloalkyl, $(C_5-C_{10})$ aryl, or 5-to 14-membered heterocyclyl including 1-5 heteroatoms selected from N, O and S, where the alkyl, cycloalkyl, aryl or heterocyclyl is substituted with one $R_{1a}$.

In an embodiment of the present invention, $R_1$ is $(C_1-C_6)$ alkyl, $(C_3-C_6)$ cycloalkyl, $(C_5-C_{10})$ aryl, or 5-to 14-membered heterocyclyl including 1-5 heteroatoms selected from N, O and S, where the alkyl, cycloalkyl, aryl or heterocyclyl is substituted with two $R_{1a}$.

In an embodiment of the present invention, $R_1$ is $(C_1-C_6)$ alkyl, $(C_3-C_6)$ cycloalkyl, $(C_5-C_{10})$ aryl, or 5-to 14-membered heterocyclyl including 1-5 heteroatoms selected from N, O and S, where the alkyl, cycloalkyl, aryl or heterocyclyl is substituted with three $R_{1a}$.

In an embodiment of the present invention, $R_1$ is $(C_1-C_6)$ alkyl, $(C_3-C_6)$ cycloalkyl, $(C_5-C_{10})$ aryl, or 5-to 14-membered heterocyclyl including 1-5 heteroatoms selected from N, O and S, where the alkyl, cycloalkyl, aryl or heterocyclyl is substituted with four $R_a$.

In an embodiment of the present invention, $R_1$ is

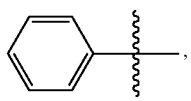 , 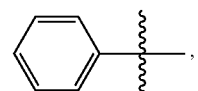 ,

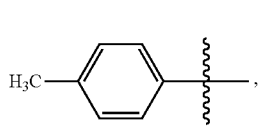 , 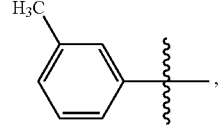 ,

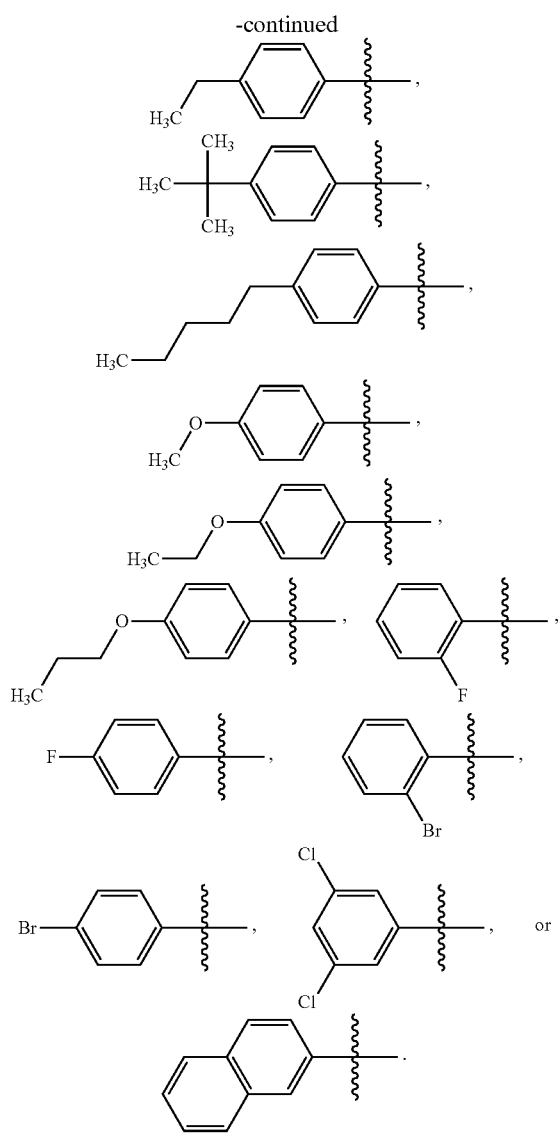

In an embodiment of the present invention, each $R_{1a}$ is independently ($C_1$-$C_6$) alkyl, ($C_3$-$C_6$) cycloalkyl, ($C_1$-$C_6$) haloalkyl, ($C_1$-$C_6$) alkoxy, ($C_1$-$C_6$) haloalkoxy, ($C_2$-$C_6$) alkenyl, ($C_2$-$C_6$) alkynyl, halogen, nitro, CN, oxo, $B(OH)_2$, OH, COOH, SH, $NH_2$, $NH(C_1$-$C_4)$ alkyl, or $N((C_1$-$C_4)$ alkyl$)_2$.

In an embodiment of the present invention, each $R_{1a}$ is independently ($C_1$-$C_6$) alkyl, ($C_1$-$C_6$) alkoxy, or halogen.

In an embodiment of the present invention, each $R_{1a}$ is independently ($C_3$-$C_6$) cycloalkyl, ($C_1$-$C_6$) haloalkyl, ($C_1$-$C_6$) haloalkoxy, ($C_2$-$C_6$) alkenyl, ($C_2$-$C_6$) alkynyl, nitro, CN, oxo, $B(OH)_2$, OH, COOH, SH, $NH_2$, $NH(C_1$-$C_4)$ alkyl, or $N((C_1$-$C_4)$ alkyl$)_2$.

In an embodiment of the present invention, each $R_{1a}$ is independently ($C_1$-$C_6$) alkyl. In an embodiment, $R_{1a}$ is methyl. In an embodiment, $R_{1a}$ is ethyl. In an embodiment, $R_{1a}$ is propyl. In an embodiment, $R_{1a}$ is butyl. In an embodiment, $R_{1a}$ is pentyl. In an embodiment, $R_{1a}$ is hexyl. In an embodiment, $R_{1a}$ is isopropyl. In an embodiment, $R_{1a}$ is isobutyl. In an embodiment, $R_{1a}$ is isopentyl. In an embodiment, $R_{1a}$ is isohexyl. In an embodiment, $R_{1a}$ is secbutyl. In an embodiment, $R_{1a}$ is secpentyl. In an embodiment, $R_{1a}$ is sechexyl. In an embodiment, $R_{1a}$ is tertbutyl.

In an embodiment of the present invention, each $R_{1a}$ is independently ($C_1$-$C_6$) alkoxy.

In an embodiment of the present invention, each $R_{1a}$ is independently halogen. In an embodiment, each $R_{1a}$ is independently F, Cl, Br, or I. In an embodiment, each $R_{1a}$ is independently F, Cl, or Br. In an embodiment, each $R_{1a}$ is independently F. In an embodiment, each $R_{1a}$ is independently Cl. In an embodiment, each $R_{1a}$ is independently Br.

In an embodiment of the present invention, $R_{1a}$ is

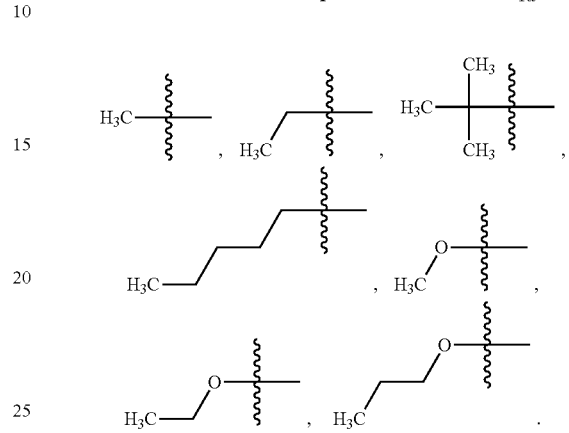

In an embodiment of the present invention, $R_2$ is H, ($C_1$-$C_4$) alkyl, or ($C_5$-$C_{10}$) aryl, where the alkyl or aryl is optionally substituted by OH, alkoxy, or halogen.

In an embodiment of the present invention, $R_2$ is ($C_1$-$C_4$) alkyl, or ($C_5$-$C_{10}$) aryl, where the alkyl or aryl is optionally substituted by OH, alkoxy, or halogen.

In an embodiment of the present invention, $R_2$ is H.

In an embodiment of the present invention, $R_2$ is ($C_1$-$C_4$) alkyl optionally substituted by OH, alkoxy, or halogen.

In an embodiment of the present invention, $R_2$ is ($C_1$-$C_4$) alkyl.

In an embodiment of the present invention, $R_2$ is ($C_5$-$C_{10}$) aryl optionally substituted by OH, alkoxy, or halogen.

In an embodiment of the present invention, $R_2$ is ($C_5$-$C_{10}$) aryl.

In an embodiment of the present invention, $R_2$ is H.

In an embodiment of the present invention, $R_2$ is $CH_3$.

In an embodiment of the present invention, $R_2$ is

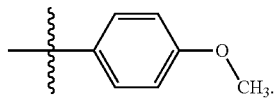

In an embodiment of the present invention, X is —N— or —O—, provided when X is —O—, $R_2$ is absent.

In an embodiment of the present invention, X is —N—.

In an embodiment of the present invention, X is —O— and $R_2$ is absent.

In an embodiment of the present invention, Y is —$NR_{xa}$—, —O—, or —S—. In an embodiment, Y is —$NR_{xa}$— or —O—. In an embodiment, Y is —$NR_{xa}$— or —S—. In an embodiment, Y is —O— or —S—. In an embodiment, Y is —$NR_{xa}$—. In an embodiment, Y is —O—. In an embodiment, Y is —S—.

In an embodiment of the present invention, $R_{xa}$ is H, ($C_1$-$C_6$) alkyl, ($C_3$-$C_6$) cycloalkyl, ($C_5$-$C_{10}$) aryl, or 5-to 14-membered heterocyclyl including 1-5 heteroatoms selected from N, O and S.

In an embodiment of the present invention, $R_{xa}$ is $(C_1-C_6)$ alkyl, $(C_3-C_6)$ cycloalkyl, $(C_5-C_{10})$ aryl, or 5-to 14-membered heterocyclyl including 1-5 heteroatoms selected from N, O and S.

In an embodiment of the present invention, $R_{xa}$ is H.

In an embodiment of the present invention, $R_{xa}$ is $(C_1-C_6)$ alkyl.

In an embodiment of the present invention, $R_{xa}$ is $(C_3-C_6)$ cycloalkyl.

In an embodiment of the present invention, $R_{xa}$ is 5-to 14-membered heterocyclyl including 1-5 heteroatoms selected from N, O and S.

In an embodiment of the present invention, $R_3$ is $(C_3-C_6)$ cycloalkyl or $(C_1-C_6)$ alkyl, where the cycloalkyl or alkyl is optionally substituted with one or more halogen, —$OR_4$, oxo, —$NHS(O)_2R_4$, or $R_4$.

In an embodiment of the present invention, $R_3$ is $(C_3-C_6)$ cycloalkyl optionally substituted with one or more halogen, —$OR_4$, oxo, —$NHS(O)_2R_4$, or $R_4$.

In an embodiment of the present invention, $R_3$ is $(C_3-C_6)$ cycloalkyl optionally substituted with one or more oxo.

In an embodiment of the present invention, $R_3$ is $(C_3-C_6)$ cycloalkyl substituted with one or more oxo. In an embodiment of the present invention, $R_3$ is $(C_3-C_6)$ cycloalkyl substituted with one oxo. In an embodiment of the present invention, $R_3$ is $(C_3-C_6)$ cycloalkyl substituted with two oxo.

In an embodiment of the present invention, $R_3$ is

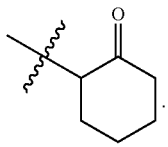 [SMILES: *C1CCCCC1=O]

In an embodiment of the present invention, $R_3$ is $(C_1-C_6)$ alkyl optionally substituted with one or more halogen, —$OR_4$, oxo, —$NHS(O)_2R_4$, or $R_4$. In an embodiment, $R_3$ is $(C_1-C_6)$ alkyl substituted with one halogen, —$OR_4$, oxo, —$NHS(O)_2R_4$, or $R_4$. In an embodiment, $R_3$ is $(C_1-C_6)$ alkyl substituted with two halogen, —$OR_4$, oxo, —$NHS(O)_2R_4$, or $R_4$. In an embodiment, $R_3$ is $(C_1-C_6)$ alkyl substituted with three halogen, —$OR_4$, oxo, —$NHS(O)_2R_4$, or $R_4$. In an embodiment, $R_3$ is $(C_1-C_6)$ alkyl substituted with four halogen, —$OR_4$, oxo, —$NHS(O)_2R_4$, or $R_4$. In an embodiment, $R_3$ is $(C_1-C_6)$ alkyl substituted with five halogen, —$OR_4$, oxo, —$NHS(O)_2R_4$, or $R_4$. In an embodiment, $R_3$ is $(C_1-C_6)$ alkyl substituted with six halogen, —$OR_4$, oxo, —$NHS(O)_2R_4$, or $R_4$. In an embodiment, $R_3$ is $C_1$ alkyl substituted with one or more halogen, —$OR_4$, oxo, —$NHS(O)_2R_4$, or $R_4$. In an embodiment, $R_3$ is $C_2$ alkyl substituted with one or more halogen, —$OR_4$, oxo, —$NHS(O)_2R_4$, or $R_4$. In an embodiment, $R_3$ is $C_3$ alkyl substituted with one or more halogen, —$OR_4$, oxo, —$NHS(O)_2R_4$, or $R_4$. In an embodiment, $R_3$ is $C_4$ alkyl substituted with one or more halogen, —$OR_4$, oxo, —$NHS(O)_2R_4$, or $R_4$. In an embodiment, $R_3$ is $C_5$ alkyl substituted with one or more halogen, —$OR_4$, oxo, —$NHS(O)_2R_4$, or $R_4$. In an embodiment, $R_3$ is $C_6$ alkyl substituted with one or more halogen, —$OR_4$, oxo, —$NHS(O)_2R_4$, or $R_4$.

In an embodiment of the present invention, $R_3$ is $C_2$ alkyl substituted with —$NHS(O)_2R_4$.

In an embodiment of the present invention, $R_3$ is

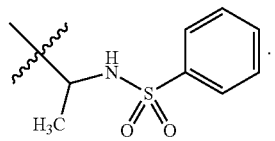 [SMILES: *C(C)NS(=O)(=O)c1ccccc1]

In an embodiment of the present invention, $R_3$ is $C_2$ alkyl substituted with —$OR_4$.

In an embodiment of the present invention, $R_3$ is

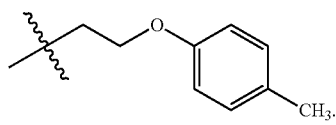 [SMILES: *CCOc1ccc(C)cc1]

In an embodiment of the present invention, $R_3$ is

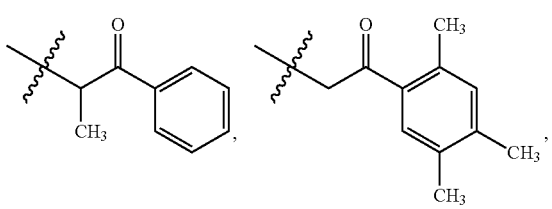

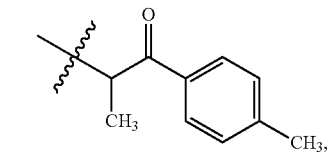

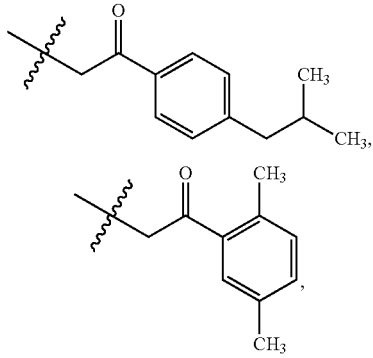

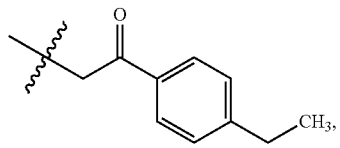

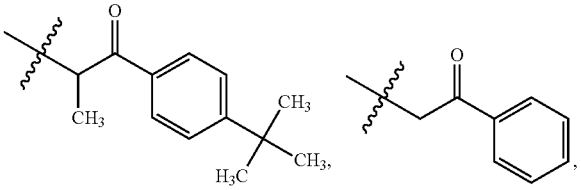

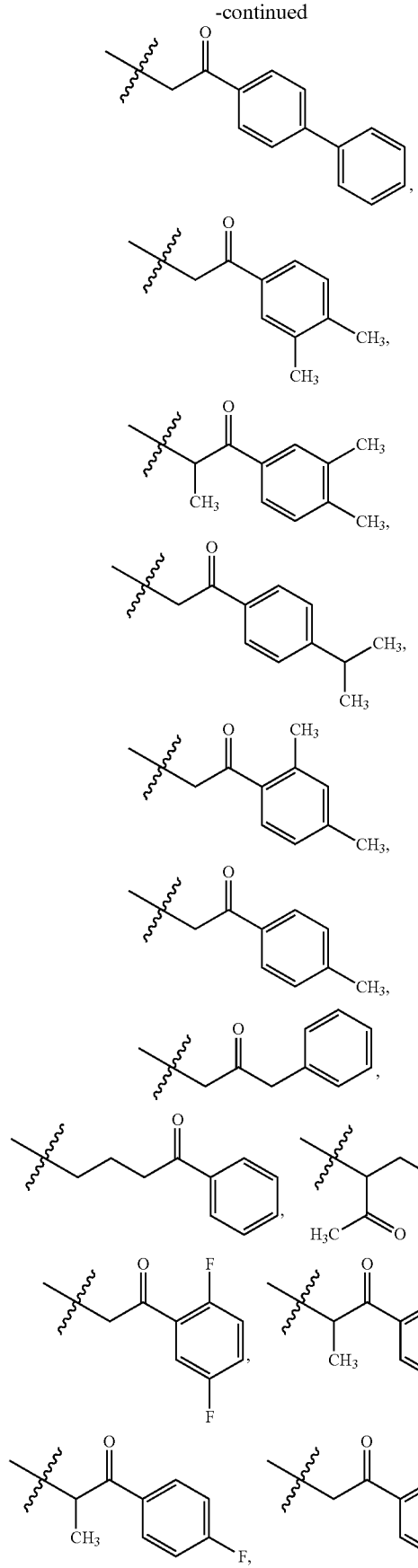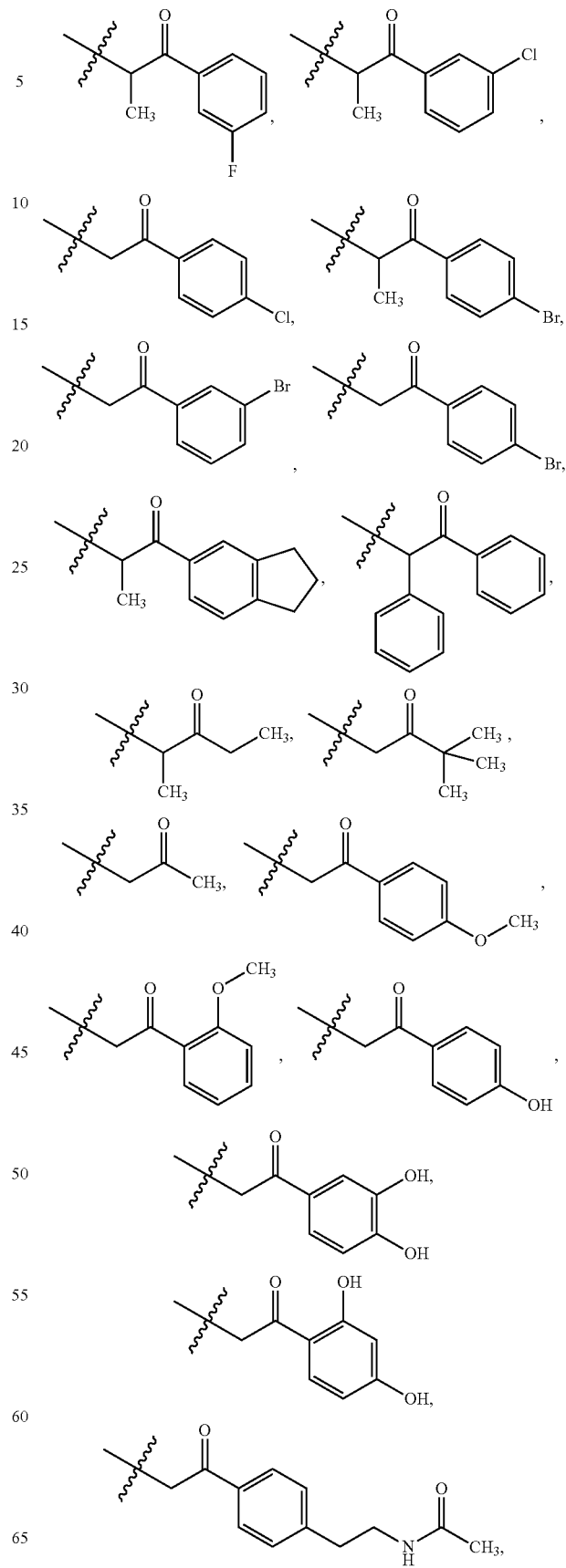

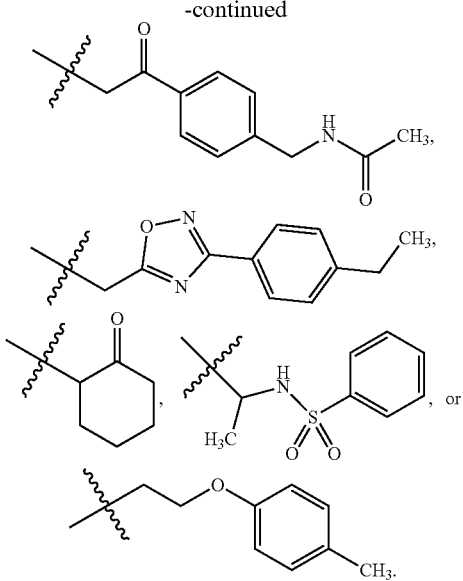

In an embodiment of the present invention, $R_4$ is H, ($C_5$-$C_{10}$) aryl, ($C_5$-$C_{10}$) heteroaryl, or 5-to 14-membered heterocyclyl including 1-5 heteroatoms selected from N, O and S, where the aryl or heterocyclyl is optionally substituted with one or more ($C_5$-$C_{10}$) aryl, ($C_1$-$C_6$) alkyl, ($C_3$-$C_6$) cycloalkyl, ($C_1$-$C_6$) haloalkyl, ($C_1$-$C_6$) alkoxy, ($C_1$-$C_6$) haloalkoxy, ($C_2$-$C_6$)alkenyl, ($C_2$-$C_6$) alkynyl, halogen, nitro, —CN, oxo, —B(OH)$_2$, —OH, —COOH, —SH, —NH$_2$, —NH($C_1$-$C_4$) alkyl, —N(($C_1$-$C_4$) alkyl)$_2$, or —(CH$_2$)$_n$NC(O)($C_1$-$C_4$) alkyl.

In an embodiment of the present invention, $R_4$ is H, ($C_5$-$C_{10}$) aryl, ($C_5$-$C_{10}$) heteroaryl, or 5-to 14-membered heterocyclyl including 1-5 heteroatoms selected from N, O and S.

In an embodiment of the present invention, $R_4$ is H.

In an embodiment of the present invention, $R_4$ is ($C_5$-$C_{10}$) aryl, ($C_5$-$C_{10}$) heteroaryl, or 5-to 14-membered heterocyclyl including 1-5 heteroatoms selected from N, O and S, where the aryl or heterocyclyl is optionally substituted with one or more ($C_5$-$C_{10}$) aryl, ($C_1$-$C_6$) alkyl, ($C_3$-$C_6$) cycloalkyl, ($C_1$-$C_6$) haloalkyl, ($C_1$-$C_6$) alkoxy, ($C_1$-$C_6$) haloalkoxy, ($C_2$-$C_6$) alkenyl, ($C_2$-$C_6$) alkynyl, halogen, nitro, —CN, oxo, —B(OH)$_2$, —OH, —COOH, —SH, —NH$_2$, —NH($C_1$-$C_4$) alkyl, —N(($C_1$-$C_4$) alkyl)$_2$, or —(CH$_2$)$_n$NC(O)($C_1$-$C_4$) alkyl.

In an embodiment of the present invention, $R_4$ is ($C_5$-$C_{10}$) aryl, ($C_5$-$C_{10}$) heteroaryl, or 5-to 14-membered heterocyclyl including 1-5 heteroatoms selected from N, O and S.

In an embodiment of the present invention, $R_4$ is ($C_5$-$C_{10}$) aryl optionally substituted with one or more ($C_5$-$C_{10}$) aryl, ($C_1$-$C_6$) alkyl, ($C_3$-$C_6$) cycloalkyl, ($C_1$-$C_6$) haloalkyl, ($C_1$-$C_6$) alkoxy, ($C_1$-$C_6$) haloalkoxy, ($C_2$-$C_6$) alkenyl, ($C_2$-$C_6$) alkynyl, halogen, nitro, —CN, oxo, —B(OH)$_2$, —OH, —COOH, —SH, —NH$_2$, —NH($C_1$-$C_4$) alkyl, —N(($C_1$-$C_4$) alkyl)$_2$, or —(CH$_2$)$_n$NC(O)($C_1$-$C_4$)alkyl.

In an embodiment of the present invention, $R_4$ is ($C_5$-$C_{10}$) aryl optionally substituted with one or more ($C_1$-$C_6$) alkyl.

In an embodiment of the present invention, $R_4$ is ($C_5$-$C_{10}$) aryl optionally substituted with one or more ($C_1$-$C_6$) alkoxy.

In an embodiment of the present invention, $R_4$ is ($C_5$-$C_{10}$) aryl optionally substituted one or more halogen.

In an embodiment of the present invention, $R_4$ is ($C_5$-$C_{10}$) aryl optionally substituted with one or more —(CH$_2$)$_n$NC(O)($C_1$-$C_4$) alkyl.

In an embodiment of the present invention, $R_4$ is ($C_5$-$C_{10}$) aryl.

In an embodiment of the present invention, $R_4$ is ($C_5$-$C_{10}$) heteroaryl optionally substituted with one or more ($C_5$-$C_{10}$) aryl, ($C_1$-$C_6$) alkyl, ($C_3$-$C_6$) cycloalkyl, ($C_1$-$C_6$) haloalkyl, ($C_1$-$C_6$) alkoxy, ($C_1$-$C_6$) haloalkoxy, ($C_2$-$C_6$) alkenyl, ($C_2$-$C_6$) alkynyl, halogen, nitro, —CN, oxo, —B(OH)$_2$, —OH, —COOH, —SH, —NH$_2$, —NH($C_1$-$C_4$) alkyl, —N(($C_1$-$C_4$) alkyl)$_2$, or —(CH$_2$)$_n$NC(O)($C_1$-$C_4$)alkyl.

In an embodiment of the present invention, $R_4$ is ($C_5$-$C_{10}$) heteroaryl optionally substituted with one or more ($C_5$-$C_{10}$) aryl.

In an embodiment of the present invention, $R_4$ is ($C_5$-$C_{10}$) heteroaryl substituted with one or more ($C_5$-$C_{10}$) aryl.

In an embodiment of the present invention, $R_4$ is

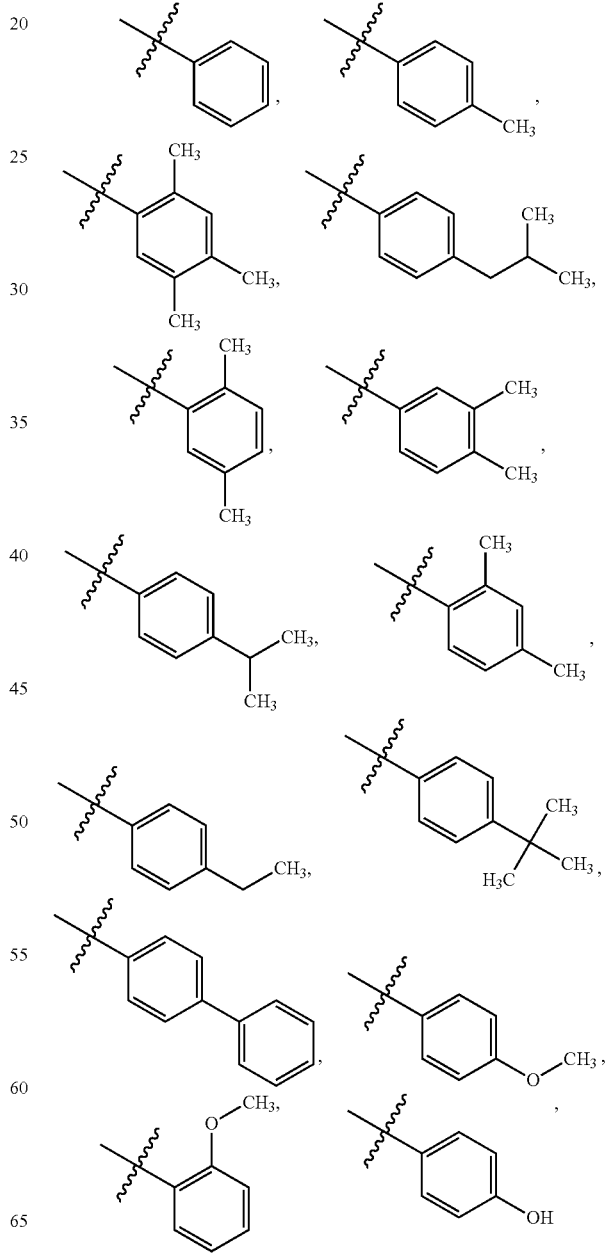

-continued

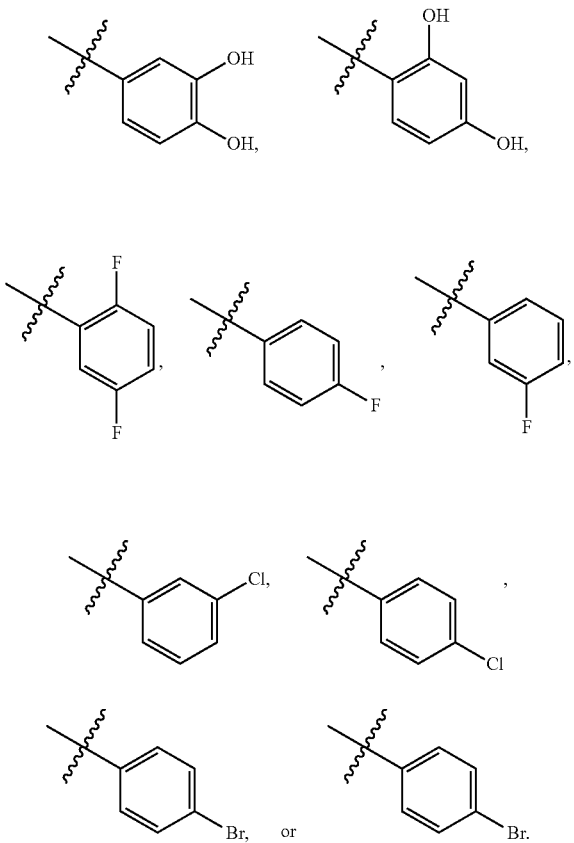

In an embodiment of the present invention, X is N and Y is S.

In an embodiment of the present invention, X is N, Y is S, and $R_1$ is $(C_1-C_6)$ alkyl.

In an embodiment of the present invention, X is N, Y is S, and $R_1$ is methyl.

In an embodiment of the present invention, X is N, Y is S, and $R_1$ is $(C_5-C_{10})$ aryl.

In an embodiment of the present invention, X is N, Y is S, and $R_1$ is $(C_5-C_{10})$ aryl optionally substituted with one or more $R_{1a}$.

In an embodiment of the present invention, X is N, Y is S, R is $(C_5-C_{10})$ aryl, and $R_2$ is H.

In an embodiment of the present invention, X is N, Y is S, R is $(C_5-C_{10})$ aryl, and $R_2$ is methyl.

In an embodiment of the present invention, X is N, Y is S, R is $(C_5-C_{10})$ aryl, and $R_2$ is p-methoxyphenyl.

In an embodiment of the present invention, X is N, Y is S, R is $(C_5-C_{10})$ aryl optionally substituted with one or more $R_{1a}$, and $R_2$ is H.

In an embodiment of the present invention, X is N, Y is S, $R_1$ is $(C_5-C_{10})$ aryl optionally substituted with one or more $R_{1a}$, and $R_2$ is methyl.

In an embodiment of the present invention, X is N, Y is S, $R_1$ is $(C_5-C_{10})$ aryl optionally substituted with one or more $R_{1a}$, and $R_2$ is p-methoxyphenyl.

In an embodiment of the present invention, X is N, Y is S, $R_1$ is $(C_5-C_{10})$ aryl optionally substituted with one or more $R_{1a}$, and $R_2$ is H, and $R_3$ is oxo substituted $(C_3-C_6)$ cycloalkyl.

In an embodiment of the present invention, X is N, Y is S, $R_1$ is $(C_5-C_{10})$ aryl optionally substituted with one or more $R_{1a}$, $R_2$ is H, and $R_3$ is oxo substituted $(C_1-C_6)$ alkyl.

In an embodiment of the present invention, X is N, Y is S, $R_1$ is $(C_5-C_{10})$ aryl optionally substituted with one or more $R_{1a}$, $R_2$ is methyl, and $R_3$ is oxo substituted $(C_1-C_6)$ alkyl.

In an embodiment of the present invention, X is N, Y is S, $R_1$ is $(C_5-C_{10})$ aryl optionally substituted with one or more $R_{1a}$, $R_2$ is p-methoxyphenyl, and $R_3$ is oxo substituted $(C_1-C_6)$ alkyl.

In an embodiment of the present invention, X is N, Y is S, $R_1$ is $(C_5-C_{10})$ aryl optionally substituted with one or more $R_{1a}$, $R_2$ is H, and $R_3$ is oxo substituted $(C_1-C_6)$ alkyl optionally substituted with one or more $R_4$.

In an embodiment of the present invention, X is N, Y is S, $R_1$ is $(C_5-C_{10})$ aryl optionally substituted with one or more $R_{1a}$, $R_2$ is methyl, and $R_3$ is oxo substituted $(C_1-C_6)$ alkyl optionally substituted with one or more $R_4$.

In an embodiment of the present invention, X is N, Y is S, $R_1$ is $(C_5-C_{10})$ aryl optionally substituted with one or more $R_{1a}$, $R_2$ is p-methoxyphenyl, and $R_3$ is oxo substituted $(C_1-C_6)$ alkyl optionally substituted with one or more $R_4$.

In an embodiment of the present invention, the compound of Formula (I) is Formula (Ib) and m is 0, 1 or 2. In an embodiment, the compound of Formula (I) is Formula (Ib) and m is 1, 2 or 3. In an embodiment, the compound of Formula (I) is Formula (Ib) and m is 0, or 1. In an embodiment, the compound of Formula (I) is Formula (Ib) and m is 1 or 2.

In an embodiment of the present invention, the compound of Formula (I) is Formula (Ic) and m is 0, 1 or 2. In an embodiment, the compound of Formula (I) is Formula (Ic) and m is 1, 2 or 3. In an embodiment, the compound of Formula (I) is Formula (Ic) and m is 0, or 1. In an embodiment, the compound of Formula (I) is Formula (Ic) and m is 1 or 2.

In an embodiment of the present invention, the compound of Formula (I) is Formula (e) and m is 0, 1 or 2. In an embodiment, the compound of Formula (I) is Formula (Je) and m is 1, 2 or 3. In an embodiment, the compound of Formula (I) is Formula (Ie) and m is 0, or 1. In an embodiment, the compound of Formula (I) is Formula (Ie) and m is 1 or 2.

There is a need for novel and potent small molecule STING modulators. The present application addresses this need. STING agonists, such as CDN's have been shown to exert potent anti-tumor properties, likely by stimulating APCs and subsequent anti-tumor T cell activity and are now being evaluated in Phase I trials for the treatment of cancer. The compounds of this invention modulate the activity of STING, and accordingly, can provide a beneficial therapeutic impact in treatment of diseases, disorders and/or conditions in which modulation of STING is beneficial, for example for inflammation, allergic and autoimmune diseases, infectious diseases, cancer, pre-cancerous syndromes and as vaccine adjuvants.

In various embodiments of the invention, novel small molecules that have been chemically synthesized have been shown to bind to and activate STING signaling for use in anti-microbial, anti-tumor, vaccine and therapeutic strategies.

Table I shows non-limiting illustrative examples of compounds.

| Cmpd. No. | Structure | Compound Name |
|---|---|---|
| 1 | 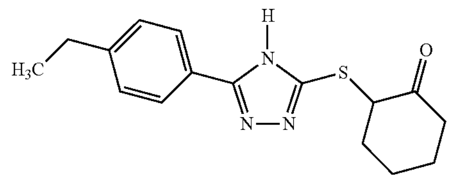 [SMILES: CCc1ccc(-c2nnc(SC3CCCCC3=O)[nH]2)cc1] | 2-((5-(4-ethylphenyl)-4H-1,2,4-triazol-3-yl)thio)cyclohexan-1-one |
| 2 | 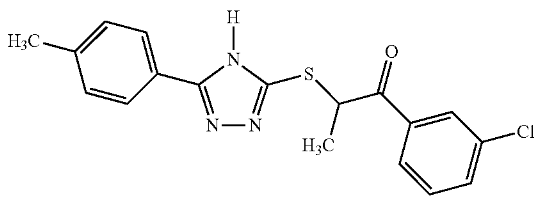 [SMILES: Cc1ccc(-c2nnc(SC(C)C(=O)c3cccc(Cl)c3)[nH]2)cc1] | 1-(3-chlorophenyl)-2-((5-(p-tolyl)-4H-1,2,4-triazol-3-yl)thio)propan-1-one |
| 3 | 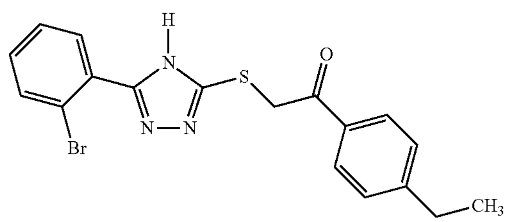 [SMILES: CCc1ccc(C(=O)CSc2nnc(-c3ccccc3Br)[nH]2)cc1] | 2-((5-(2-bromophenyl)-4H-1,2,4-triazol-3-yl)thio)-1-(4-ethylphenyl)ethan-1-one |
| 4 | 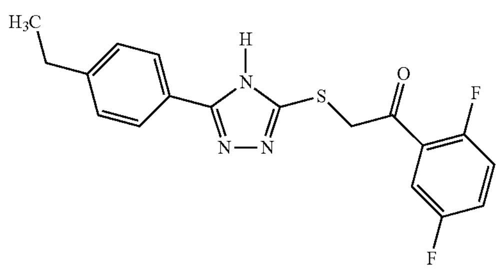 [SMILES: CCc1ccc(-c2nnc(SCC(=O)c3cc(F)ccc3F)[nH]2)cc1] | 1-(2,5-difluorophenyl)-2-((5-(4-ethylphenyl)-4H-1,2,4-triazol-3-yl)thio)ethan-1-one |
| 5 | 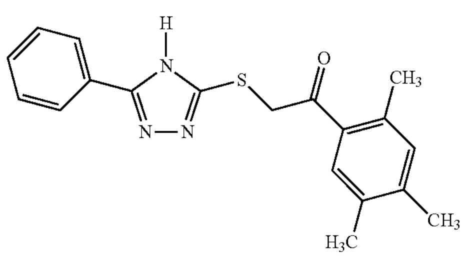 [SMILES: Cc1cc(C)c(C(=O)CSc2nnc(-c3ccccc3)[nH]2)cc1C] | 2-((5-phenyl-4H-1,2,4-triazol-3-yl)thio)-1-(2,4,5-trimethylphenyl)ethan-1-one |
| 6 | 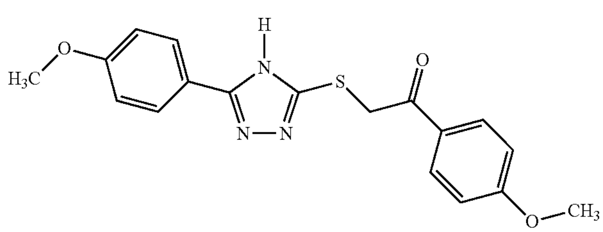 | 1-(4-methoxyphenyl)-2-((5-(4-methoxyphenyl)-4H-1,2,4-triazol-3-yl)thio)ethan-1-one |
| 7 | 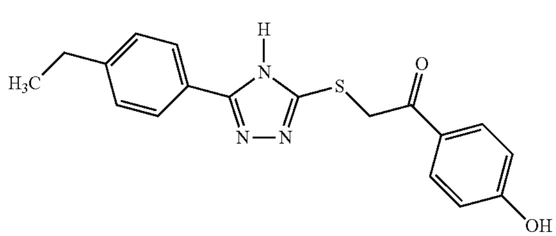 [SMILES: CCc1ccc(-c2nnc(SCC(=O)c3ccc(O)cc3)[nH]2)cc1] | 2-((5-(4-ethylphenyl)-4H-1,2,4-triazol-3-yl)thio)-1-(4-hydroxyphenyl)ethan-1-one |

-continued

| Cmpd. No. | Structure | Compound Name |
|---|---|---|
| 8 | 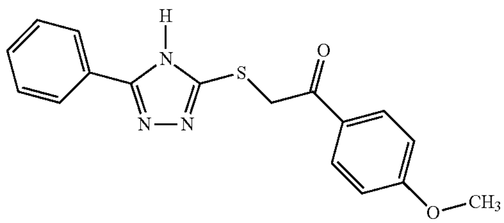 [SMILES: COc1ccc(C(=O)CSc2nnc(-c3ccccc3)[nH]2)cc1] | 1-(4-methoxyphenyl)-2-((5-phenyl-4H-1,2,4-triazol-3-yl)thio)ethan-1-one |
| 9 | 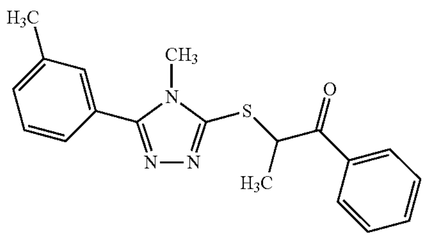 [SMILES: Cc1cccc(-c2nnc(SC(C)C(=O)c3ccccc3)n2C)c1] | 2-((4-methyl-5-(m-tolyl)-4H-1,2,4-triazol-3-yl)thio)-1-phenylpropan-1-one |
| 10 | 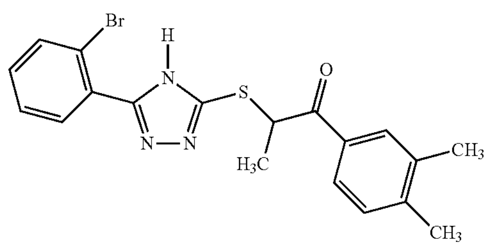 [SMILES: Cc1ccc(C(=O)C(C)Sc2nnc(-c3ccccc3Br)[nH]2)cc1C] | 2-((5-(2-bromophenyl)-4H-1,2,4-triazol-3-yl)thio)-1-(3,4-dimethylphenyl)propan-1-one |
| 11 | 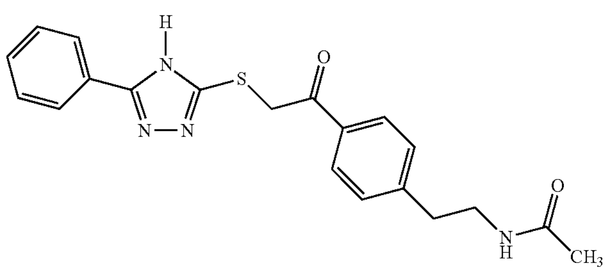 [SMILES: CC(=O)NCCc1ccc(C(=O)CSc2nnc(-c3ccccc3)[nH]2)cc1] | N-(4-(2-((5-phenyl-4H-1,2,4-triazol-3-yl)thio)acetyl)phenethyl)acetamide |
| 12 | 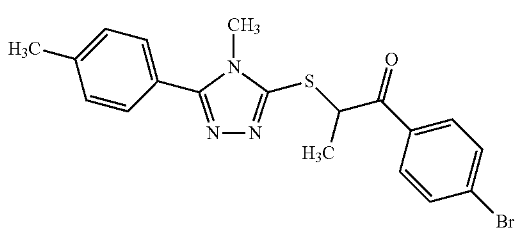 [SMILES: Cc1ccc(-c2nnc(SC(C)C(=O)c3ccc(Br)cc3)n2C)cc1] | 1-(4-bromophenyl)-2-((4-methyl-5-(p-tolyl)-4H-1,2,4-triazol-3-yl)thio)propan-1-one |
| 13 | 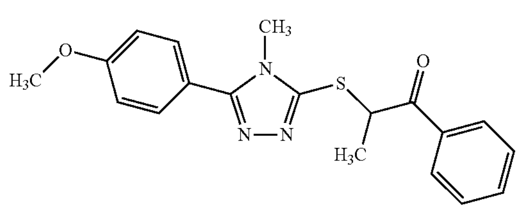 [SMILES: COc1ccc(-c2nnc(SC(C)C(=O)c3ccccc3)n2C)cc1] | 2-((5-(4-methoxyphenyl)-4-methyl-4H-1,2,4-triazol-3-yl)thio)-1-phenylpropan-1-one |

-continued

| Cmpd. No. | Structure | Compound Name |
|---|---|---|
| 14 | 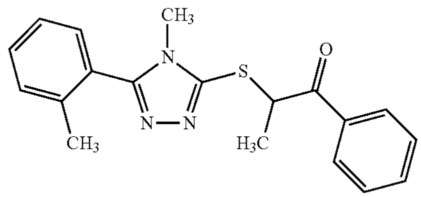 [SMILES: Cc1ccccc1-c1nnc(SC(C)C(=O)c2ccccc2)n1C] | 2-((4-methyl-5-(o-tolyl)-4H-1,2,4-triazol-3-yl)thio)-1-phenylpropan-1-one |
| 15 | 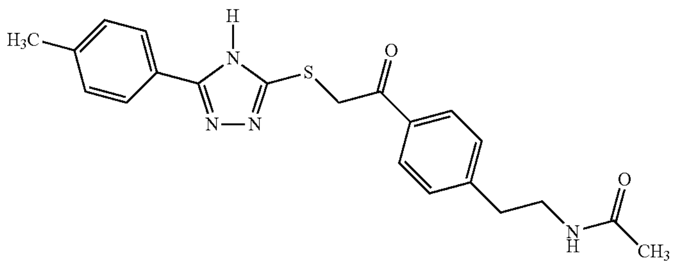 [SMILES: CC(=O)NCCc1ccc(C(=O)CSc2nnc(-c3ccc(C)cc3)[nH]2)cc1] | N-(4-(2-((5-(p-tolyl)-4H-1,2,4-triazol-3-yl)thio)acetyl)phenethyl)acetamide |
| 16 | 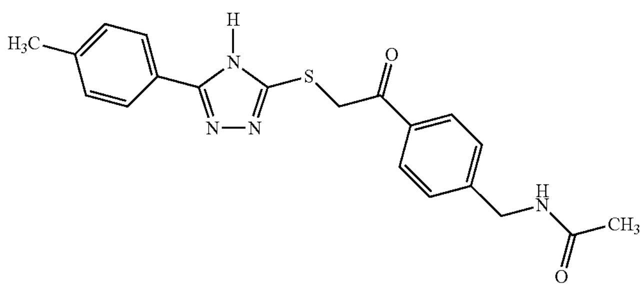 [SMILES: CC(=O)NCc1ccc(C(=O)CSc2nnc(-c3ccc(C)cc3)[nH]2)cc1] | N-(4-(2-((5-(p-tolyl)-4H-1,2,4-triazol-3-yl)thio)acetyl)benzyl)acetamide |
| 17 | 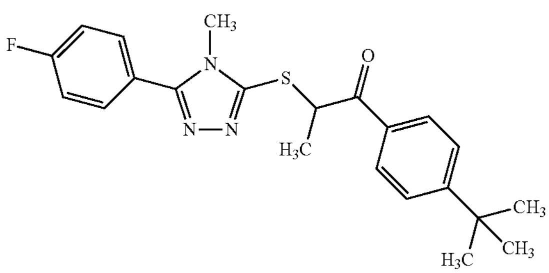 [SMILES: CC(Sc1nnc(-c2ccc(F)cc2)n1C)C(=O)c1ccc(C(C)(C)C)cc1] | 1-(4-(tert-butyl)phenyl)-2-((5-(4-fluorophenyl)-4-methyl-4H-1,2,4-triazol-3-yl)thio)propan-1-one |
| 18 | 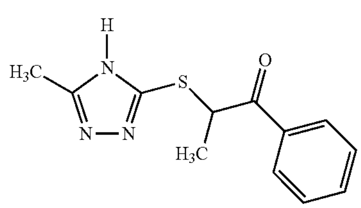 [SMILES: Cc1nnc(SC(C)C(=O)c2ccccc2)[nH]1] | 2-((5-methyl-4H-1,2,4-triazol-3-yl)thio)-1-phenylpropan-1-one |
| 19 | 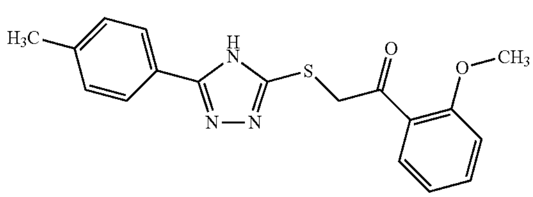 | 1-(2-methoxyphenyl)-2-((5-(p-tolyl)-4H-1,2,4-triazol-3-yl)thio)ethan-1-one |

-continued

| Cmpd. No. | Structure | Compound Name |
|---|---|---|
| 20 | 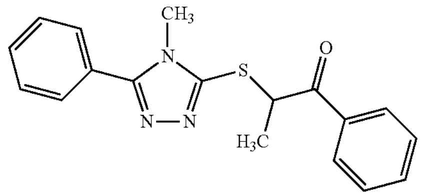 [SMILES: CC(Sc1nnc(-c2ccccc2)n1C)C(=O)c1ccccc1] | 2-((4-methyl-5-phenyl-4H-1,2,4-triazol-3-yl)thio)-1-phenylpropan-1-one |
| 21 | 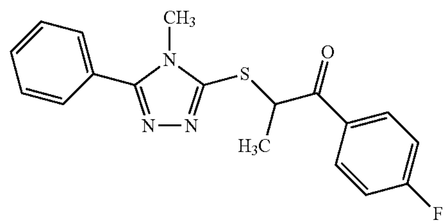 [SMILES: CC(Sc1nnc(-c2ccccc2)n1C)C(=O)c1ccc(F)cc1] | 1-(4-fluorophenyl)-2-((4-methyl-5-phenyl-4H-1,2,4-triazol-3-yl)thio)propan-1-one |
| 22 | 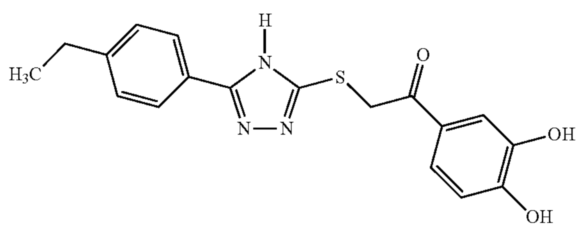 [SMILES: CCc1ccc(-c2nnc(SCC(=O)c3ccc(O)c(O)c3)[nH]2)cc1] | 1-(3,4-dihydroxyphenyl)-2-((5-(4-ethylphenyl)-4H-1,2,4-triazol-3-yl)thio)ethan-1-one |
| 23 | 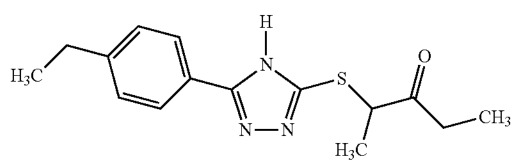 [SMILES: CCC(=O)C(C)Sc1nnc(-c2ccc(CC)cc2)[nH]1] | 2-((5-(4-ethylphenyl)-4H-1,2,4-triazol-3-yl)thio)pentan-3-one |
| 24 | 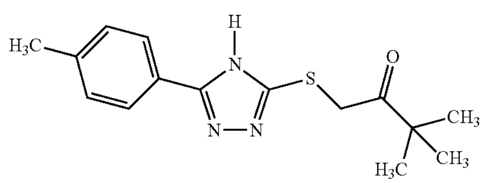 [SMILES: Cc1ccc(-c2nnc(SCC(=O)C(C)(C)C)[nH]2)cc1] | 3,3-dimethyl-1-((5-(p-tolyl)-4H-1,2,4-triazol-3-yl)thio)butan-2-one |
| 25 | 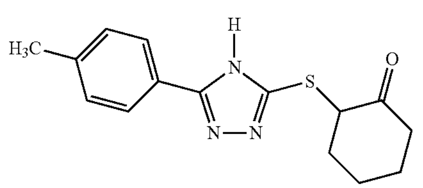 [SMILES: Cc1ccc(-c2nnc(SC3CCCCC3=O)[nH]2)cc1] | 2-((5-(p-tolyl)-4H-1,2,4-triazol-3-yl)thio)cyclohexan-1-one |
| 26 | 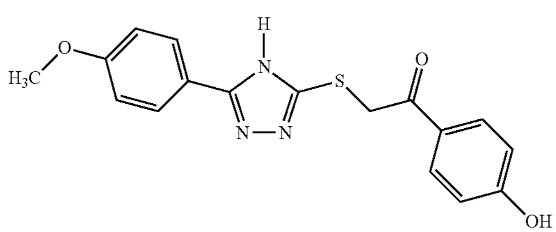 [SMILES: COc1ccc(-c2nnc(SCC(=O)c3ccc(O)cc3)[nH]2)cc1] | 1-(4-hydroxyphenyl)-2-((5-(4-methoxyphenyl)-4H-1,2,4-triazol-3-yl)thio)ethan-1-one |

-continued

| Cmpd. No. | Structure | Compound Name |
|---|---|---|
| 27 | 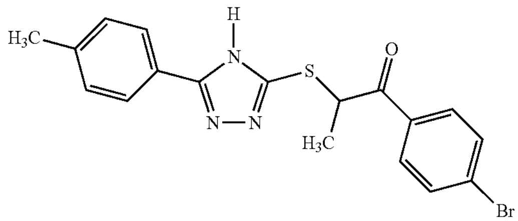 [SMILES: Cc1ccc(-c2nnc(SC(C)C(=O)c3ccc(Br)cc3)[nH]2)cc1] | 1-(4-bromophenyl)-2-((5-(p-tolyl)-4H-1,2,4-triazol-3-yl)thio)propan-1-one |
| 28 | 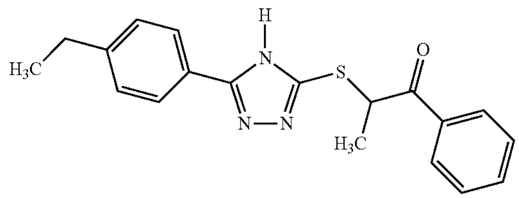 [SMILES: CCc1ccc(-c2nnc(SC(C)C(=O)c3ccccc3)[nH]2)cc1] | 2-((5-(4-ethylphenyl)-4H-1,2,4-triazol-3-yl)thio)-1-phenylpropan-1-one |
| 29 | 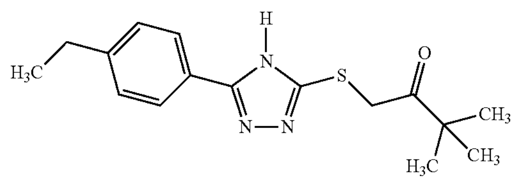 [SMILES: CCc1ccc(-c2nnc(SCC(=O)C(C)(C)C)[nH]2)cc1] | 1-((5-(4-ethylphenyl)-4H-1,2,4-triazol-3-yl)thio)-3,3-dimethylbutan-2-one |
| 30 | 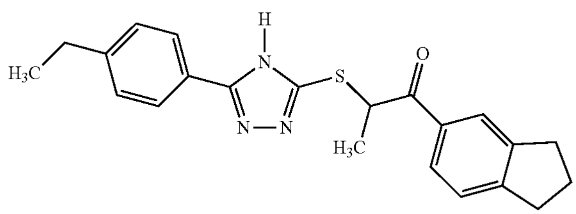 [SMILES: CCc1ccc(-c2nnc(SC(C)C(=O)c3ccc4c(c3)CCC4)[nH]2)cc1] | 1-(2,3-dihydro-1H-inden-5-yl)-2-((5-(4-ethylphenyl)-4H-1,2,4-triazol-3-yl)thio)propan-1-one |
| 31 | 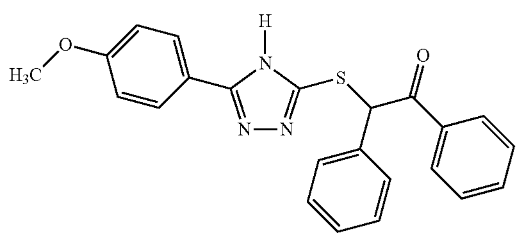 [SMILES: COc1ccc(-c2nnc(SC(C(=O)c3ccccc3)c3ccccc3)[nH]2)cc1] | 2-((5-(4-methoxyphenyl)-4H-1,2,4-triazol-3-yl)thio)-1,2-diphenylethan-1-one |
| 32 | 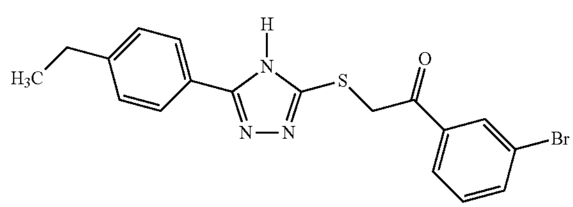 [SMILES: CCc1ccc(-c2nnc(SCC(=O)c3cccc(Br)c3)[nH]2)cc1] | 1-(3-bromophenyl)-2-((5-(4-ethylphenyl)-4H-1,2,4-triazol-3-yl)thio)ethan-1-one |
| 33 | 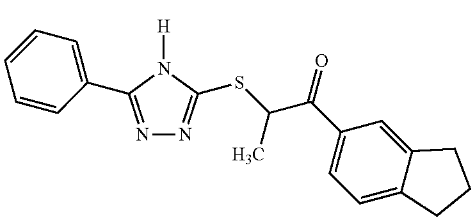 [SMILES: CC(Sc1nnc(-c2ccccc2)[nH]1)C(=O)c1ccc2c(c1)CCC2] | 1-(2,3-dihydro-1H-inden-5-yl)-2-((5-phenyl-4H-1,2,4-triazol-3-yl)thio)propan-1-one |

-continued

| Cmpd. No. | Structure | Compound Name |
|---|---|---|
| 34 | 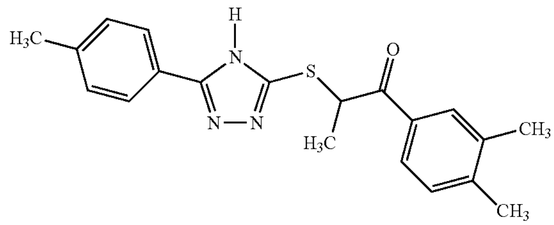 | 1-(3,4-dimethylphenyl)-2-((5-(p-tolyl)-4H-1,2,4-triazol-3-yl)thio)propan-1-one |
| 35 | 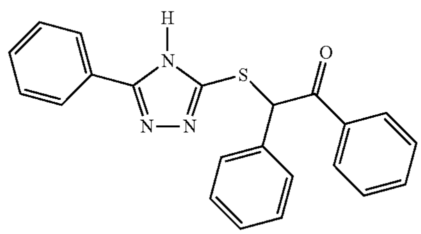 [SMILES: O=C(c1ccccc1)C(Sc1nnc(-c2ccccc2)[nH]1)c1ccccc1] | 1,2-diphenyl-2-((5-phenyl-4H-1,2,4-triazol-3-yl)thio)ethan-1-one |
| 36 | 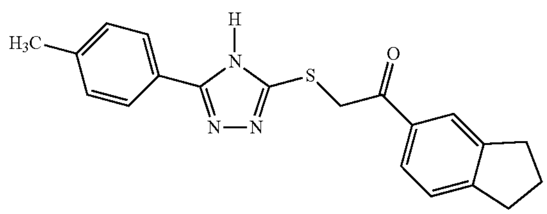 [SMILES: Cc1ccc(-c2nnc(SCC(=O)c3ccc4c(c3)CCC4)[nH]2)cc1] | 1-(2,3-dihydro-1H-inden-5-yl)-2-((5-(p-tolyl)-4H-1,2,4-triazol-3-yl)thio)ethan-1-one |
| 37 | 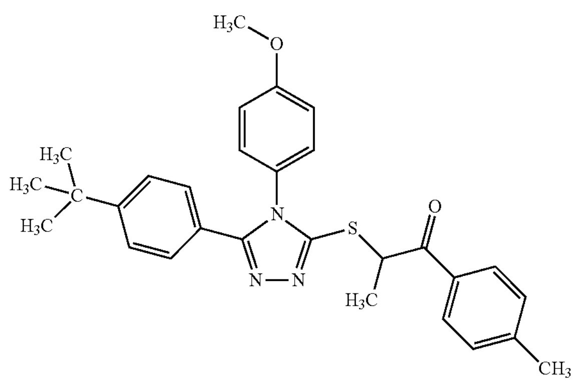 [SMILES: COc1ccc(-n2c(SC(C)C(=O)c3ccc(C)cc3)nnc2-c2ccc(C(C)(C)C)cc2)cc1] | 2-((5-(4-(tert-butyl)phenyl)-4-(4-methoxyphenyl)-4H-1,2,4-triazol-3-yl)thio)-1-(p-tolyl)propan-1-one |
| 38 | 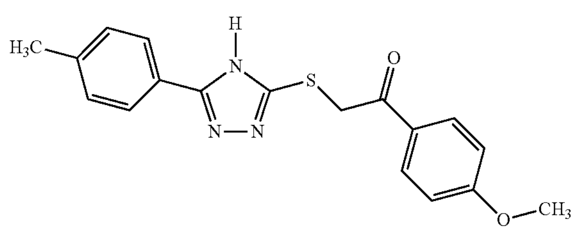 | 1-(4-methoxyphenyl)-2-((5-(p-tolyl)-4H-1,2,4-triazol-3-yl)thio)ethan-1-one |
| 39 | 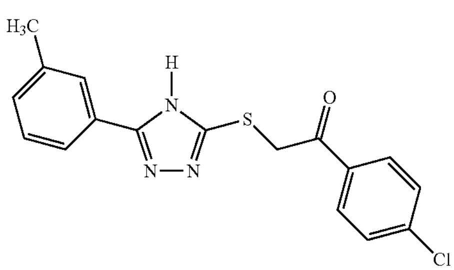 [SMILES: Cc1cccc(-c2nnc(SCC(=O)c3ccc(Cl)cc3)[nH]2)c1] | 1-(4-chlorophenyl)-2-((5-(m-tolyl)-4H-1,2,4-triazol-3-yl)thio)ethan-1-one |

| Cmpd. No. | Structure | Compound Name |
|---|---|---|
| 40 | 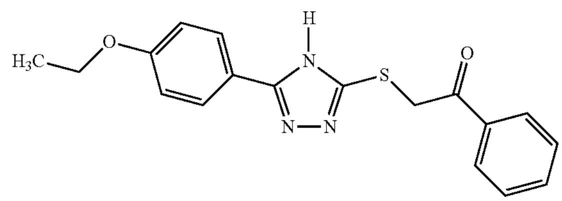 [SMILES: CCOc1ccc(-c2nnc(SCC(=O)c3ccccc3)[nH]2)cc1] | 2-((5-(4-ethoxyphenyl)-4H-1,2,4-triazol-3-yl)thio)-1-phenylethan-1-one |
| 41 | 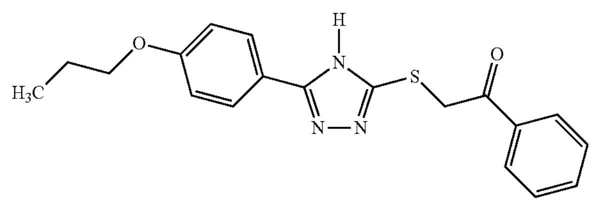 [SMILES: CCCOc1ccc(-c2nnc(SCC(=O)c3ccccc3)[nH]2)cc1] | 1-phenyl-2-((5-(4-propoxyphenyl)-4H-1,2,4-triazol-3-yl)thio)ethan-1-one |
| 42 | 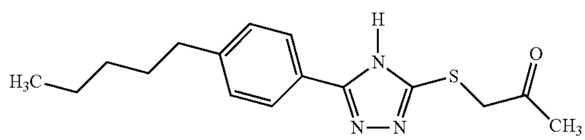 [SMILES: CCCCCc1ccc(-c2nnc(SCC(C)=O)[nH]2)cc1] | 1-((5-(4-pentylphenyl)-4H-1,2,4-triazol-3-yl)thio)propan-2-one |
| 43 | 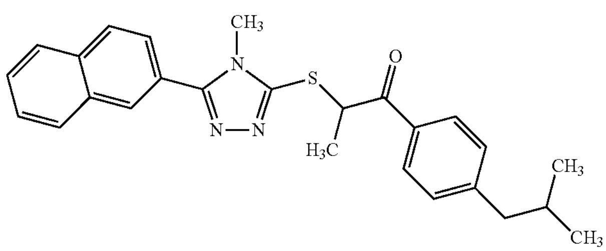 [SMILES: CC(C)Cc1ccc(C(=O)C(C)Sc2nnc(-c3ccc4ccccc4c3)n2C)cc1] | 1-(4-isobutylphenyl)-2-((4-methyl-5-(naphthalen-2-yl)-4H-1,2,4-triazol-3-yl)thio)propan-1-one |
| 44 | 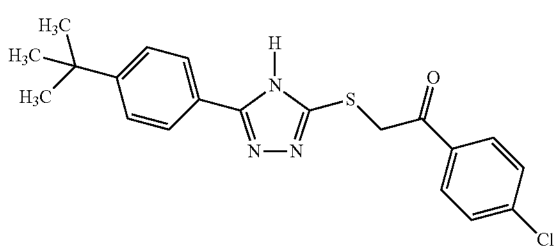 [SMILES: CC(C)(C)c1ccc(-c2nnc(SCC(=O)c3ccc(Cl)cc3)[nH]2)cc1] | 2-((5-(4-(tert-butyl)phenyl)-4H-1,2,4-triazol-3-yl)thio)-1-(4-chlorophenyl)ethan-1-one |
| 45 | 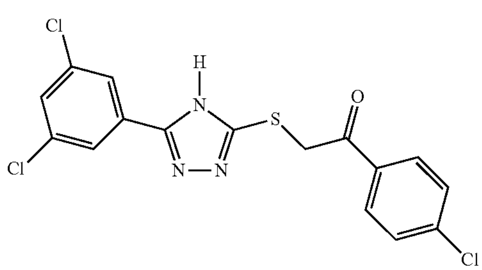 [SMILES: O=C(CSc1nnc(-c2cc(Cl)cc(Cl)c2)[nH]1)c1ccc(Cl)cc1] | 1-(4-chlorophenyl)-2-((5-(3,5-dichlorophenyl)-4H-1,2,4-triazol-3-yl)thio)ethan-1-one |
| 46 | 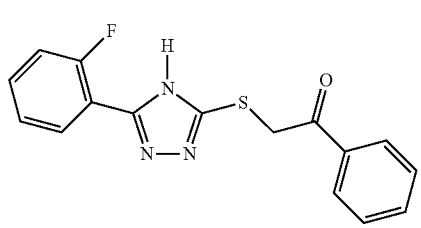 [SMILES: O=C(CSc1nnc(-c2ccccc2F)[nH]1)c1ccccc1] | 2-((5-(2-fluorophenyl)-4H-1,2,4-triazol-3-yl)thio)-1-phenylethan-1-one |

-continued

| Cmpd. No. | Structure | Compound Name |
|---|---|---|
| 47 | 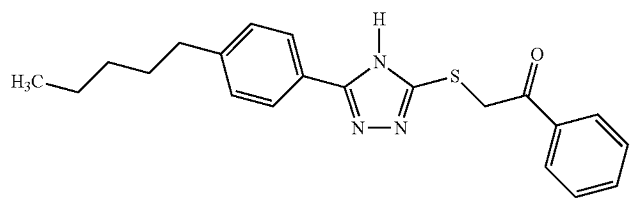 [SMILES: CCCCCc1ccc(-c2nnc(SCC(=O)c3ccccc3)[nH]2)cc1] | 2-((5-(4-pentylphenyl)-4H-1,2,4-triazol-3-yl)thio)-1-phenylethan-1-one |
| 48 | 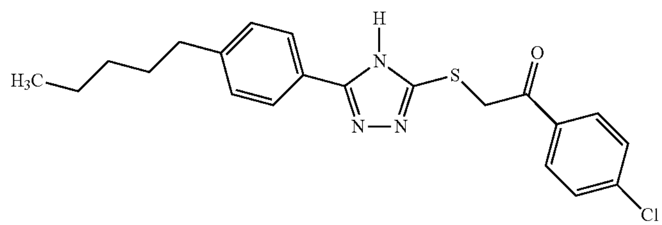 [SMILES: CCCCCc1ccc(-c2nnc(SCC(=O)c3ccc(Cl)cc3)[nH]2)cc1] | 1-(4-chlorophenyl)-2-((5-(4-pentylphenyl)-4H-1,2,4-triazol-3-yl)thio)ethan-1-one |
| 49 | 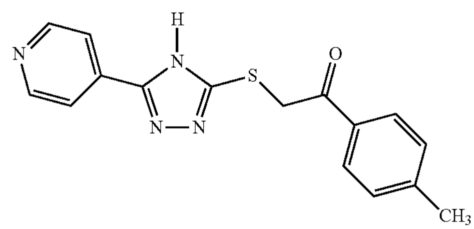 [SMILES: Cc1ccc(C(=O)CSc2nnc(-c3ccncc3)[nH]2)cc1] | 2-((5-(pyridin-4-yl)-4H-1,2,4-triazol-3-yl)thio)-1-(p-tolyl)ethan-1-one |
| 50 | 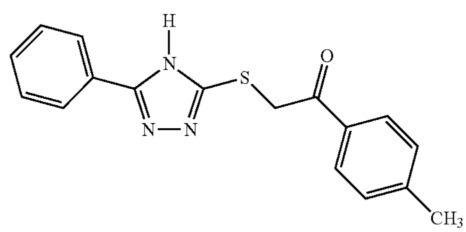 [SMILES: Cc1ccc(C(=O)CSc2nnc(-c3ccccc3)[nH]2)cc1] | 2-((5-phenyl-4H-1,2,4-triazol-3-yl)thio)-1-(p-tolyl)ethan-1-one |
| 51 | 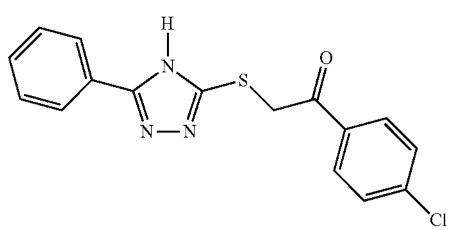 [SMILES: O=C(CSc1nnc(-c2ccccc2)[nH]1)c1ccc(Cl)cc1] | 1-(4-chlorophenyl)-2-((5-phenyl-1,2,4-triazol-3-yl)thio)ethan-1-one |
| 52 | 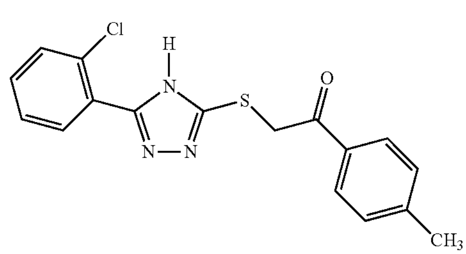 [SMILES: Cc1ccc(C(=O)CSc2nnc(-c3ccccc3Cl)[nH]2)cc1] | 2-((5-(2-chlorophenyl)-4H-1,2,4-triazol-3-yl)thio)-1-(p-tolyl)ethan-1-one |

-continued
| Cmpd. No. | Structure | Compound Name |
|---|---|---|
| 53 | 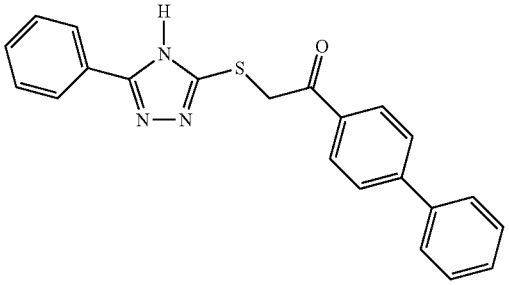 [SMILES: O=C(CSc1nnc(-c2ccccc2)[nH]1)c1ccc(-c2ccccc2)cc1] | 1-([1,1'-biphenyl]-4-yl)-2-((5-phenyl-4H-1,2,4-triazol-3-yl)thio)ethan-1-one |
| 54 | 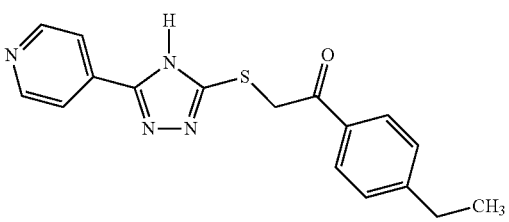 [SMILES: CCc1ccc(C(=O)CSc2nnc(-c3ccncc3)[nH]2)cc1] | 1-(4-ethylphenyl)-2-((5-(pyridin-4-yl)-4H-1,2,4-triazol-3-yl)thio)ethan-1-one |
| 55 | 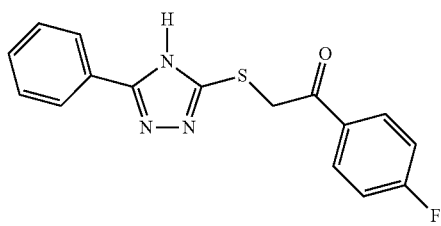 [SMILES: O=C(CSc1nnc(-c2ccccc2)[nH]1)c1ccc(F)cc1] | 1-(4-fluorophenyl)-2-((5-phenyl-4H-1,2,4-triazol-3-yl)thio)ethan-1-one |
| 56 | 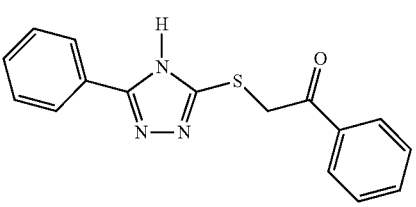 [SMILES: O=C(CSc1nnc(-c2ccccc2)[nH]1)c1ccccc1] | 1-phenyl-2-((5-phenyl-4H-1,2,4-triazol-3-yl)thio)ethan-1-one |
| 57 | 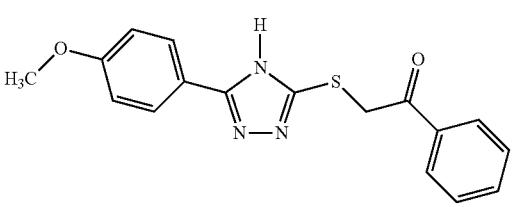 [SMILES: COc1ccc(-c2nnc(SCC(=O)c3ccccc3)[nH]2)cc1] | 2-((5-(4-methoxyphenyl)-4H-1,2,4-triazol-3-yl)thio)-1-phenylethan-1-one |
| 58 | 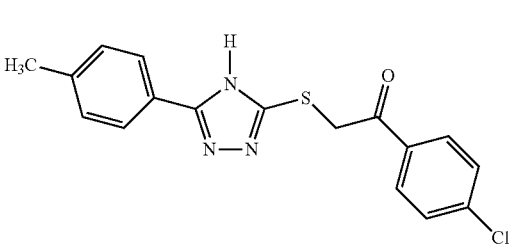 [SMILES: Cc1ccc(-c2nnc(SCC(=O)c3ccc(Cl)cc3)[nH]2)cc1] | 1-(4-chlorophenyl)-2-((5-(p-tolyl)-4H-1,2,4-triazol-3-yl)thio)ethan-1-one |

-continued

| Cmpd. No. | Structure | Compound Name |
|---|---|---|
| 59 | 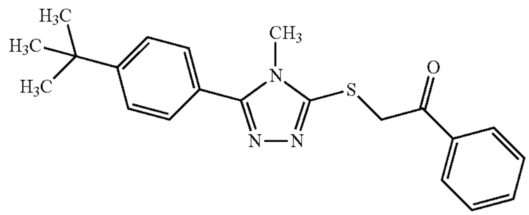 [SMILES: Cn1c(SCC(=O)c2ccccc2)nnc1-c1ccc(C(C)(C)C)cc1] | 2-((5-(4-(tert-butyl)phenyl)-4-methyl-4H-1,2,4-triazol-3-yl)thio)-1-phenylethan-1-one |
| 60 | 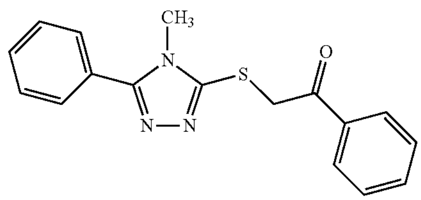 [SMILES: Cn1c(SCC(=O)c2ccccc2)nnc1-c1ccccc1] | 2-((4-methyl-5-phenyl-4H-1,2,4-triazol-3-yl)thio)-1-phenylethan-1-one |
| 61 | 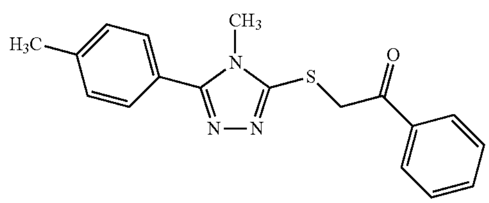 [SMILES: Cc1ccc(-c2nnc(SCC(=O)c3ccccc3)n2C)cc1] | 2-((4-methyl-5-(p-tolyl)-4H-1,2,4-triazol-3-yl)thio)-1-phenylethan-1-one |
| 62 | 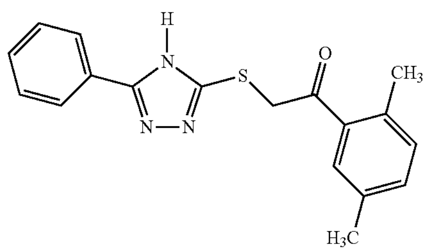 [SMILES: Cc1ccc(C)c(C(=O)CSc2nnc(-c3ccccc3)[nH]2)c1] | 1-(2,5-dimethylphenyl)-2-((5-phenyl-4H-1,2,4-triazol-3-yl)thio)ethan-1-one |
| 63 | 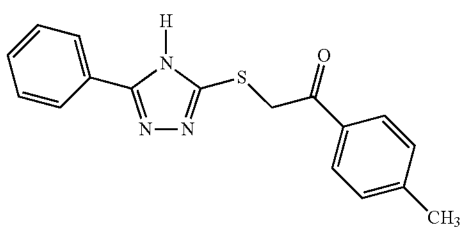 [SMILES: Cc1ccc(C(=O)CSc2nnc(-c3ccccc3)[nH]2)cc1] | 2-((5-phenyl-4H-1,2,4-triazol-3-yl)thio)-1-(p-tolyl)ethan-1-one |
| 64 | 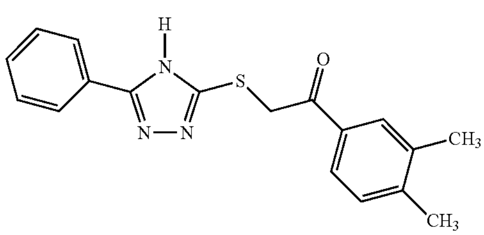 [SMILES: Cc1ccc(C(=O)CSc2nnc(-c3ccccc3)[nH]2)cc1C] | 1-(3,4-dimethylphenyl)-2-((5-phenyl-4H-1,2,4-triazol-3-yl)thio)ethan-1-one |
| 65 | 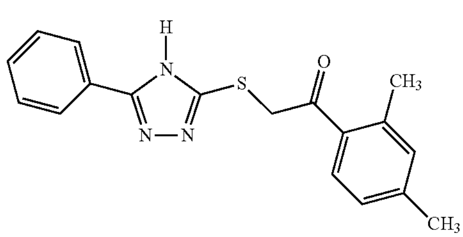 [SMILES: Cc1ccc(C(=O)CSc2nnc(-c3ccccc3)[nH]2)c(C)c1] | 1-(2,4-dimethylphenyl)-2-((5-phenyl-4H-1,2,4-triazol-3-yl)thio)ethan-1-one |

-continued

| Cmpd. No. | Structure | Compound Name |
|---|---|---|
| 66 | 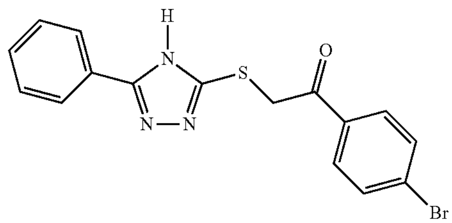 [SMILES: O=C(CSc1nnc(-c2ccccc2)[nH]1)c1ccc(Br)cc1] | 1-(4-bromophenyl)-2-((5-phenyl-4H-1,2,4-triazol-3-yl)thio)ethan-1-one |
| 67 | 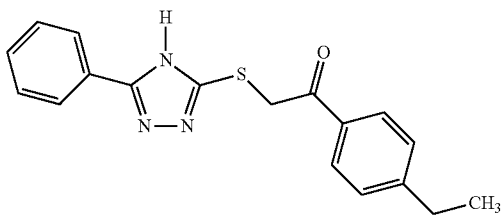 [SMILES: CCc1ccc(C(=O)CSc2nnc(-c3ccccc3)[nH]2)cc1] | 1-(4-ethylphenyl)-2-((5-phenyl-4H-1,2,4-triazol-3-yl)thio)ethan-1-one |
| 68 | 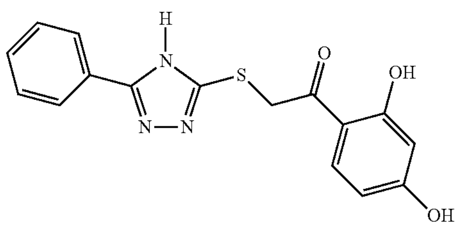 [SMILES: O=C(CSc1nnc(-c2ccccc2)[nH]1)c1ccc(O)cc1O] | 1-(2,4-dihydroxyphenyl)-2-((5-phenyl-4H-1,2,4-triazol-3-yl)thio)ethan-1-one |
| 69 | 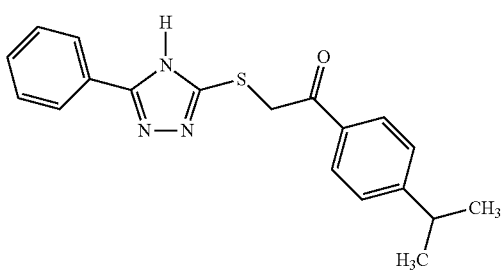 [SMILES: CC(C)c1ccc(C(=O)CSc2nnc(-c3ccccc3)[nH]2)cc1] | 1-(4-isopropylphenyl)-2-((5-phenyl-4H-1,2,4-triazol-3-yl)thio)ethan-1-one |
| 70 | 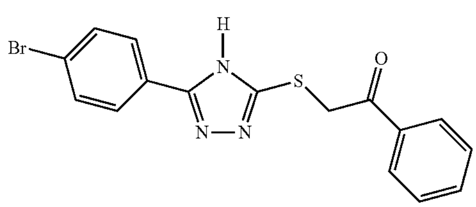 [SMILES: O=C(CSc1nnc(-c2ccc(Br)cc2)[nH]1)c1ccccc1] | 2-((5-(4-bromophenyl)-4H-1,2,4-triazol-3-yl)thio)-1-phenylethan-1-one |
| 71 | 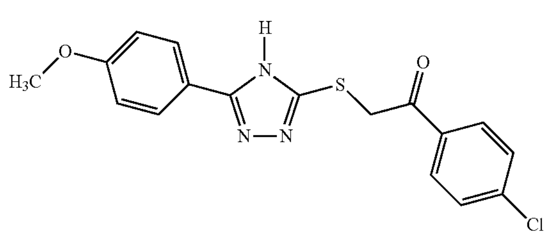 [SMILES: COc1ccc(-c2nnc(SCC(=O)c3ccc(Cl)cc3)[nH]2)cc1] | 1-(4-chlorophenyl)-2-((5-(4-methoxyphenyl)-4H-1,2,4-triazol-3-yl)thio)ethan-1-one |

-continued

| Cmpd. No. | Structure | Compound Name |
|---|---|---|
| 72 | 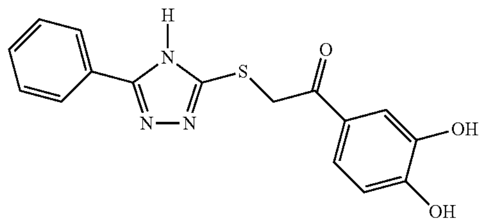 [SMILES: O=C(CSc1nnc(-c2ccccc2)[nH]1)c1ccc(O)c(O)c1] | 1-(3,4-dihydroxyphenyl)-2-((5-phenyl-4H-1,2,4-triazol-3-yl)thio)ethan-1-one |
| 73 | 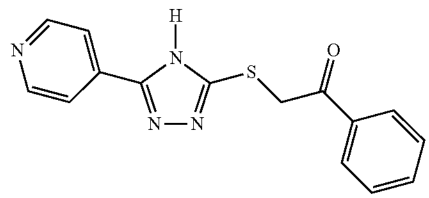 [SMILES: O=C(CSc1nnc(-c2ccncc2)[nH]1)c1ccccc1] | 1-phenyl-2-((5-(pyridin-4-yl)-4H-1,2,4-triazol-3-yl)thio)ethan-1-one |
| 74 | 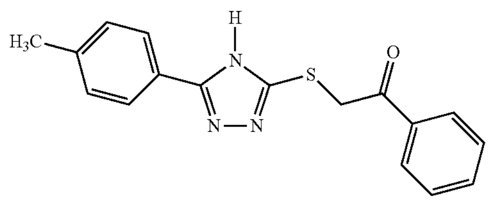 [SMILES: Cc1ccc(-c2nnc(SCC(=O)c3ccccc3)[nH]2)cc1] | 1-phenyl-2-((5-(p-tolyl)-4H-1,2,4-triazol-3-yl)thio)ethan-1-one |
| 75 | 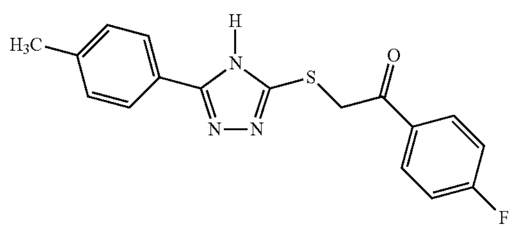 [SMILES: Cc1ccc(-c2nnc(SCC(=O)c3ccc(F)cc3)[nH]2)cc1] | 1-(4-fluorophenyl)-2-((5-(p-tolyl)-4H-1,2,4-triazol-3-yl)thio)ethan-1-one |
| 76 | 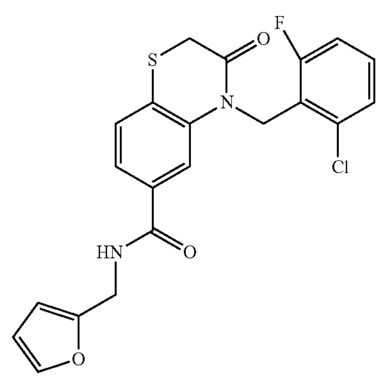 [SMILES: O=C(NCc1ccco1)c1ccc2c(c1)N(Cc1c(F)cccc1Cl)C(=O)CS2] | 4-(2-chloro-6-fluorobenzyl)-N-(furan-2-ylmethyl)-3-oxo-3,4-dihydro-2H-benzo[b][1,4]thiazine-6-carboxamide |
| 77 | 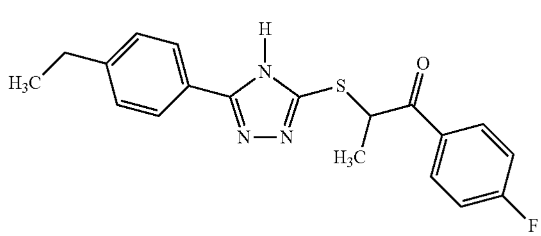 [SMILES: CCc1ccc(-c2nnc(SC(C)C(=O)c3ccc(F)cc3)[nH]2)cc1] | 2-((5-(4-ethylphenyl)-4H-1,2,4-triazol-3-yl)thio)-1-(4-fluorophenyl)propan-1-one |

-continued

| Cmpd. No. | Structure | Compound Name |
|---|---|---|
| 78 | 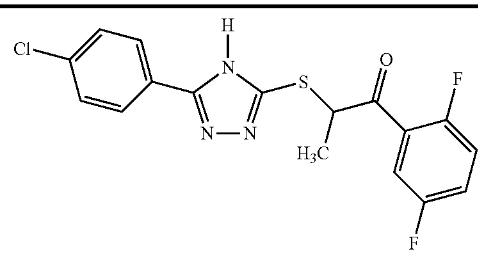 | 2-((5-(4-chlorophenyl)-4H-1,2,4-triazol-3-yl)thio)-1-(2,5-difluorophenyl)propan-1-one |
| 79 | 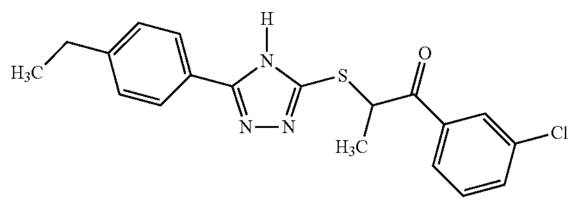 [SMILES: CCc1ccc(-c2nnc(SC(C)C(=O)c3cccc(Cl)c3)[nH]2)cc1] | 1-(3-chlorophenyl)-2-((5-(4-ehtylphenyl)-4H-1,2,4-triazol-3-yl)thio)propan-1-one |
| 80 | 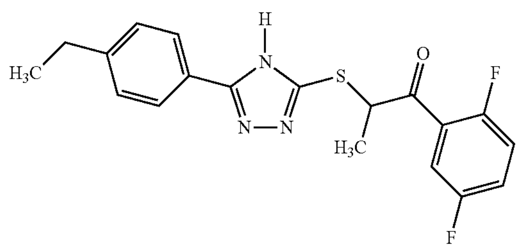 [SMILES: CCc1ccc(-c2nnc(SC(C)C(=O)c3cc(F)ccc3F)[nH]2)cc1] | 1-(2,5-difluorophenyl)-2-((5-(4-ethylphenyl)-4H-1,2,4-triazol-3-yl)thio)propan-1-one |
| 81 | 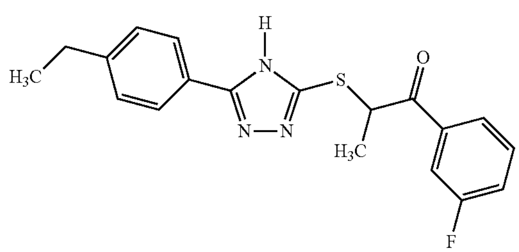 [SMILES: CCc1ccc(-c2nnc(SC(C)C(=O)c3cccc(F)c3)[nH]2)cc1] | 2-((5-(4-ethylphenyl)-4H-1,2,4-triazol-3-yl)thio)-1-(3-fluorophenyl)propan-1-one |
| 82 | 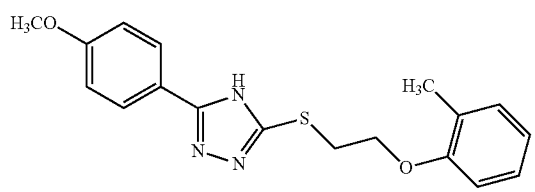 [SMILES: COc1ccc(-c2nnc(SCCOc3ccccc3C)[nH]2)cc1] | 3-(4-methoxyphenyl)-5-((2-(o-tolyloxy)ethyl)thio)-4H-1,2,4-triazole |
| 83 | 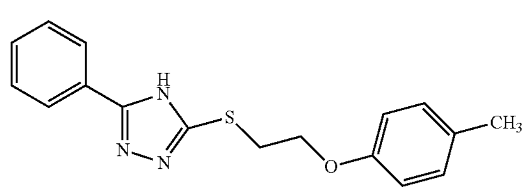 [SMILES: Cc1ccc(OCCSc2nnc(-c3ccccc3)[nH]2)cc1] | 3-phenyl-5-((2-(p-tolyoxy)ethyl)thio)-4H-1,2,4-triazole |
| 84 | 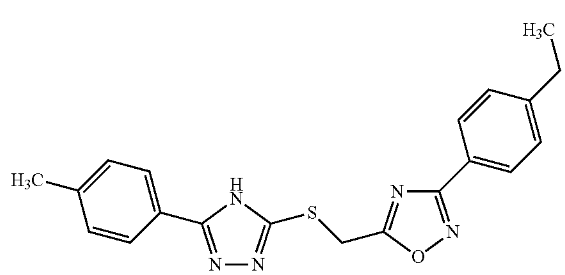 [SMILES: CCc1ccc(-c2noc(CSc3nnc(-c4ccc(C)cc4)[nH]3)n2)cc1] | 3-(4-ethylphenyl)-5-(((5-(p-tolyl)-4H-1,2,4-triazol-3-yl)thio)methyl)-1,2,4-oxadiazole |

| Cmpd. No. | Structure | Compound Name |
|---|---|---|
| 85 | 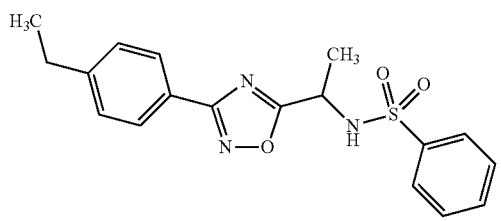 [SMILES: CCc1ccc(-c2noc(C(C)NS(=O)(=O)c3ccccc3)n2)cc1] | N-(1-(3-(4-ethylphenyl)-1,2,4-oxadiazol-5-yl)ethyl)benzenesulfonamide |
| 86 | 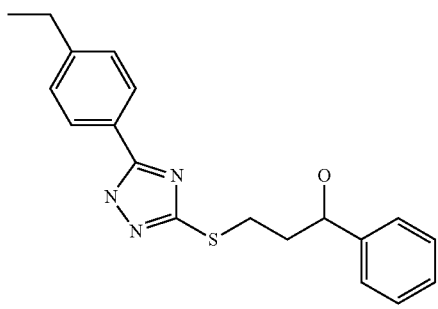 [SMILES: CCc1ccc(-c2nc(SCCC(O)c3ccccc3)n[nH]2)cc1] | 3-{[5-(4-ethylphenyl)-4H-1,2,4-triazol-3-yl]sulfanyl}-1-phenylpropan-1-ol |
| 87 | 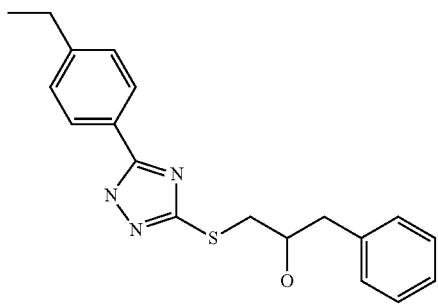 [SMILES: CCc1ccc(-c2nc(SCC(O)Cc3ccccc3)n[nH]2)cc1] | 1-{[5-(4-ethylphenyl)-4H-1,2,4-triazol-3-yl]sulfanyl}-3-phenylpropan-2-ol |
| 88 | 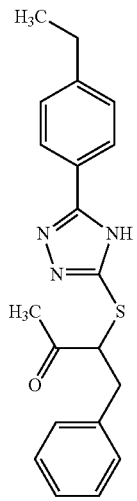 [SMILES: CCc1ccc(-c2nnc(SC(Cc3ccccc3)C(C)=O)[nH]2)cc1] | 3-((5-(4-ethylphenyl)-4H-1,2,4-triazol-3-yl)thio)-4-phenylbutan-2-one |

-continued

| Cmpd. No. | Structure | Compound Name |
|---|---|---|
| 89 | 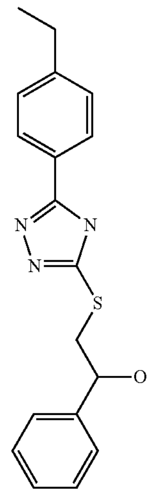 [SMILES: CCc1ccc(-c2nnc(SCC(O)c3ccccc3)[nH]2)cc1] | 2-{[5-(4-ethylphenyl)-4H-1,2,4-triazol-3-yl)sulfanyl}-1-phenylethan-1-ol |
| 90 | 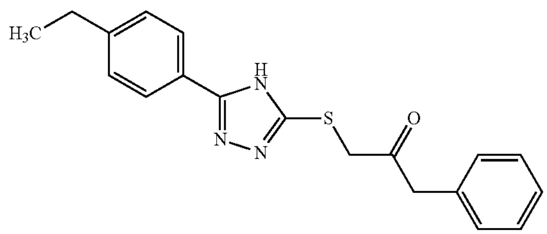 [SMILES: CCc1ccc(-c2nnc(SCC(=O)Cc3ccccc3)[nH]2)cc1] | 1-((5-(4-ethylphenyl)-4H-1,2,4-triazol-3-yl)thio)-3-phenylpropan-2-one |
| 91 | 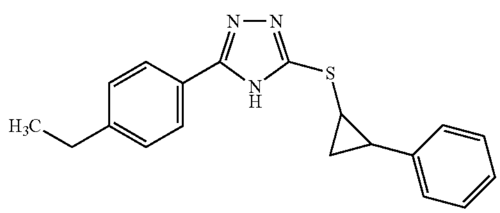 [SMILES: CCc1ccc(-c2nnc(SC3CC3c3ccccc3)[nH]2)cc1] | 3-(4-ethylphenyl)-5-((2-phenylcyclopropyl)thio)-4H-1,2,4-triazole |
| 92 | 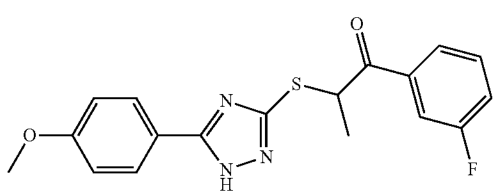 [SMILES: COc1ccc(-c2nc(SC(C)C(=O)c3cccc(F)c3)n[nH]2)cc1] | 1-(3-fluorophenyl)-2-{[5-(4-methoxyphenyl)-1H-1,2,4-triazol-3-yl]sulfanyl}propan-1-one |
| 93 | 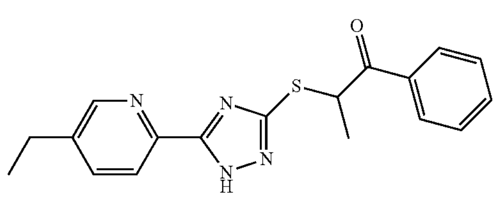 [SMILES: CCc1ccc(-c2nc(SC(C)C(=O)c3ccccc3)n[nH]2)nc1] | 2-{[5-(5-ethylpyridin-2-yl)-1H-1,2,4-triazol-3-yl]sulfanyl}-1-phenylpropan-1-one |
| 94 | 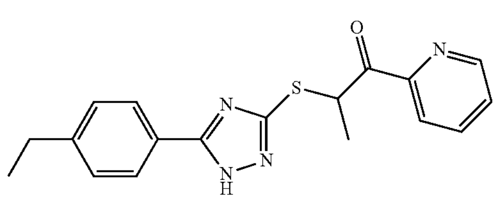 [SMILES: CCc1ccc(-c2nc(SC(C)C(=O)c3ccccn3)n[nH]2)cc1] | 2-{[5-(4-ethylphenyl)-1H-1,2,4-triazol-3-yl]sulfanyl}-1-(pyridin-2-yl)propan-1-one |

-continued

| Cmpd. No. | Structure | Compound Name |
|---|---|---|
| 95 | 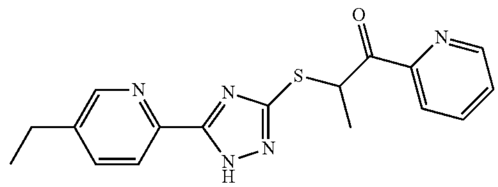 [SMILES: CCc1ccc(-c2nc(SC(C)C(=O)c3ccccn3)n[nH]2)nc1] | 2-{[5-(5-ethylpyridin-2-yl)-1H-1,2,4-triazol-3-yl]sulfanyl}-1-(pyridin-2-yl)propan-1-one |
| 96 | CF: $C_{18}H_{16}FN_3O_3S_2$<br>MW: 405.46 | 1-(3-fluorophenyl)-2-{[5-(4-methanesulfonylphenyl)-1H-1,2,4-triazol-3-yl]sulfanyl}propan-1-one |
| 97 | CF: $C_{16}H_{13}FN_4OS$<br>MW: 328.37 | 1-(3-fluorophenyl)-2-{[5-(pyridin-4-yl)-1H-1,2,4-triazol-3-yl]sulfanyl}propan-1-one |
| 98 | CF: $C_{16}H_{18}FN_4OS$<br>MW: 338.43 | 1-(4-ethylphenyl)-2-{[5-(pyridin-4-yl)-1H-1,2,4-triazol-3-yl]sulfanyl}propan-1-one |
| 99 | CF: $C_{20}H_{20}FN_3OS$<br>MW: 369.46 | 2-{[5-(4-ethylphenyl)-4-methyl-4H-1,2,4-triazol-3-yl]sulfanyl}-1-(3-fluorophenyl)propan-1-one |

-continued

| Cmpd. No. | Structure | Compound Name |
|---|---|---|
| 100 | CF: $C_{19}H_{18}FN_3O_3S$<br>MW: 387.43 | 2-{[5-(4-ethylphenyl)-4H-1,2,4-triazol-3-yl]sulfonyl}-1-(3-fluorophenyl)propan-1-one |
| 101 | CF: $C_{19}H_{18}FN_3OS$<br>MW: 355.43 | 2-{[5-(4-ethylphenyl)-4H-1,2,4-triazol-3-yl]sulfanyl}-1-(3-fluorophenyl)propan-1-one |
| 102 | CF: $C_{19}H_{18}N_4O_3S$<br>MW: 382.44 | 2-{[5-(4-ethylphenyl)-4H-1,2,4-triazol-3-yl]sulfanyl}-1-(3-nitrophenyl)propan-1-one |
| 103 | Chemical Formula: $C_{19}H_{20}N_4OS$<br>Molecular Weight: 352.46 | 1-(3-aminophenyl)-2-{[5-(4-ethylphenyl)-4H-1,2,4-triazol-3-yl]sulfanyl}propan-1-one |
| 104 | CF: $C_{21}H_{24}N_4O_5S_3$<br>MW: 508.63 | N-[3-(2-{[5-(4-ethylphenyl)-4-methanesulfonyl-4H-1,2,4-triazol-3-yl]sulfanyl}propanoyl)phenyl]methanesulfonamide |

| Cmpd. No. | Structure | Compound Name |
|---|---|---|
| 105 | (structure shown) CF: $C_{20}H_{22}N_4O_3S_2$ MW: 430.54 | N-[3-(2-{[5-(4-ethylphenyl)-4H-1,2,4-triazol-3-yl]sulfanyl}propanoyl)phenyl]methanesulfonamide |
| 106 | (structure shown) Molecular Weight: 356.42 | 2-{[5-(6-ethylpyridin-3-yl)-4H-1,2,4-triazol-3-yl]sulfanyl}-1-(3-fluorophenyl)propan-1-one |

Table II shows the luciferase induction activity and solubility of non-limiting illustrative examples of compounds.

| Compound. | Activity (Fold changes of IFNβ promoter activity at 50 µM) | Solubility |
|---|---|---|
| 28 | 8 fold induction (FIGS. 2A, 3A) | <31 µM in PBS |
| 77 | 10.0 fold induction (FIG. 3A) | <2 µM in PBS |
| 78 | 6.0 fold induction (FIG. 3A) | |
| 79 | 5.5 fold induction (FIG. 3A) | |
| 80 | 6.0 fold induction (FIG. 3A) | <2 µM in PBS |
| 81 | 5.0 fold induction (FIGS. 2A, 3A) | <2 µM in PBS |
| 85 | 4.0 fold induction (FIG. 3B) | |
| 86 | 1.0 fold induction (FIG. 3B) | |
| 87 | 1.5 fold induction (FIG. 3B) | |
| 88 | 7.5 fold induction (FIG. 3B) | <2 µM in PBS |
| 89 | 1.0 fold induction (FIG. 3B) | <12 µM in PBS |
| 90 | 1.0 fold induction (FIG. 3B) | |
| 91 | 4.0 fold induction (FIG. 3B) | |
| 92 | 1.0 fold induction (FIG. 2A) | LogS −7.24 |
| 93 | 1.0 fold induction (FIG. 2A) | LogS −6.25 |
| 94 | 1.0 fold induction (FIG. 2A) | LogS −6.95 |
| 95 | 1.0 fold induction (FIG. 2A) | LogS −5.42 |
| 96 | 1.0 fold induction (FIG. 2B) | |
| 97 | 1.0 fold induction (FIG. 2B) | |
| 98 | 1.0 fold induction (FIG. 2B) | |
| 99 | 1.0 fold induction (FIG. 2B) | |
| 100 | 1.0 fold induction (FIG. 2B) | |
| 101 | 4.5 fold induction (FIG. 2B) | |
| 102 | 1.0 fold induction (FIG. 2C) | |
| 103 | 1.0 fold induction (FIG. 2C) | |
| 104 | 1.0 fold induction (FIG. 2C) | |
| 105 | 1.0 fold induction (FIG. 2C) | |
| 106 | 1.0 fold induction (FIG. 2C) | |

Compounds of the present invention were examined for their ability to activate the type I interferon (IFN) promoter, using a live cell assay. This assay comprised immortalized human fibroblasts (hTERT) that were stably transfected with the type I IFN promoter driving luciferase as well as the CMV promoter driving SEAP (hTERT-pIFNβ-Glu), as described in PCT Application No. PCT/US2019/025380, inventor Glen N. Barber, published as WO2019195285, which is herein incorporated by reference in its entirety and for all purposes. The ability of the small molecules to activate the type I IFN promoter and the transcription of luciferase, but not SEAP was assessed. That is, the activation of STING, typically by CDNs, in turn activates the transcription factors NF-κB and IRF3, both of which are required to induce the transcriptional stimulation of the Type I IFN promoter, but not the CMV promoter (IRF3 and NF-kB transcription factor binding sites are not contained in the CMV promoter). Thus, should STING be activated by a small molecule identified in the first screen (HTS), the level of luciferase should increase relative to SEAP production. Compound 101 identified in a second screen exhibited the ability to activate the type I IFN promoter in hTERT-pIFNβ-Glu and induce the expression of luciferase but not SEAP (see FIG. 2B).

Figure 2A:
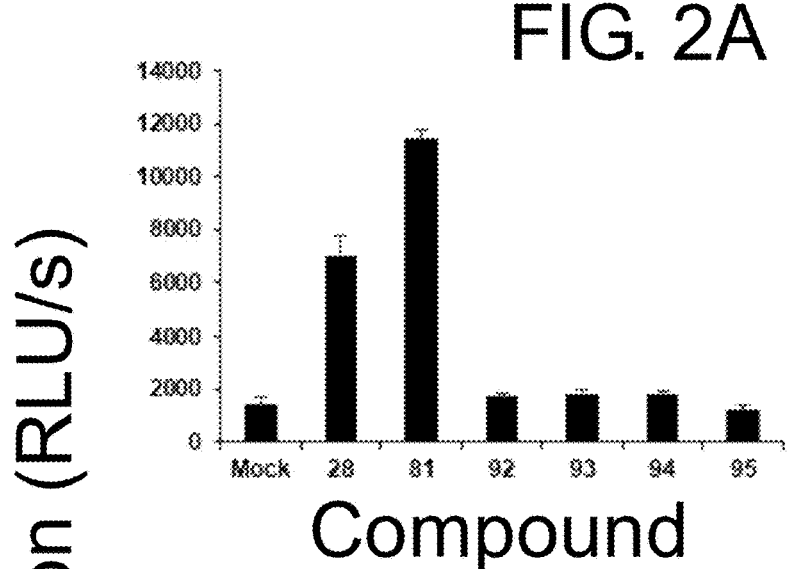
FIG. 2A shows luciferase induction activity of Compounds 92, 93, 94, 95, 28 and 81 at concentrations of 50 µM.
Figure 2B:
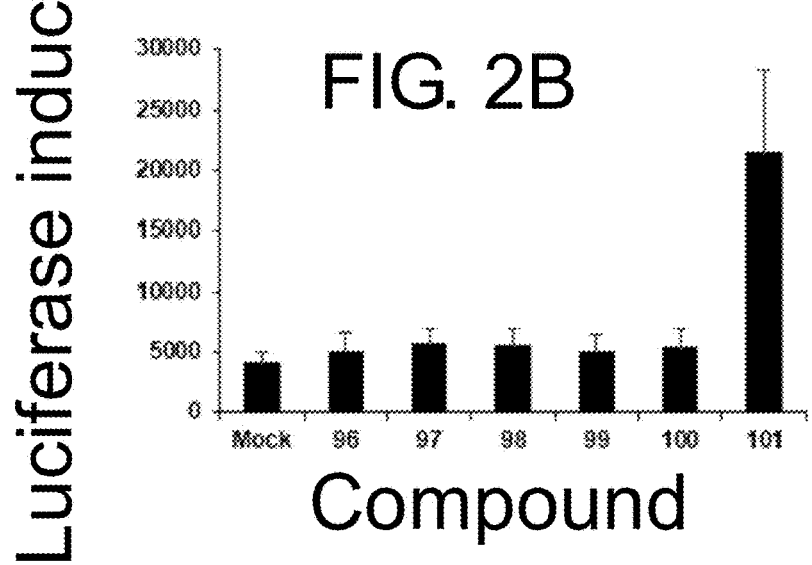
FIG. 2B shows luciferase induction activity of Compounds 96, 97, 98, 99, 100 and 101 at concentrations of 50 µM.
Figure 2C:
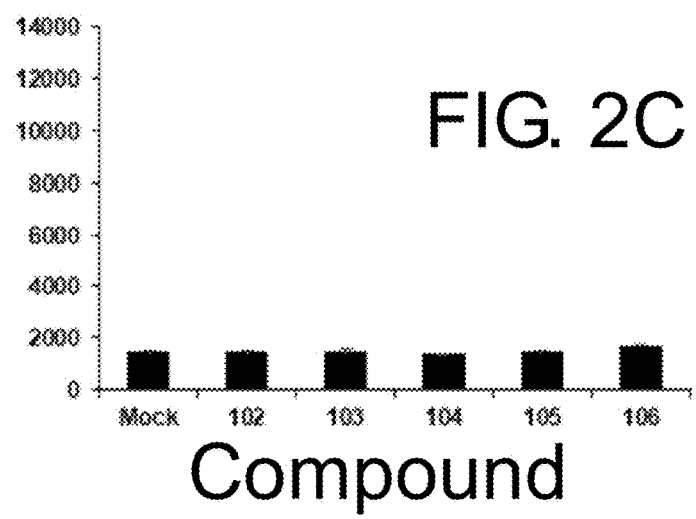
FIG. 2C shows luciferase induction activity of Compounds 102, 103, 104, 105 and 106 at concentrations of 50 µM.
Figure 3A:
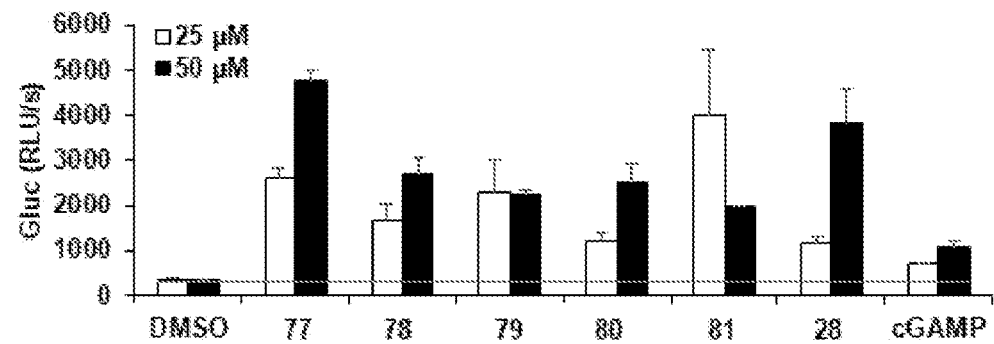
FIG. 3A shows luciferase induction activity of Compounds 77, 78, 79, 80, 81, 28, and cGAMP at concentrations of 25 µM and 50 µM.
Figure 3B:
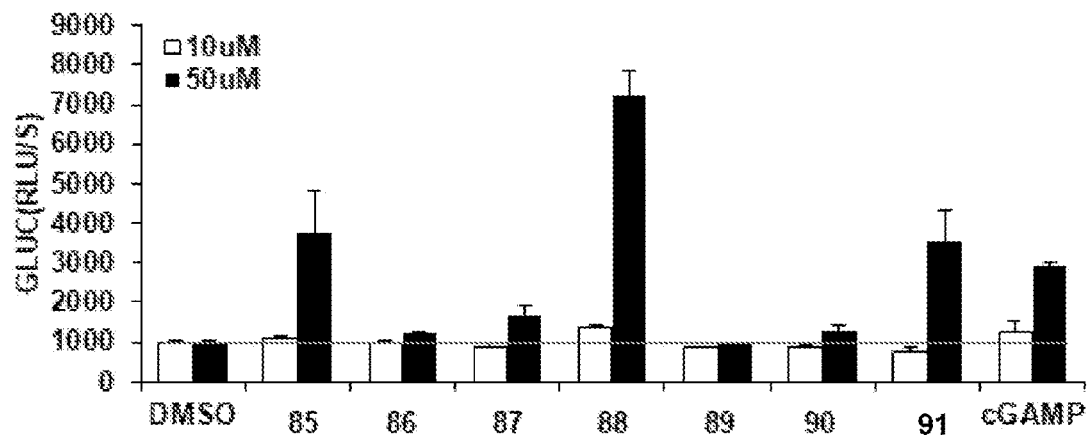
FIG. 3B shows activity of Compounds 85, 86, 87, 88, 89, 90, 91, and cGAMP at concentrations of 10 µM and 50 µM.
Figure 3C:
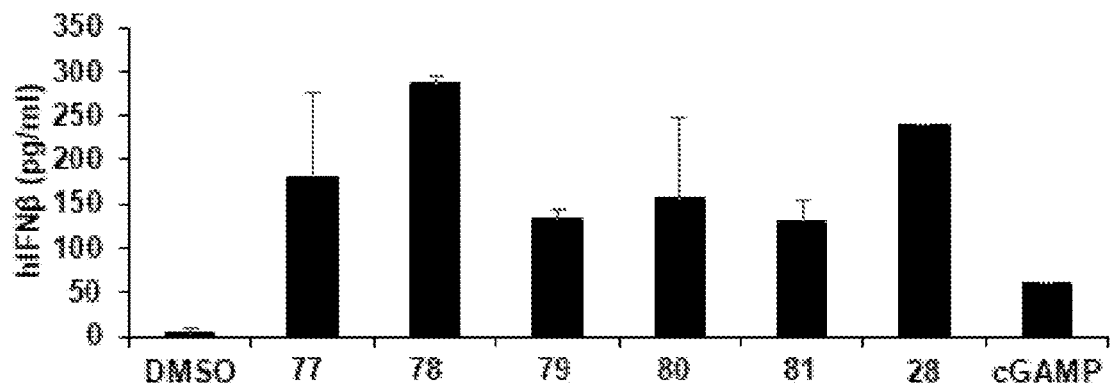
FIG. 3C shows activity of Compounds 77, 78, 79, 80, 81, 28, and cGAMP at a concentration of 50 µM.
Figure 3D:
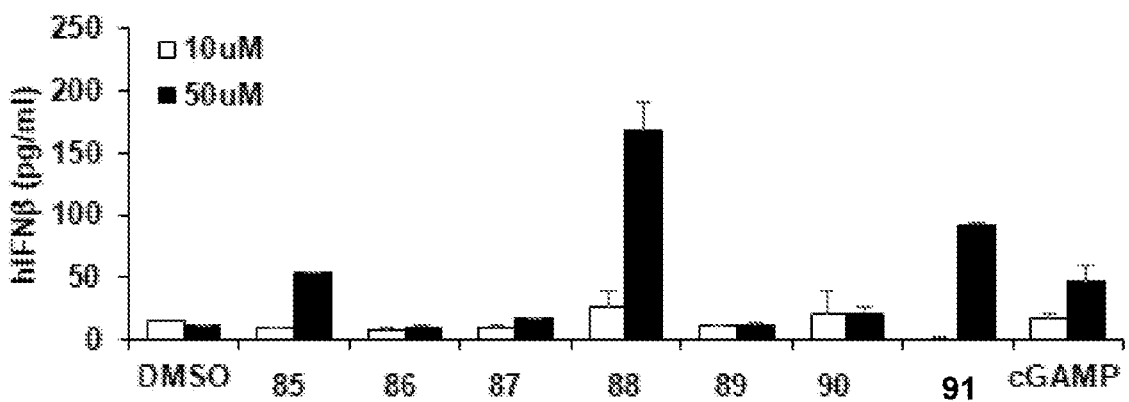
FIG. 3D shows activity of compounds 85, 86, 87, 88, 89, 90, 91, and cGAMP at concentrations of 10 µM and 50 µM.

FIGS. 2A-C show luciferase induction activity of compounds 81-106 at concentrations of 50 µM. Compounds (in 0.5% DMSO) were placed onto hTERT-pIFNβ-Glu cells for approximately 24 hours and luciferase induction was measured. FIG. 3A shows luciferase induction activity of Compounds 28, 77, 78, 79, 80, 81, and cGAMP at concentrations of 25 µM and 50 µM. FIG. 3B show luciferase induction activity of Compounds 85, 86, 87, 88, 89, 90, 91, and cGAMP at concentrations of 10 µM and 50 µM. In FIGS. 3A-B Compounds (in 0.5% DMSO) were placed onto hTERT-pIFNβ-Glu cells for approximately 12 hours and luciferase measured. FIG. 3C shows activity of compounds 28, 77, 78, 79, 80, 81, and cGAMP at concentrations of 50 µM. FIG. 3D shows activity of compounds 85, 86, 87, 88, 89, 90, 91, and cGAMP at concentrations of 10 µM and 50 µM. In FIGS. 3C-D Compounds (in 0.5% DMSO) were placed onto hTERT cells for approximately 12 hours or type I IFN was measured. Solubility was determined using proprietary software, e.g., http://www.researchgate.net/publication/12055195_Internet_Software_for_the_Calculation_of_the_Lipophilicity_and_Aqueous_Solubility_of_Chemical_Compounds, last visited Dec. 16, 2020).

Some of the foregoing compounds can comprise one or more asymmetric centers, and thus can exist in various isomeric forms, e.g., stereoisomers and/or diastereomers. Accordingly, compounds of the application can be in the form of an individual enantiomer, diastereomer or geometric isomer, or can be in the form of a mixture of stereoisomers. In one embodiment, the compounds of the application are enantiopure compounds. In another embodiment, mixtures of stereoisomers or diastereomers are provided.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{18}F$, $^{35}S$, $^{32}P$, $^{125}I$, and $^{131}I$) introduced into the compound. Such compounds are useful for drug metabolism studies and diagnostics, as well as therapeutic applications.

Potency can also be determined by $IC_{50}$ value. A compound with a lower $IC_{50}$ value, as determined under substantially similar conditions, is more potent relative to a compound with a higher $IC_{50}$ value. In an embodiment of the present invention, the substantially similar conditions comprise determining the level of binding of a known STING ligand to a STING protein, in vitro or in vivo, in the presence of a compound of the application.

In an embodiment of the present invention, the compounds of the present application are useful as therapeutic agents, and thus can be useful in the treatment of a disease caused by, or associated with, STING expression, activity, and/or function (e.g., deregulation of STING expression, activity, and/or function) or a disease associated with one or more of the intracellular pathways that STING is involved in (e.g. regulation of intracellular DNA-mediated type I interferon activation), such as those described herein.

A "selective STING modulator" can be identified, for example, by comparing the ability of a compound to modulate STING expression/activity/function to its ability to modulate the other proteins or a STING protein from another species. In an embodiment of the present invention, the selectivity can be identified by measuring the $EC_{50}$ or $IC_{50}$ of the compounds.

In certain embodiments, the compounds of the application are STING modulators that exhibit at least 2-fold, 3-fold, 5-fold, 10-fold, 25-fold, 50-fold or 100-fold selectivity over other proteins or a STING protein from another species. In various embodiments, the compounds of the application exhibit 1000-fold selectivity over other proteins or a STING protein from another species.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

In another aspect, the application provides a method of synthesizing a compound disclosed herein. The synthesis of the compounds of the application can be found herein and in the Examples below. Other embodiments are a method of making a compound of any of the formulae herein using any one, or combination of, reactions delineated herein. The method can include the use of one or more intermediates or chemical reagents delineated herein.

The application also provides for a pharmaceutical composition including a therapeutically effective amount of a compound of the application, or a pharmaceutically acceptable salt or ester thereof, and a pharmaceutically acceptable carrier.

In an embodiment of the invention, a kit for treating or preventing a disease in a mammal comprises a compound of the application or a pharmaceutically acceptable salt or ester thereof, or a pharmaceutical composition of the application with instructions for the use thereof for reducing metastasis and neoplastic growth in a mammal. In another embodiment of the invention, the application provides a kit including a compound capable of modulating STING activity selected from one or more compounds disclosed herein, or a pharmaceutically acceptable salt or ester thereof, optionally in combination with a second agent with instructions for the use thereof for reducing metastasis and neoplastic growth in a mammal.

In an embodiment of the present invention, a compound of the application or a pharmaceutically acceptable salt or ester thereof, or a pharmaceutical composition of the application, is used in the manufacture of a medicament for stimulating a STING protein, for treating or preventing a disease, where the diseases is caused by, or associated with, STING expression, activity, and/or function (e.g., deregulation of STING expression, activity, and/or function), or for treating or preventing a disease associated with deregulation of one or more of the intracellular pathways in which a STING protein is involved (e.g., deregulation of intracellular dsDNA mediated type I interferon activation.

In an embodiment of the present invention, a compound of Table II of the application or a pharmaceutically acceptable salt or ester thereof, or a pharmaceutical composition of Table II of the application, is used in the manufacture of a medicament for stimulating a STING protein, for treating or preventing a disease, where the diseases is caused by, or associated with, STING expression, activity, and/or function (e.g., deregulation of STING expression, activity, and/or function), or for treating or preventing a disease associated with deregulation of one or more of the intracellular pathways in which a STING protein is involved (e.g., deregulation of intracellular dsDNA mediated type I interferon activation).

In an embodiment of the present invention, a compound of Table II of the application or a pharmaceutically acceptable salt or ester thereof, or a pharmaceutical composition of the application, is used in stimulating a STING protein, in treating or preventing a disease, where the diseases is caused by, or associated with, STING expression, activity, and/or function (e.g., deregulation of STING expression, activity, and/or function), or in treating or preventing a disease associated with deregulation of one or more of the intracellular pathways in which a STING protein is involved (e.g., deregulation of intracellular dsDNA mediated type I interferon activation).

In an embodiment of the present invention, a compound of Table II of the application or a pharmaceutically acceptable salt or ester thereof, or a pharmaceutical composition of the application is used, in stimulating a STING protein, in treating or preventing a disease, where the diseases is caused by, or associated with, STING expression, activity, and/or function (e.g., deregulation of STING expression, activity, and/or function), or in treating or preventing a disease associated with deregulation of one or more of the intracellular pathways in which a STING protein is involved (e.g., deregulation of intracellular dsDNA mediated type I interferon activation).

Method of Synthesizing the Compounds

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application. The processes generally provide the desired final compound at or near the end of the overall process, although it can be desirable in certain instances to further convert the compound to a pharmaceutically acceptable salt, ester, or prodrug thereof. Suitable synthetic routes are depicted in the schemes below.

Example X: Synthesis of X

Those skilled in the art will recognize if a stereocenter exists in the compounds disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it can be obtained by stereospecific synthesis or by resolution of the final product or any convenient intermediate. Resolution of the final product, an intermediate, or a starting material can be affected by any suitable method known in the art. See, for example, "Stereochemistry of Organic Compounds" by E. L. Eliel, S. H. Wilen, and L. N. Mander (Wiley-Interscience, 1994) which is herein expressly incorporated by reference.

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below.

Compounds of the present application can be synthesized by following the steps outlined in the following Schemes, which comprise different sequences of assembling intermediates. Starting materials are either commercially available or made by known procedures in the reported literature or as illustrated. As shown in the Schemes below A compound of the application can be prepared as a pharmaceutically acceptable acid addition salt by reacting the free base form of the compound with a pharmaceutically acceptable inorganic or organic acid. Alternatively, a pharmaceutically acceptable base addition salt of a compound of the application can be prepared by reacting the free acid form of the compound with a pharmaceutically acceptable inorganic or organic base. The pharmaceutically acceptable salt can include various counterions, e.g., counterions of the inorganic or organic acid, counterions of the inorganic or organic base, or counterions afforded by counterion exchange.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alternatively, the salt forms of the compounds of the application can be prepared using salts of the starting materials or intermediates. The free acid or free base forms of the compounds of the application can be prepared from the corresponding base addition salt or acid addition salt from, respectively. For example, a compound of the application in an acid addition salt form can be converted to the corresponding free base by treating with a suitable base (e.g., ammonium hydroxide solution, sodium hydroxide, and the like). A compound of the application in a base addition salt form can be converted to the corresponding free acid by treating with a suitable acid (e.g., hydrochloric acid, etc.).

Compounds of the present application that contain nitrogens can be converted to N-oxides by treatment with an oxidizing agent (e.g., 3-chloroperoxybenzoic acid (m-CPBA) and/or hydrogen peroxides) to afford other compounds of the present application. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the present application can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, where R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

Prodrugs of the compounds of the application can be prepared by methods known to those of ordinary skill in the art (e.g., for further details see Saulnier et al., (1994), Bioorganic and Medicinal Chemistry Letters, Vol. 4, p. 1985 each of which are herein expressly incorporated by reference). For example, appropriate prodrugs can be prepared by reacting a non-derivatized compound of the application with a suitable carbamylating agent (e.g., 1,1-acyloxyalkylcarbanochloridate, para-nitrophenyl carbonate, or the like). Specifically, the central N-acetic acid moeity, and other analogous carboxylic acid groups, of the compounds of the present invention can be modified through techniques known in the art to produce effective prodrugs of the present invention.

Protected derivatives of the compounds of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999 which is herein expressly incorporated by reference.

Compounds of the present application can be conveniently prepared, or formed during the process of the application, as solvates (e.g., hydrates). Hydrates of compounds of the present application can be conveniently prepared by recrystallization from an aqueous/organic solvent mixture, using organic solvents such as dioxin, tetrahydrofuran or methanol.

Optical isomers can be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981) which is herein expressly incorporated by reference.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps can be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof, each of which are herein expressly incorporated by reference.

The compounds of this application can be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Biological Assays

Biological activities of the compounds of the present application can be measured by various biochemical or cellular assays known to one of ordinary skill in the art. Non-limiting examples of biochemical and cellular assays are listed in the Examples discussed below.

Pharmaceutical Compositions

In another aspect, a pharmaceutical composition is provided. The pharmaceutical composition comprises a therapeutically effective amount of a compound of the application, or a pharmaceutically acceptable salt or ester thereof, and a pharmaceutically acceptable carrier.

Compounds of the application can be administered as pharmaceutical compositions by any conventional route, in particular internally, e.g., orally, e.g., in the form of tablets or capsules, or parenterally, e.g., in the form of injectable solutions or suspensions, or topically, e.g., in the form of lotions, gels, ointments or creams, or in a nasal or suppository form.

Pharmaceutical compositions including a compound of the present application in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules including the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. Suitable formulations for transdermal applications include an effective amount of a compound of the present application with a carrier. A carrier can include absorbable pharmacologically acceptable solvents to assist passage through the skin of the host. For example, transdermal devices can be in the form of a bandage including a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations can also be used. Suitable formulations for topical application, e.g., to the skin and eyes, are preferably aqueous solutions, ointments, creams or gels well-known in the art. Such solutions, ointments, creams or gels can contain solubilizers, stabilizers, tonicity enhancing agents, buffers and preservatives.

The pharmaceutical compositions of the present application comprise a therapeutically effective amount of a compound of the present application formulated together with one or more pharmaceutically acceptable carriers. As used herein, the term "pharmaceutically acceptable carrier"

means a non-toxic, inert solid, semi-solid or liquid filler, diluent, encapsulating material or formulation auxiliary of any type. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxy propylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this application can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration can include pharmaceutically acceptable emulsions, microemulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous, or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type can also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose. In the case of capsules, tablets and pills, the dosage forms can also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels can contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For any compound, the therapeutically effective amount can be estimated initially either in cell culture assays, e.g., of neoplastic cells, or in animal models, usually rats, mice, rabbits, dogs, or pigs. The animal model can also be used to determine the appropriate concentration range and route of administration. Such information can then be used to determine useful doses and routes for administration in humans. Therapeutic/prophylactic efficacy and toxicity can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage can vary within this range depending upon the dosage form employed, sensitivity of the patient, and the route of administration.

Dosage and administration are adjusted to provide sufficient levels of the active agent(s) or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on half-life and clearance rate of the particular formulation.

The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

The pharmaceutical compositions containing active compounds of the present application can be manufactured in a manner that is generally known, e.g., by means of conventional mixing, dissolving, granulating, dragee-making, levigating, emulsifying, encapsulating, entrapping, or lyophilizing processes. Pharmaceutical compositions can be formulated in a conventional manner using one or more pharmaceutically acceptable carriers including excipients and/or auxiliaries that facilitate processing of the active compounds into preparations that can be used pharmaceutically. Of course, the appropriate formulation is dependent upon the route of administration chosen.

Techniques for formulation and administration of the disclosed compounds of the application can be found in *Remington: the Science and Practice of Pharmacy*, 19$^{th}$ edition, Mack Publishing Co., Easton, PA (1995) which is herein expressly incorporated by reference. In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

Methods of Use

In one aspect, the present application provides a method of stimulating a STING protein. The present application preferably provides a method of stimulating a STING protein. The method comprises administering to a subject in need thereof an effective amount of a compound of the application or a pharmaceutically acceptable salt or ester thereof, or a pharmaceutical composition of the application.

In an embodiment of the present invention, the modulation of a STING protein activity is measured by $IC_{50}$. In an embodiment of the present invention, the modulation of a STING protein activity is measured by $EC_{50}$.

A compound of the present application (e.g., a compound of any of the formulae described herein, or selected from any compounds described herein) is capable of treating or preventing a disease, where the diseases is caused by, or associated with, STING expression, activity, and/or function (e.g. deregulation of STING expression, activity, and/or function) or a disease associated with deregulation of one or more of the intracellular pathways in which a STING protein is involved (e.g., deregulation of intracellular dsDNA mediated type I interferon activation).

In an embodiment of the present application, a method of treating or preventing a disease, where the diseases is caused by, or associated with, STING expression, activity, and/or function (e.g., deregulation of STING expression, activity, and/or function) comprises administering to a subject in need thereof an effective amount of a compound of the application or a pharmaceutically acceptable salt or ester thereof, or a pharmaceutical composition of the application. In one aspect, the disease is a STING mediated disorder.

In an embodiment of the present application, a method of treating or preventing a disease associated with deregulation of one or more of the intracellular pathways in which a STING protein is involved (e.g., deregulation of intracellular dsDNA mediated type I interferon activation) comprises administering to a subject in need thereof an effective amount of a compound of the application or a pharmaceutically acceptable salt or ester thereof, or a pharmaceutical composition of the application.

In an embodiment of the present application, a method of treating or preventing any of the diseases, disorders, and conditions described herein, where the subject is a human provides a method of treatment. In an alternative embodiment, a method of prevention is provided.

As modulators of a STING protein, the compounds and compositions of this application are particularly useful for treating or lessening the severity of a disease, condition, or disorder where a STING protein or one or more of the intracellular pathways that STING is involved is implicated in the disease, condition, or disorder. In one embodiment, the present application provides a method for treating or lessening the severity of a disease, condition, or disorder with compounds that modulate binding of a non-canonical cyclic di-nucleotide (CDN), such as 2'3'cGAMP, to a STING protein. In one embodiment, the present application provides a method for treating or lessening the severity of a disease, condition, or disorder with compounds that modulate the synthesis of type I interferon and/or type I IFN response.

In one aspect, the present application also provides a method of treating or preventing cell proliferative disorders such as hyperplasias, dysplasias, or pre-cancerous lesions. Dysplasia is the earliest form of pre-cancerous lesion recognizable in a biopsy by a pathologist. The compounds of the present application can be administered for the purpose of preventing hyperplasias, dysplasias, or pre-cancerous lesions from continuing to expand or from becoming cancerous. Examples of pre-cancerous lesions can occur in skin, esophageal tissue, breast, and cervical intra-epithelial tissue.

In one embodiment, the disease or disorder includes, but is not limited to, immune disorders, autoimmunity, a cell proliferative disease or disorder, cancer, inflammation, cachexia, neurodegenerative disease or disorders, neurological diseases or disorders, cardiac dysfunction, transplantation, or infection (e.g., viral, bacterial, and/or fungi infection, or infection caused by other microorganism).

In one embodiment, the disease or disorder is a cell proliferative disease or disorder.

As used herein, the term "cell proliferative disorder" refers to conditions in which unregulated or abnormal growth, or both, of cells can lead to the development of an unwanted condition or disease, which may or may not be cancerous. Exemplary cell proliferative diseases or disorders encompass a variety of conditions where cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disease or disorder includes a precancer or a precancerous condition. A cell proliferative disease or disorder includes cancer.

In one embodiment, the proliferative disease or disorder is a non-cancerous. In one embodiment, the non-cancerous disease or disorder includes, but is not limited to, rheumatoid arthritis; inflammation; autoimmune disease; lymphoproliferative conditions; acromegaly; rheumatoid spondylitis; osteoarthritis; gout; other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; skin-related hyperproliferative disorders; psoriasis; eczema; atopic dermatitis; hyperpigmentation disorders; eye-related hyperproliferative disorders; age-related macular degeneration; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; fibroadipose hyperplasia; spinocerebullar ataxia type 1; CLOVES syndrome; Harlequin ichthyosis; macrodactyly syndrome; Proteus syndrome (Wiedemann syndrome); LEOPARD syndrome; systemic sclerosis; Multiple Sclerosis; lupus; fibromyalgia; AIDS and other viral diseases such as Herpes Zoster, Herpes Simplex I or II, influenza virus and cytomegalovirus; diabetes mellitus; hemihyperplasia-multiple lipomatosis syndrome; megalencephaly; rare hypoglycemia, Klippel-Trenaunay syndrome; harmatoma; Cowden syndrome; or overgrowth-hyperglycemia.

In one embodiment, the proliferative disease or disorder is cancer. In one embodiment, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" also refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which can be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Cancer can also include colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

Cancer can also include colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In one embodiment, the compounds of this application are useful for treating hematopoietic disorders, in particular, acute-myelogenous leukemia (AML), chronic-myelogenous leukemia (CML), acute-promyelocytic leukemia, and acute lymphocytic leukemia (ALL).

Exemplary cancers may also include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disease or disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Compounds and compositions of the present application can be used to treat a cancer selected from the group consisting of a hematologic cancer or a hematologic cell proliferative disorder. A hematologic cancer can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms, and mast cell neoplasms.

A "cell proliferative disorder of the lung" is a cell proliferative disease or disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Compounds and compositions of the present application can be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma", bronchioalveolar carcinoma, giant cell carcinoma, spindle cell carcinoma, and large cell neuroendocrine carcinoma. Lung cancer can include lung neoplasms having histologic and ultrastructural heterogeneity (e.g., mixed cell types).

Cell proliferative disorders of the lung can also include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that can predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. A cell proliferative disorder of the colon includes colon cancer. Compounds and compositions of the present application can be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome, and juvenile polyposis.

Cell proliferative disorders of the colon can also include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that can predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Compounds and compositions of the present application can be used to treat pancreatic cancer or cell proliferative disorders of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructural heterogeneity (e.g., mixed cell types).

A "cell proliferative disorder of the prostate" is a cell proliferative disorder involving cells of the prostate. Compounds and compositions of the present application can be used to treat prostate cancer or cell proliferative disorders of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Compounds and compositions of the present application can be used to treat skin cancer or cell proliferative disorders of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Compounds and compositions of the present application can be used to treat ovarian cancer or cell proliferative disorders of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Compounds and compositions of the present application can be used to treat breast cancer or cell proliferative disorders of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

In one embodiment, the disease or disorder includes, but is not limited to, a disease or disorders caused by or associated with *Entamoeba histolytica, Pneumocystis carinii, Trvpanosona cruzi, Trypanosoma brucei, Leishmania mexicana, Clostridium histolyticun, Staphylococcus aureus*, foot-and-mouth disease virus, or *Crithidia fasciculata*, as well as disease or disorder associated with osteoporosis, autoimmunity, schistosomiasis, malaria, tumor metastasis, metachromatic leukodystrophy, muscular dystrophy, or amytrophy.

Additional examples of the diseases or disorders include, but are not limited to, diseases or disorders caused by or associated with veterinary and human pathogenic protozoa, intracellular active parasites of the phylum Apicomplexa or Sarcomastigophora, *Trypanosoma*, Plasmodia, *Leishmania, Babesia* and *Theileria*, Cryptosporidia, Sacrocystida, Amoeba, Coccidia, and Trichomonadia. For example, the diseases or disorders include, but are not limited to, Malaria tropica, caused by, for example, *Plasmodium falciparum*; Malaria tertiana, caused by *Plasmodium vivax* or *Plasmodium ovale*, Malaria quartana, caused by *Plasmodium malariae*; Toxoplasmosis, caused by *Toxoplasma gondii*; Coccidiosis, caused for instance by *Isospora belli*; intestinal Sarcosporidiosis, caused by *Sarcocystis suihominis*; dysentery caused by *Entamoeba histolytica*; Cryptosporidiosis, caused by *Cryptosporidium parvum*; Chagas' disease, caused by *Trypanosoma cruzi*; sleeping sickness, caused by *Trypanosoma brucei rhodesiense* or *gambiense*, the cutaneous and visceral as well as other forms of Leishmaniosis; diseases or disorders caused by veterinary pathogenic protozoa, such as *Theileria parva*, the pathogen causing bovine East coast fever. *Trypanosoma congolense congolense* or *Trypanosoma vivar vivax*. *Trypanosoma brucei brucei*, pathogens causing Nagana cattle disease in Africa, *Trypanosoma brucei evansi* causing Surra, *Babesia bigemina*, the pathogen causing Texas fever in cattle and buffalos, *Babesia bovis*, the pathogen causing European bovine Babesiosis as well as Babesiosis in dogs, cats and sheep, *Sarcocystis ovicanis* and ovifelis pathogens causing Sarcocystiosis in sheep, cattle and pigs, Cryptosporidia, pathogens causing Cryptosporidioses in cattle and birds. *Eimeria* and *Isospora* species, pathogens causing Coccidiosis in rabbits, cattle, sheep, goats, pigs and birds, especially in chickens and turkeys. *Rickettsia* comprise species such as *Rickettsia felis, Rickettsia prowazekii. Rickettsia rickettsii, Rickettsia typhi, Rickettsia conorii, Rickettsia africae* and cause diseases such as typhus, rickettsialpox, Boutonneuse fever, African Tick Bite Fever, Rocky Mountain spotted fever. Australian Tick Typhus, Flinders Island Spotted Fever and Queensland Tick Typhus.

In one embodiment, the disease or disorder is caused by, or associated with, one or more bacteria. Examples of the bacteria include, but are not limited to, the Gram positive organisms (e.g., *Staphylococcus aureus, Staphylococcus epidermidis, Enterococcus faecalis* and *E. faecium, Streptococcus pneumoniae*) and the Gram negative organisms (e.g., *Pseudomonas aeruginosa, Burkholdia cepacia, Xanthononas maltophila, Escherichia coli, Enterobacter* spp, *Klebsiella pneumoniae* and *Salmonella* spp).

In one embodiment, the disease or disorder is caused by, or associated with, one or more fungi. Examples of the fungi include, but are not limited to, *Candida albicans, Histoplasma neoformans, Coccidioides immitis*, and *Penicillium marneffei*.

In one embodiment, the disease or disorder is a neurological disease or disorder. In one embodiment, the neurological disease or disorder involves the central nervous system (e.g., brain, brainstem and cerebellum), the peripheral nervous system (e.g., cranial nerves), and/or the autonomic nervous system (e.g., parts of which are located in both central and peripheral nervous system).

Examples of the neurological disorders include, but are not limited to, acquired epileptiform aphasia; acute disseminated encephalomyelitis; adrenoleukodystrophy; age-related macular degeneration; agenesis of the corpus callosum; agnosia: Aicardi syndrome; Alexander disease; Alpers' disease; alternating hemiplegia; Alzheimer's disease; Vascular dementia; amyotrophic lateral sclerosis; anencephaly; Angelman syndrome: angiomatosis; anoxia; aphasia; apraxia; arachnoid cysts; arachnoiditis; Anronl-Chiari malformation; arteriovenous malformation; Asperger syndrome; ataxia telegiectasia: attention deficit hyperactivity disorder; autism; autonomic dysfunction: back pain; Batten disease; Behcet's disease; Bell's palsy; benign essential blepharospasm; benign focal; amyotrophy; benign intracranial hypertension; Binswanger's disease; blepharospasm: Bloch Sulzberger syndrome: brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain: Chiari malformation; chorea; chronic inflammatory demyelinating polyneuropathy: chronic pain; chronic regional pain syndrome; Coffin Lowry syndrome; coma, including persistent vegetative state: congenital facial diplegia; corticobasal degeneration; cranial arteritis; craniosynostosis; Creutzfeldt-Jakob disease; cumulative trauma disorders; Cushing's syndrome; cytonegalic inclusion body disease; cytomegalovirus infection; dancing eyes-dancing feet syndrome: Dandy-Walker syndrome; Dawson disease: De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy: empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactica polyneuritiformis; herpes zoster oticus; herpes zoster: Hirayama syndrome; HIV-associated dementia and neuropathy (also neurological manifestations of AIDS); holoprosencephaly; Huntington's disease and other polyglutamine repeat diseases; hydranencephaly; hydrocephalus; hypercortisolism: hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Kearns-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome: lateral medullary (Wallenberg) syndrome; learning disabilities; Leigh's disease; Lennox-Gustaut syndrome: Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease: Lyme disease-neurological sequelae; Machado-Joseph disease; macrencephaly; megalencephaly; Melkersson-Rosenthal syndrome: Menieres disease; meningitis: Menkes disease; metachromatic leukodystrophy; microcephaly; migraine: Miller Fisher syndrome; mini-strokes; mitochondrial myopathies: Mobius syndrome; monomelic amyotrophy: motor neuron disease; Moyamoya disease; mucopolysaccharidoses; milti-infarct dementia; multifocal motor neuropathy: multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome: neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence: Ohtahara syndrome; olivopontocerebellar atrophy; opsoclonus myoclonus; optic neuritis; orthostatic hypotension; overuse syndrome; paresthesia; Parkinson's disease; paramyotonia congenital; paraneoplastic diseases: paroxysmal attacks; Parry Romberg syndrome; Pelizaeus-Merzbacher disease; periodic paralyses; peripheral neuropathy; painful neuropathy and neuropathic pain: persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocal leukoencephalopathy; progressive sclerosing poliodystrophy; progressive supranuclear palsy; pseudotumor cerebri; Ramsay-lunt syndrome (types I and II); Rasmussen's encephalitis; reflex sympathetic dystrophy syndrome; Refsum disease; repetitive motion disorders: repetitive stress injuries; restless legs syndrome: retrovirus-associated myelopathy; Rett syndrome; Reye's syndrome; Saint Vitus dance; Sandhoff disease; Schilder's disease; schizencephaly; septo-optic dysplasia; shaken baby syndrome: shingles; Shy-Drager syndrome; Sjögren's syndrome: sleep apnea; Soto's syndrome: spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy: Sydenham chorea; syncope; syringomyclia; tardive dyskinesia; Tay-Sachs disease: temporal arteritis; tethered spinal cord syndrome; Thomsen disease: thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis: Von Hippel-Lindau disease: Wallenberg's syndrome; Werdnig-Hoffman disease; West syndrome; whiplash; Williams syndrome; Wildon's disease: and Zellweger syndrome.

Examples of neurodegenerative diseases can also include, without limitation, Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and Toxic encephalopathy.

In one embodiment, the disease or disorder is an autoimmune disease. Examples of autoimmune diseases include, but are not limited to, rheumatoid arthritis, systemic lupus erythematosus, inflammatory bowel diseases (IBDs) comprising Crohn disease (CD and ulcerative colitis (UC) which are chronic inflammatory conditions with polygenic susceptibility.

In one embodiment, the disease or disorder is inflammation, arthritis, rheumatoid arthritis, spondyiarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, peripheral neuropathy, or B-Cell Lymphoma.

In one embodiment, the disease or disorder is selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In one embodiment, the disease or disorder is selected from a proliferative disorder and an immune disorder.

As modulators of a STING protein, the compounds and compositions of this application are also useful in assessing, studying, or testing biological samples. One aspect of the application relates to modulating the activity of a STING protein in a biological sample, including contacting the biological sample with a compound or a composition of the application.

The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Modulation (e.g., inhibition or stimulation) of protein kinase activity in a biological sample is useful for a variety of purposes that are known to one of skill in the art. Examples of such purposes include, but are not limited to, blood transfusion, organ transplantation, and biological specimen storage.

Another aspect of this application relates to the study of a STING protein in biological and pathological phenomena; the study of intracellular signal transduction pathways mediated by STING protein. Examples of such uses include, but are not limited to, biological assays such as enzyme assays and cell-based assays.

The activity of the compounds and compositions of the present application as STING modulators can be assayed in vitro, in vivo, or in a cell line. In vitro assays include assays that determine modulation (e.g., inhibition or stimulation) of binding of a STING ligand to a STING protein through competitive binding assay. Alternate in vitro assays quantitate the ability of the modulator (e.g., inhibitor or stimulator) to bind to the protein kinase and can be measured either by radio labelling the modulator (e.g., inhibitor or stimulator) prior to binding, isolating the ligand/protein complex and determining the amount of radio label bound. Detailed conditions for assaying a compound utilized in this application as a modulator or a STING protein are set forth in the Examples below.

In accordance with the foregoing, the present application provides a method for preventing or treating any of the diseases or disorders described above in a subject in need of such treatment, including administering to the subject a therapeutically effective amount of a compound of the application or an enantiomer, diastereomer, stereoisomer, or pharmaceutically acceptable salt thereof, or a pharmaceutical composition of the application. For any of the above uses, the required dosage will vary depending on the mode of administration, the particular condition to be treated and the effect desired.

Compounds and compositions of the application can be administered in therapeutically effective amounts in a combinational therapy with one or more therapeutic agents (pharmaceutical combinations) or modalities, e.g., anti-proliferative, anti-cancer, immunomodulatory, or anti-inflammatory agent, and/or non-drug therapies, etc. For example, synergistic effects can occur with anti-proliferative, anti-cancer, immunomodulatory, or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy may include the administration of the subject compounds in further combination with one or more other biologically active ingredients (such as, but not limited to, a second STING modulator, a modulator of the cGAS-CDN-STING axis, or a modulator involved in the intracellular dsDNA mediated type-1 interferon activation. Other biologically active ingredients can also include anti-proliferative agents, anti-cancer agents (e.g., chemotherapeutic agents), immunomodulatory agents, antibodies, etc. For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

In one embodiment, the chemotherapeutic agent is an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug, or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodinem tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Exemplary histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur—0.4 M 5-chloro-2,4-dihydroxypyrimidine—1 M potassium oxonate) or lovastatin.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

In one embodiment, the compounds can be administered in combination with one or more separate pharmaceutical agents, e.g., a chemotherapeutic agent, an immunotherapeutic agent, or an adjunctive therapeutic agent.

As used herein, "combination therapy" or "co-therapy" includes the administration of a compound of the present application, or a pharmaceutically acceptable salt or ester thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present application.

"Combination therapy" is intended to embrace administration of these therapeutic agents in a sequential manner, where each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected can be administered by intravenous injection while the other therapeutic agents of the combination can be administered orally. Alternatively, for example, all therapeutic agents can be administered orally or all therapeutic agents can be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment can be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Definitions

Listed below are definitions of various terms used in this application. These definitions apply to the terms as they are used throughout this specification and claims, unless otherwise limited in specific instances, either individually or as part of a larger group.

The term "alkyl," as used herein, refers to saturated, straight or branched-chain hydrocarbon radicals containing, in certain embodiments, between one and six carbon atoms. Examples of $C_1$-$C_6$ alkyl radicals include, but are not limited to, methyl, ethyl, propyl, isopropyl, n-butyl, tert-butyl, neopentyl, and n-hexyl radicals.

The term "alkenyl," as used herein, denotes a monovalent group derived from a hydrocarbon moiety containing, in certain embodiments, from two to six carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, pentenyl, hexenyl, heptenyl, octenyl, nonenyl, decenyl, and the like.

The term "alkynyl," as used herein, denotes a monovalent group derived from a hydrocarbon moiety containing, in certain embodiments, from two to six carbon atoms having at least one carbon-carbon triple bond. The triple bond may or may not be the point of attachment to another group. Alkynyl groups include, but are not limited to, for example, ethynyl, propynyl, butynyl, pentynyl, hexynyl, heptynyl, octynyl, nonynyl, decynyl, and the like.

The term "alkoxy" refers to an —O-alkyl radical.

The terms "hal", "halo" and "halogen," as used herein, refer to an atom selected from fluorine, chlorine, bromine and iodine.

The term "cycloalkyl," as used herein, denotes a monovalent group derived from a monocyclic or polycyclic saturated or partially unsaturated carbocyclic ring compound. Examples of $C_3$-$C_8$ cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl.

The term "cycloalkenyl," as used herein, denotes a monovalent group derived from a monocyclic or polycyclic saturated or partially unsaturated carbocyclic ring compound including at least one carbon-carbon double bond. Examples of $C_4$-$C_8$ cycloalkenyl include, but not limited to, cyclobutenyl, cyclopentenyl, cyclohexenyl, cyclopentenyl and cyclooctenyl.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl, and the like.

The term "aralkyl," as used herein, refers to an alkyl residue, such as those described herein, attached to an aryl ring, such as those described herein. Examples include, but are not limited to, benzyl, phenethyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, indazoyl, cinnolinyl, phthalazinyl, pyridazinyl, indolyl, acridinyl, benzoquinolinyl, pyrimidinyl, a purinyl, pyrrolopyrimidinyl, quinoxalinyl, quinazolinyl, indazolinyl, and phthalazinyl, and the like.

The term "heteroaralkyl," as used herein, refers to an alkyl residue, such as those described herein, attached to a heteroaryl ring, such as those described herein. Examples include, but are not limited to, pyridinylmethyl, pyrimidinylethyl, and the like.

In accordance with the application, any of the aryls, substituted aryls, heteroaryls and substituted heteroaryls described herein, can be any aromatic group. Aromatic groups can be substituted or unsubstituted.

The term "heterocyclyl," as used herein, refers to a non-aromatic mono- or poly-cyclic (e.g., bi-, or tri-cyclic or more) fused or non-fused, radical or ring system having from three to ten ring atoms of which one ring atoms is selected from S, O, and N; zero, one, or two ring atoms are additional heteroatoms independently selected from S, O, and N; and the remaining ring atoms are carbon. Representative heterocycloalkyl groups include, but are not limited to, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl, and the like.

The term "alkylamino" refers to a group having the structure —NH($C_1$-$C_{12}$ alkyl), e.g., —NH($C_1$-$C_6$ alkyl), where $C_1$-$C_6$ alkyl is as previously defined.

The term "dialkylamino" refers to a group having the structure —N($C_1$-$C_{12}$ alkyl)$_2$, e.g., —NH($C_1$-$C_6$ alkyl), where $C_1$-$C_6$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

As described herein, compounds of the application and moieties present in the compounds can optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group can have a substituent at each substitutable position of the group, and when more than one position in any given structure can be substituted with more than one substituent selected from a specified group, the substituent can be either the same or different at every position. The terms "optionally substituted", "optionally substituted alkyl," "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocyclyl," and any other optionally substituted group as used herein, refer to groups that are substituted or unsubstituted by independent replacement of one, two, or three or more of the hydrogen atoms thereon with substituents including, but not limited to: —F, —Cl, —Br, —I, —OH, protected hydroxy, —NO$_2$, —CN, —NH$_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O— heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkenyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkenyl, —OCONH-aryl, —OCONH—$C_3$-$C_{12}$-cycloalkyl, —OCONH-heteroaryl, —OCONH— heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHCO$_2$—$C_3$-$C_{12}$-cycloalkyl, —NHCO$_2$-aryl, —NHCO$_2$-heteroaryl, —NHCO$_2$— heterocycloalkyl, NHC(O)NH$_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, NHC(O)NH— heterocycloalkyl, —NHC(S)NH$_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH— heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NHheterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, C(NH)NH—$C_3$-$C_{12}$-cycloalkyl, —C(NH)NH-aryl, —C(NH)NH-heteroaryl, —C(NH)NHheterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkenyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_{12}$-alkenyl, —NHSO$_2$—$C_2$-$C_{12}$-alkenyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S— heterocycloalkyl, or methylthiomethyl.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "subject" as used herein refers to a mammal. A subject therefore refers to, for example, dogs, cats, horses, cows, pigs, guinea pigs, and the like. Preferably the subject is a human. When the subject is a human, the subject can be referred to herein as a patient.

"Treat", "treating" and "treatment" refer to a method of alleviating or abating a disease and/or its attendant symptoms.

As used herein, "preventing" or "prevent" describes reducing or eliminating the onset of the symptoms or complications of the disease, condition or disorder.

The terms "disease(s)", "disorder(s)", and "condition(s)" are used interchangeably, unless the context clearly dictates otherwise.

The term "therapeutically effective amount" of a compound or pharmaceutical composition of the application, as used herein, means a sufficient amount of the compound or pharmaceutical composition so as to decrease the symptoms of a disorder in a subject. As is well understood in the medical arts a therapeutically effective amount of a compound or pharmaceutical composition of this application will be at a reasonable benefit/risk ratio applicable to any medical treatment. It will be understood, however, that the total daily usage of the compounds and compositions of the present application will be decided by the attending physician within the scope of sound medical judgment. The specific modulatory (e.g., inhibitory or stimulatory) dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences,* 66: 1-19 (1977) which is herein expressly incorporated by reference. The salts can be prepared in situ during the final isolation and purification of the compounds of the application, or separately by reacting the free base or acid function with a suitable acid or base.

Examples of pharmaceutically acceptable salts include, but are not limited to, nontoxic acid addition salts: salts formed with inorganic acids such as hydrochloric acid, hydrobromic acid, phosphoric acid, sulfuric acid and perchloric acid, or with organic acids such as acetic acid, maleic acid, tartaric acid, citric acid, succinic acid or malonic acid.

Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, 7-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein, refers to those prodrugs of the compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application.

"Prodrug", as used herein, means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002) each of which are herein expressly incorporated by reference.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use.

A "pharmaceutically acceptable excipient" as used in the specification and claims includes both one and more than one such excipient.

This application also encompasses pharmaceutical compositions containing, and methods of treating disorders through administering, pharmaceutically acceptable prodrugs of compounds of the application. For example, compounds of the application having free amino, amido, hydroxy or carboxylic groups can be converted into prodrugs. Prodrugs include compounds where an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups can be derivatized using groups including but not limited to hemisuccinates, phosphate esters, dimethylaminoacetates, and phosphoryloxymethyloxy carbonyls, as outlined in *Advanced Drug Delivery Reviews*, 1996, 19, 1-15 which is herein expressly incorporated by reference. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers where the acyl group can be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties can incorporate groups including but not limited to ether, amine and carboxylic acid functionalities.

Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

When any variable (e.g., $R_1$) occurs more than one time in any constituent or formula for a compound, its definition at each occurrence is independent of its definition at every other occurrence. Thus, for example, if a group is shown to be substituted with one or more R moieties, then R at each occurrence is selected independently from the definition of R. Also, combinations of substituents and/or variables are permissible, but only if such combinations result in stable compounds within a designated atom's normal valency.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that can be defined, in terms of absolute stereochemistry, as (R)- or (S)-, or as (D)- or (L)- for amino acids. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration unless the text so states; thus a carbon-carbon double bond depicted arbitrarily herein as trans can be cis, trans, or a mixture of the two in any proportion. All such isomeric forms of such compounds are expressly included in the present application.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center can exist either as an individual diastereomer or as a mixture of diastereomers, termed "diastereomeric mixture". When one chiral center is present, a stereoisomer can be characterized by the absolute configuration (R or S) of that chiral center, e.g., carbon. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. The compounds of this application can also be represented in multiple tautomeric forms, in such instances, the application expressly includes all tautomeric forms of the compounds described herein (e.g., alkylation of a ring system can result in alkylation at multiple sites, the application expressly includes all such reaction products).

In the present application, the structural formula of the compound represents a certain isomer for convenience in some cases, but the present application includes all isomers, such as geometrical isomers, optical isomers based on an asymmetrical carbon, stereoisomers, tautomers, and the like. In the present specification, the structural formula of the compound represents a certain isomer for convenience in some cases, but the present application includes all isomers, such as geometrical isomers, optical isomers based on an asymmetrical carbon, stereoisomers, tautomers, and the like.

Additionally, the compounds of the present application, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$ It is to be understood that the triazole ring of Formula (I), where $R^2$ is hydrogen, can represent several tautomeric forms (Kubota, S. and Uda M. *Chem. Pharm Bull.* 23(5) 1975 pp. 955-966 which is herein expressly incorporated by reference). The chemical structures of the resulting tautomerization are shown below:

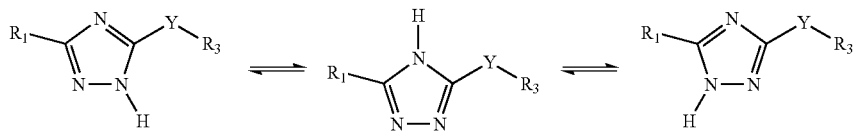

Furthermore, it is to be understood that the structural representation of a single tautomeric form encompasses the other two via this tautomerization mechanism. It is to be understood that the compounds of the present invention can be depicted as different tautomers. When compounds have tautomeric forms, all tautomeric forms are intended to be included in the scope of the present invention, and the naming of the compounds does not exclude any tautomer form. It will be understood that certain tautomers can have a higher level of activity than others.

In the present specification, the structural formula of the compound represents a certain isomer for convenience in some cases, but the present application includes all isomers, such as geometrical isomers, optical isomers based on an asymmetrical carbon, stereoisomers, tautomers, and the like.

EXAMPLES

The purity of all compounds was over 95% and was analyzed with Waters LC/MS system. $^1$H NMR was obtained at 400 MHz. Chemical shifts are reported relative to dimethyl sulfoxide ($\delta$=2.50) for $^1$H NMR. Data are reported as (br=broad, s=singlet, d=doublet, t=triplet, q=quartet, m=multiplet).

Abbreviations used in the following examples and elsewhere herein are: AcOH—acetic acid; atm—atmosphere; BOC2O di-tert-butyl dicarbonate; br—broad; CuSO$_4$-copper sulfate; CDC$_3$—deuterated chloroform; DCM—dichloromethane; DIEA—N,N-diisopropylethylamine; DMA—N,N-dimethylacetamide; DMAP—4-dimethylaminopyridine; DMF—N,N-dimethylformamide; DMSO—dimethyl sulfoxide; DMSO-d$_6$ deuterated dimethyl sulfoxide; EDCI—1-ethyl-3-(3-dimethylaminopropyl) carbodiimide; ESI—electrospray ionization; EtOAc—ethyl acetate; HCl—hydrochloric acid; h—hour(s); HPLC—high performance liquid chromatography; LCMS—liquid chromatography mass spectrometry; m—multiplet; mL—milliliter; MeCN—acetonitrile; MeOH—methanol; mg—milligram; mmol—millimole; MgSO$_4$ magnesium sulfate; MHz—megahertz; min—minutes; MS—mass spectrometry; Na$_2$CO$_3$ sodium carbonate; NaHCO$_3$ sodium bicarbonate; NMR—nuclear magnetic resonance; Tf—triflate; Pd$_2$(dba)$_3$—tris(dibenzylideneacetone)dipalladium(0); Pd(PPh$_3$)$_2$Cl$_2$ bis(triphenylphosphine)palladium(II) dichloride; ppm—parts per million; PTSA—para-toluene sulfonic acid; rt—room temperature; TBAF—tetra-n-butylammonium fluoride; t-BuOH—tertiary butanol; TFA—trifluoroacetic acid; TMS—trimethylsilane; THF—tetrahydrofuran; TLC—thin layer chromatography; μL—microliter.

Example 1

Figure 1A:
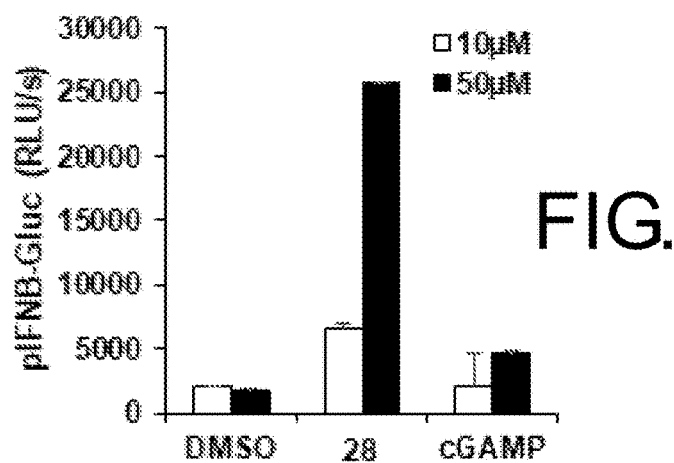
FIG. 1A shows luciferase induction measured relative to SEAP production when Compound 28 (in 0.5% DMSO) or cGAMP (25 µM in PBS) was placed onto hTERT-pIFNβ-Glu cells (hTERT cells stably containing the type I IFNβ promoter driving luciferase and the CMV promoter driving SEAP) for 12 hours.
Figure 1B:
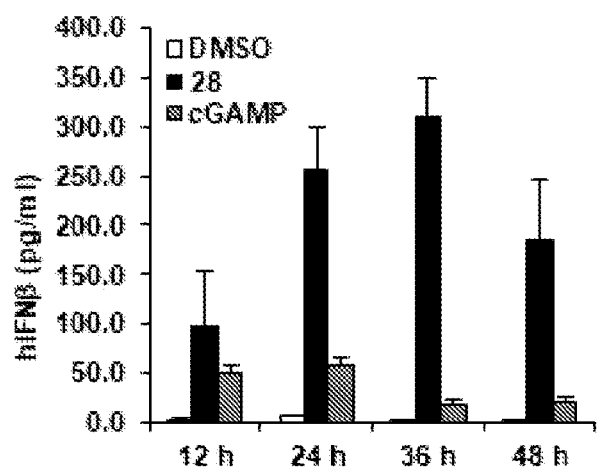
FIG. 1B shows IFNβ production measured at different time points in hTERT cells (Compound 28 in 0.5% DMSO)
Figure 1C:
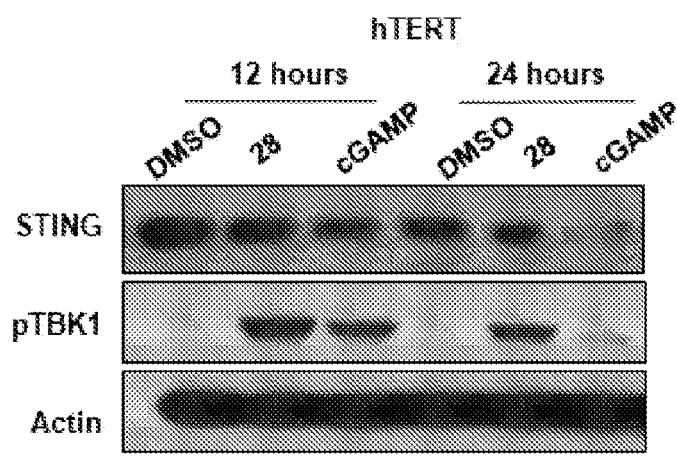
FIG. 1C shows that Compound 28 activates STING dependent TBK1 phosphorylation.

Identification of small molecule activators of STING. An assay was designed to identify small compounds that bound to STING. To achieve this, the carboxyl terminal region of STING (amino acids 152-379) fused to a histidine tag was expressed in bacteria as described in materials and methods. Soluble STING dimers were purified over a nickel affinity column and enriched further using gel filtration. Purified STING was used in a thermal shift assay (TSA) to isolate small molecules that bound to STING. A thermal shift assay quantifies the change in the thermal denaturation temperature of a protein. The binding of low molecular weight ligands, such as small molecules, can increase the thermal stability of a protein, in this case STING. Essentially, the denaturation temperature of STING is expected to be different if a small compound is physically associated with it. The denaturation profile of purified STING (STING152-379H) was calibrated using a fluorometer equipped with temperature control (a qPCR apparatus with 320 well capacity). Once this was established, purified STING (5 μl; 1 μM) was mixed with 2.5 μl DMSO and compound (1% DMSO final with 2.5% SYPRO orange. The total reaction mixture was 10 μl in 50 μM HEPES and 100 mM NaCl. SYPRO Orange binds nonspecifically to hydrophobic surfaces. When the protein unfolds, the exposed hydrophobic surfaces bind the dye, resulting in an increase in fluorescence by excluding water. The stability curve and its midpoint value (melting temperature, Tm also known as the temperature of hydrophobic exposure, Th) was obtained by gradually increasing the temperature to unfold the protein and measuring the fluorescence at each point. Curves were measured for STING only and STING+small molecule, and ΔTm was calculated. The temperature ramp was 0.1 Centigrade/second. Approximately 250,000 compounds were screened from the EMININE stock collection of compounds. Over 100 compounds were defined as confirmed hits (dTMm >0.5 C at 7.5 μM OR >1 C @ 30 μM). These compounds were subsequently examined for their ability to activate the type I interferon promoter in live cell assays. Only one compound isolated by TSA (Compound 28, 2-(4-benzylphenyl)-3-sulfanylidene-5,6,7,8-tetrahydro-[1,2,4]triazolo[1,2-a]pyridazin-1-one) was confirmed as being able to stimulate STING activity, the activation of both NF-κB and IRF3 and induce the production of type I IFN and other cytokines, when added to human fibroblasts (hTERT) as described next (FIGS. 1A, 1B, and 1C).

Example 2

Figure 1D:
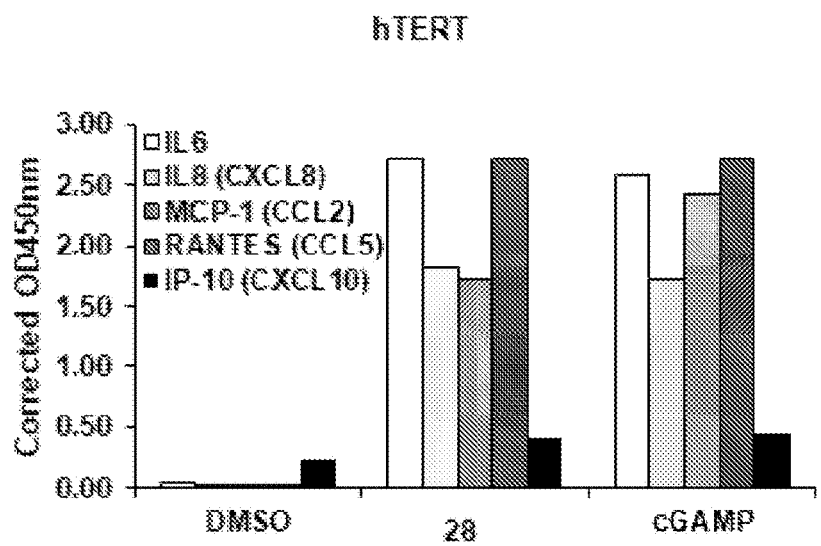
FIG. 1D shows that Compound 28 activates cytokine production in hTERT cells.
Figure 1E:
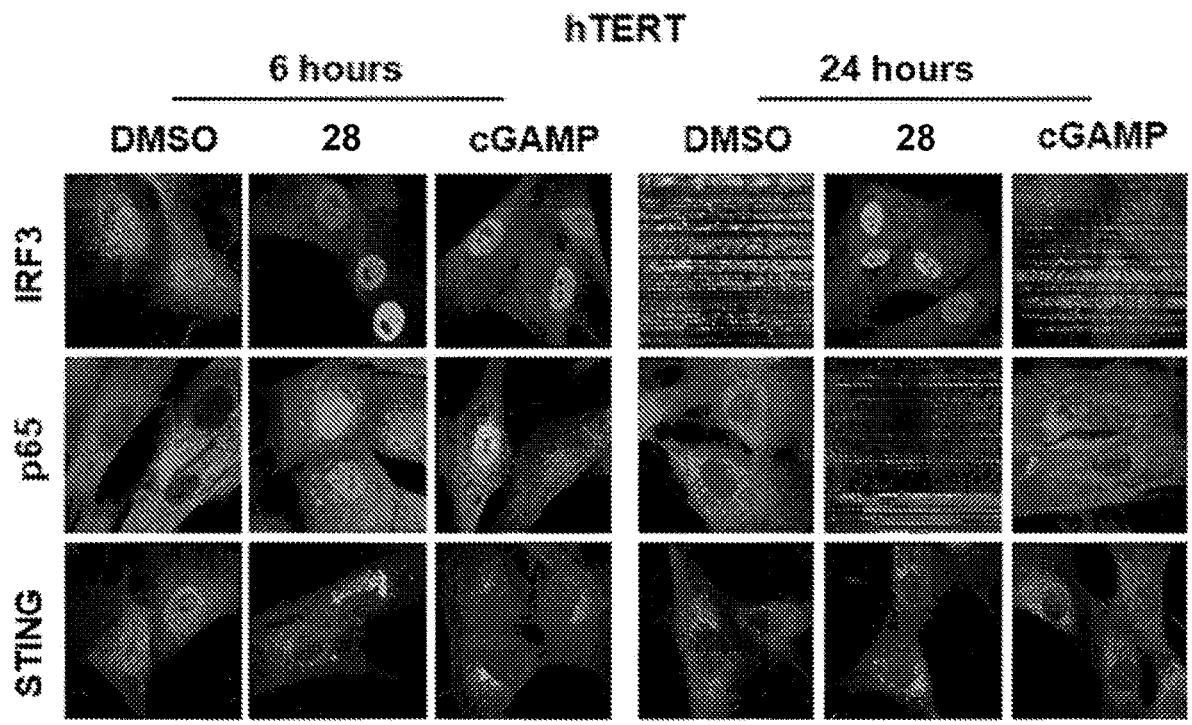
FIG. 1E shows Compound 28 induces STING trafficking and IRF3/NF-κB activation and nuclear localization in hTERT cells.

Examining Agonists of STING. Compounds of the present invention were examined for its ability to activate the type I interferon (IFN) promoter, using a live cell assay. This assay comprised immortalized human fibroblasts (hTERT) that were stably transfected with the type I IFN promoter driving luciferase as well as the CMV promoter driving SEAP (hTERT-pIFNβ-Glu). The live cell assay was developed by the Barber lab and has been patented. The ability of the small molecules to activate the type I IFN promoter and the transcription of luciferase, but not SEAP was assessed. This is since the activation of STING, typically by CDNs, in turn activates the transcription factors NF-κB and IRF3, both of which are required to induce the transcriptional stimulation of the Type I IFN promoter, but not the CMV promoter (IRF3 and NF-kB transcription factor binding sites are not contained in the CMV promoter). Thus, activation of STING by a small molecule identified in the first screen (HTS), results in the level of luciferase increasing relative to SEAP production. Compound 28 from the first screen (HTS STING binding assay) exhibited the ability to activate the type I IFN promoter in hTERT-pIFNβ-Glu and induce the expression of luciferase but not SEAP (Compound 28, FIGS. 1A and 1B). To confirm this, Compound 28 was administered onto normal hTERT cells and the production of Type I IFN measured using ELISA (FIG. 1C). The Compound 28 stimulated the activation of the Type I IFN promoter similar to, or better than equal amounts of the known STING agonist, the CDN cGAMP, which was used as a positive control (FIGS. 1B and 1C). Similar to cGAMP, Compound 28 was also able to activate TBK-1, the kinase of IRF3 and the production of cytokines IL6, IL8 and MCP-1 in hTERT cells, as determined by ELISA (which are IRF3 dependent; FIGS. 1D and 1E). Using hTERT cells, it was confirmed that Compound 28 was able to specifically activate STING (as determined by STING trafficking, and exhibited robust activation of STING and TBK1 activity compared to cGAMP (FIG. 1E). It is noteworthy that Compound 28 also stimulated the activation of STING, for over 24 hours, compared to CDNs, probably by stabilizing STING and preventing degradation (FIG. 1F). This was evident by observing that STING trafficking was noted at 24 hours post-treatment as well as the nuclear localization of both NF-κB and IRF3. In contrast, CDN stimulation of STING lasted less than 12 hours and no trafficking of STING or nuclear localization of IRF3 or NF-kB was observed at 24 hours. Thus, Compound 28 is a more robust activator of STING compared to CDNs. The specificity of Compound 28 was demonstrated by showing that hTERT cells lacking STING (using RNAi) were unable to produce type I IFN, when exposed to Z539, compared to hTERT cells treated with a control RNAi (FIG. 1G). Collectively, our data indicates that Compound 28 can bind to and specifically activate STING signaling, to stimulate both NF-kB and IRF3 function and drive the expression of the type I IFN promoter and other cytokines and genes.

Example 3

Development of novel analogues of 28. Based on the structure of Compound 28, approximately three thousand (3000) similarly structured compounds were designed and tested for their ability to bind to STING in TSA. Many (approximately 200) compounds exhibited the ability to associate with STING as determined by TSA and were next tested for their ability to activate the type I IFN promoter. Compound 28 exhibited the ability to stimulate the transcription of the IFNβ promoter in human cells (FIGS. 2A and 2B) and/or stimulate type I IFN production (FIGS. 2A and 2B). Based on the structure of Compound 28 new chemical entities were chemically synthesized. These novel synthesized compounds were tested for their ability to bind to STING in TSA assays and subsequently to activate the type I IFN promoter in human cells. Of these novel synthesized compounds (see Table II) the embodiments herein were selected for further analysis. Based on preliminary data properties, Compound 81 was further examined for its ability to activate STING signaling, compared to cGAMP. This was achieved by placing the new analogues onto hTERT-pIFNβ-Glu or hTERT cells and measuring luciferase or type I IFN production, respectively (FIG. 4).

Example 4

Figure 4A:
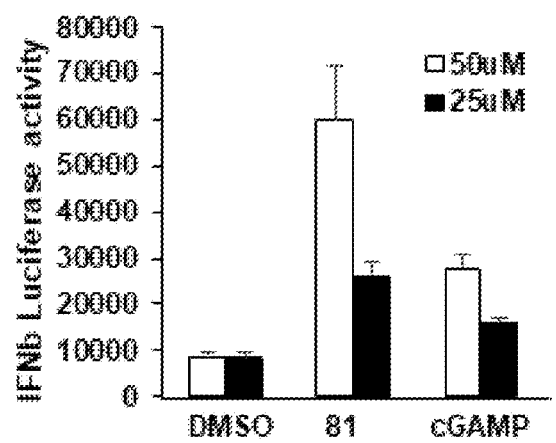
FIG. 4A shows activity of both Compound 81 (0.5% DMSO) and cGAMP, after being placed onto hTERT-pIFNβ-Glu cells (hTERT cells stably containing the type I IFNβ promoter driving luciferase and the CMV promoter driving SEAP) for 12 hours and luciferase induction measured relative to SEAP production.
Figure 4B:
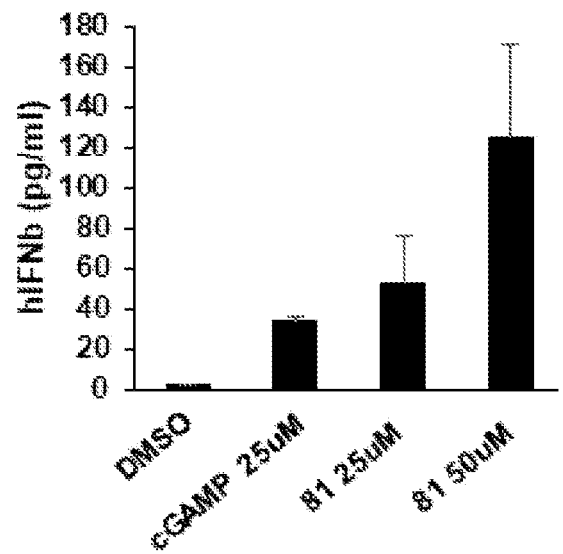
FIG. 4B shows IFNβ production measured in hTERT cells (Compound 81 in 0.5% DMSO)
Figure 4C:
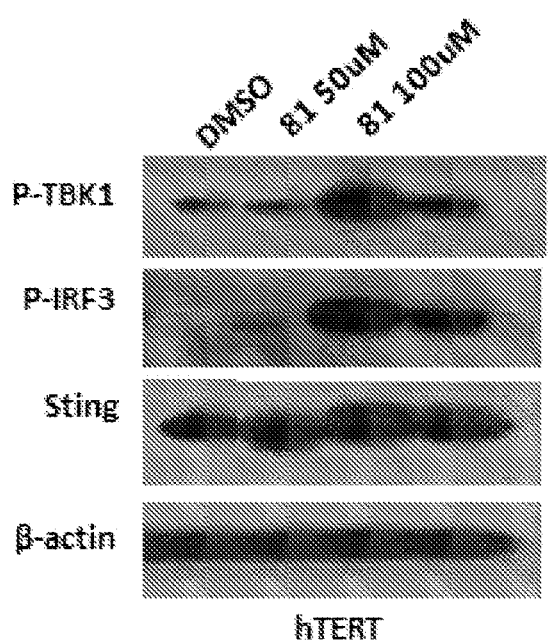
FIG. 4C shows Compound 81 activates STING dependent TBK1 and IRF3 phosphorylation.
Figure 4D:
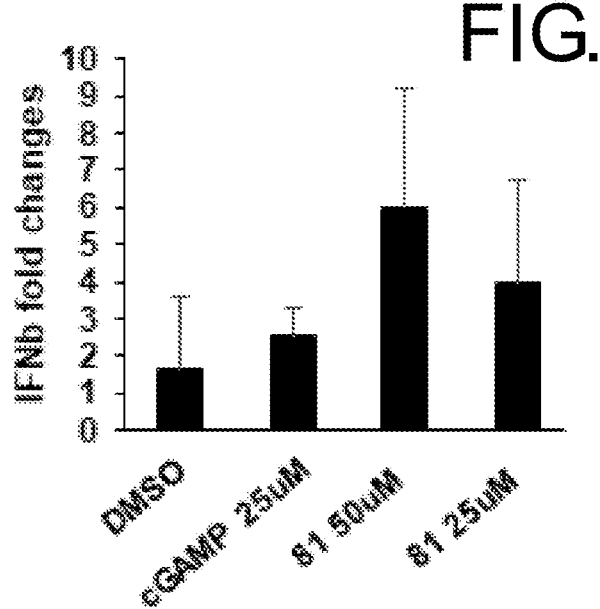
FIG. 4D shows Compound 81 activates cytokine IFNβ transcription in hTERT cells, as measured by Real Time-Polymerase Chain Reaction (RT-PCR)
Figure 4E:
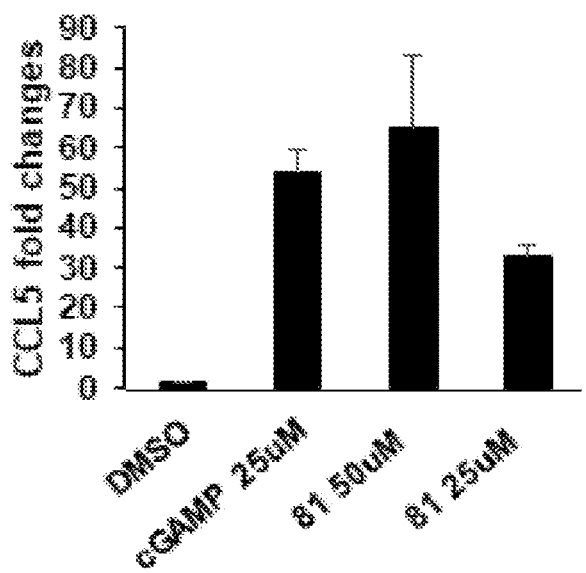
FIG. 4E shows Compound 81 activates cytokine CCL5 transcription in hTERT cells, as measured by RT-PCR.
Figure 4F:
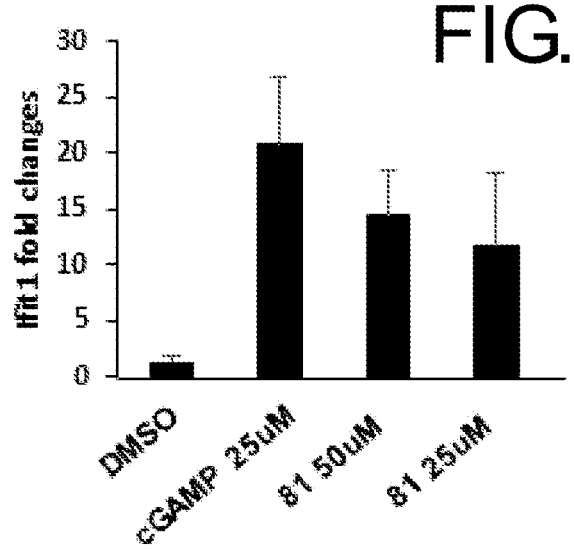
FIG. 4F shows Compound 81 activates cytokine IFIT1 transcription in hTERT cells, as measured by RT-PCR.
Figure 5A:
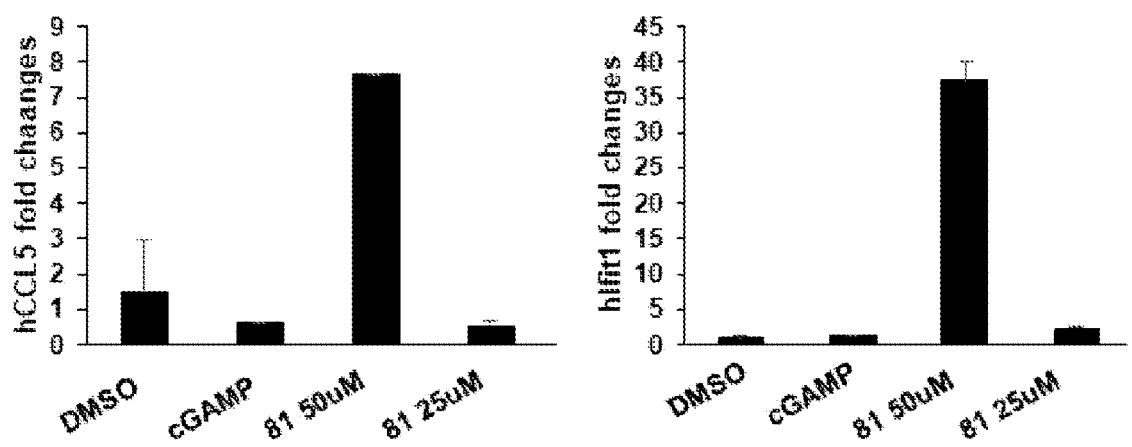
FIG. 5A shows the activity of Compound 81 (0.5% DMSO) in human cells after being placed onto human macrophages and the transcription of human CCL5 (left hand side) and human IFIT1 (right hand side) measured after 12 hours by RT-PCR.
Figure 5B:
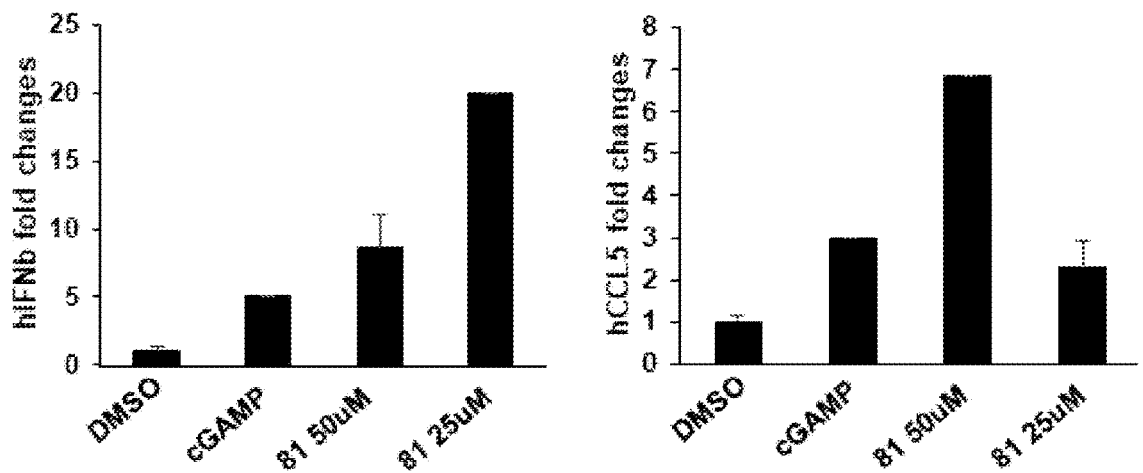
FIG. 5B shows the activity of Compound 81 (0.5% DMSO) in human cells after being placed onto human macrophages and the transcription of human CCL5 (right hand side) and human IFNβ (left hand side) measured after 12 hours by RT-PCR.
Figure 5C:
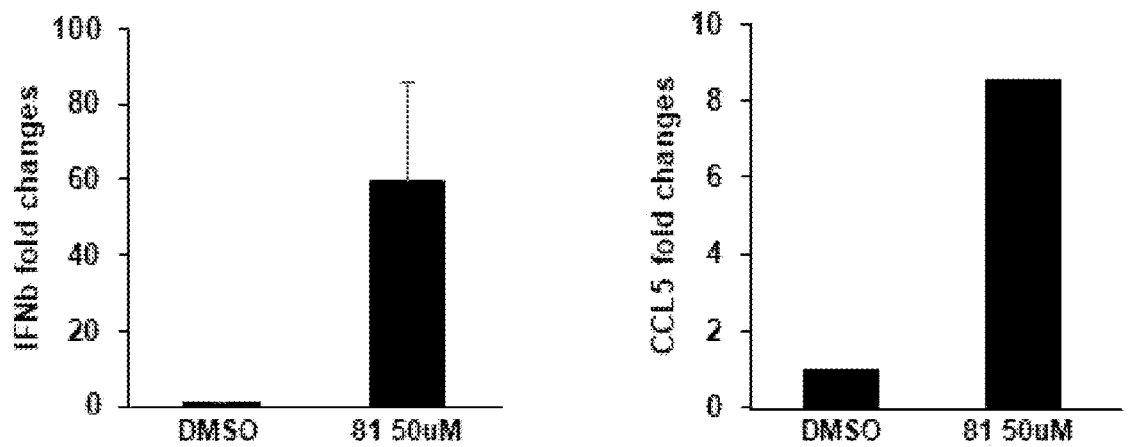
FIG. 5C shows the activity of Compound 81 (0.5% DMSO) after being placed onto human peripheral blood monocytes (hPBM's) and the transcription of IFNβ (left hand side) or CCL5 (right hand side) measured after 12 hours.

Examination of Compound 81 as an Agonist of STING. A chemically synthesized analog (Compound 81) was confirmed as activating both the type I IFN promoter in hTERT-pIFNβ-Glu cells as well as in normal hTERT fibroblasts (FIGS. 4A, 4B and 4C). Compound 81 was confirmed as inducing the phosphorylation of TBK1 and IRF3, a prerequirement for the transcriptional induction of the Type I IFN gene (FIG. 4D). Compound 81 was also found to stimulate the transcription of other cytokines such as CCL5 and IFIT1 in human fibroblasts (FIGS. 4D, 4E and 4F). To examine whether Compound 81 can also stimulate STING signaling in human immune cells, macrophages and human peripheral blood monocytes were retrieved and treated with Compound 81. Results indicated that Compound 81 can stimulate the transcription of cytokines such as CCL5, IFIT1 and IFNβ in human macrophages and human peripheral blood monocytes (FIGS. 5A, 5B and 5C). Collectively, our data indicates that Compound 81 exerts the capabilities of binding to and activating human STING, to induce STING-dependent signaling and cytokine production.

Example 5

Figure 6G:
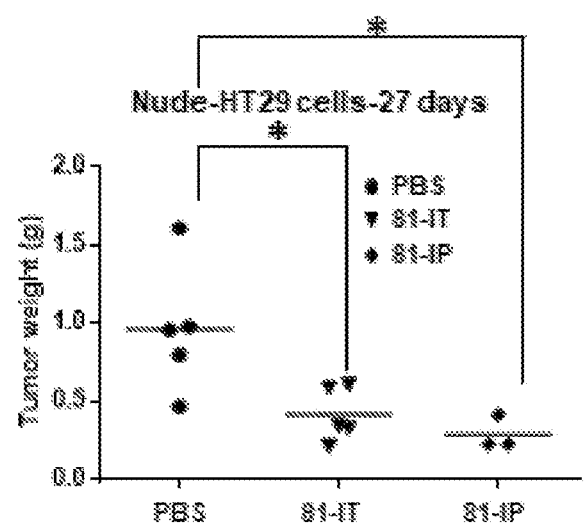
FIG. 6G shows a statistical evaluation demonstrating that Compound 81 exerts direct anti-tumor activity in vivo on human tumors even in the absence of adaptive immune responses (nude mice)
Figure 6A:
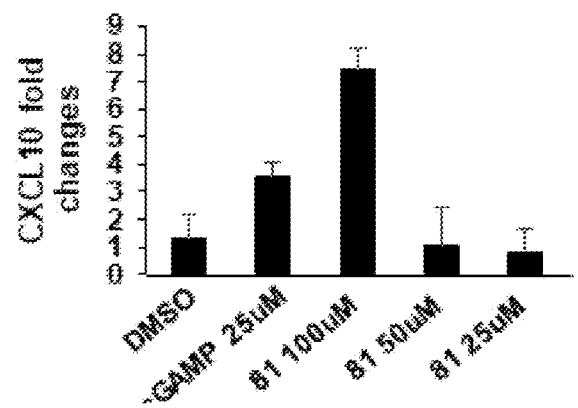
FIG. 6A shows the activity of Compound 81 (0.5% DMSO) after being placed onto the human colon cancer cell HT29 for 12 hours as measured by RT-PCR transcription of CXCL10.
Figure 6B:
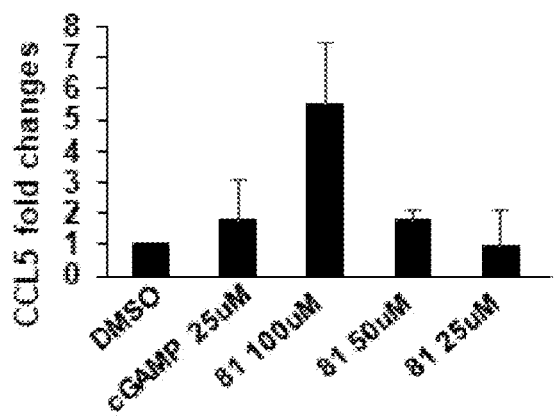
FIG. 6B shows the activity of Compound 81 (0.5% DMSO) after being placed onto the human colon cancer cell HT29 for 12 hours as measured by RT-PCR transcription of CCL5.
Figure 6C:
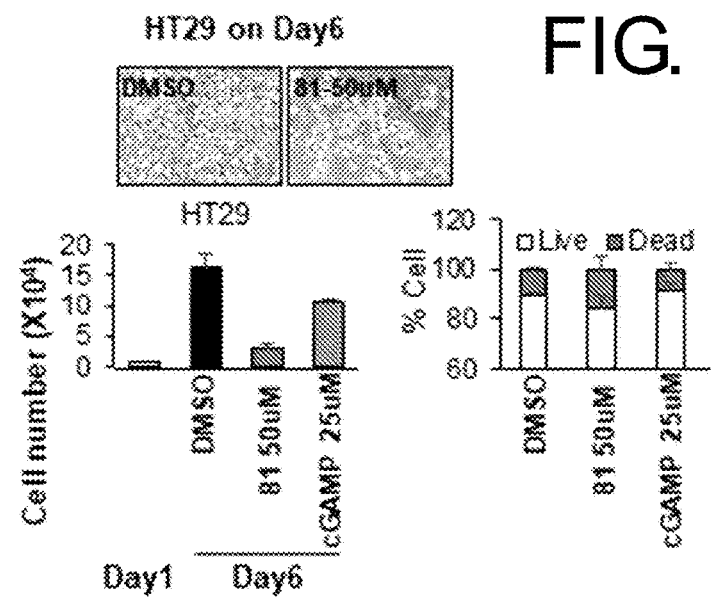
FIG. 6C shows Compound 81 induces growth arrest in HT29 cells in vitro. HT29 cells were treated with Compound 81 (50 µM in 0.5% DMSO) for approximately 72 hours and then washed and fresh medium added.
Figure 6D:
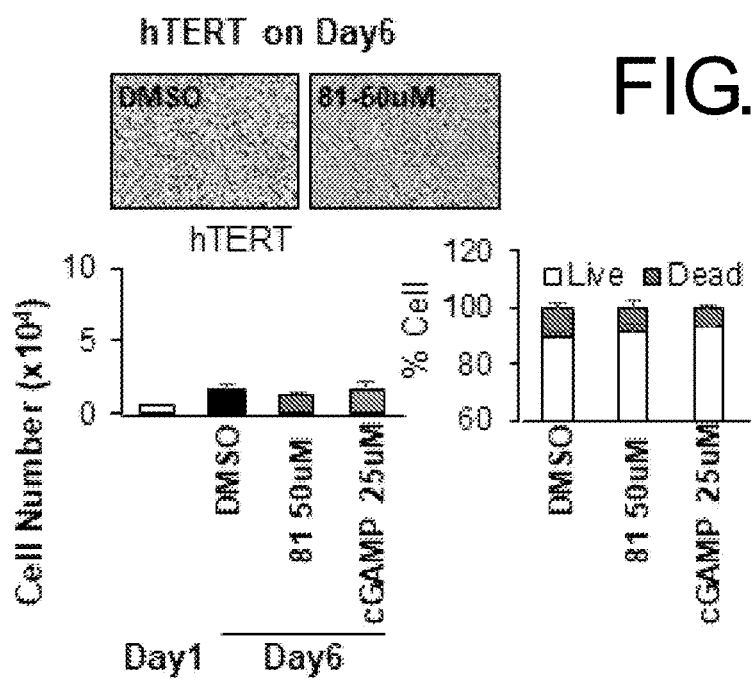
FIG. 6D shows Compound 81 induces no growth arrest on normal, untransformed hTERT cells in vitro. hTERT cells were treated with Compound 81 (50 µM in 0.5% DMSO) for approximately 72 hours and then washed and fresh medium added.

Compound 81 exerts anti-tumor activity on human cancer cells: To evaluate the effects of 81 on tumor cells, the human colon cancer cell HT-29 was treated for 24 hours (25-100 μM in 0.5% DMSO). This data confirmed that Compound 81 can similarly induce the transcription of cytokines CXCL10 and CCL5 (FIGS. 6A and 6B). Compound 81 was also shown to induce evidence of Senescence-Associated Secretory Phenotype (SASP) in HT-29 cells. For example, HT-29 cells treated with Compound 81 underwent growth arrest (FIG. 6C). Further, cell growth shown in FIG. 6C was monitored for 72 more hours (6 days total). Compound 81 exerts direct anti-tumor properties on HT29 cells. The STING agonist Compound 81 had no growth arrest properties on normal, untransformed hTERT cells (FIG. 6D). Further, cell growth shown in FIG. 6D was monitored for 72 more hours (6 days total). Thus, in vitro, Compound 81 exhibits anti-tumor activity, likely involving an anti-tumor SASP phenotype. To evaluate the effects of Compound 81 in vivo, human HT29 cells were injected subcutaneously into nude mice that do not comprise robust adaptive immunity. The experiment was designed to evaluate the direct anti-tumor efficacy of Compound 81 against tumors, in vivo, in the absence of the adaptive immune system. When the tumors became palpable, Compound 81 was injected intratumorally (IT) or intraperitoneally (IP) subcutaneously into the mice (100 g total in 0.5% DMSO, once every 3 days for a total of three times). Results indicate that Compound 81 reduced tumor growth significantly (FIGS. 5E, 5F and 5G). Collectively, this data indicates that Compound 81 exhibits the ability to activate STING signaling and exert direct anti-tumor activity on human tumor cells.

Figure 6E:
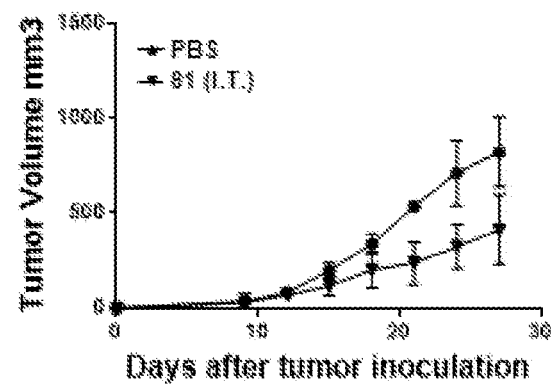
FIG. 6E shows tumor volume when palpable tumors are treated with Compound 81 (50 µg/50 µl) intratumorally (I.T.) three times every three days (nude mice (n=8) were inoculated intratumorally on the flank with $5 \times 10^5$ HT29 human cancer cells)
Figure 6F:
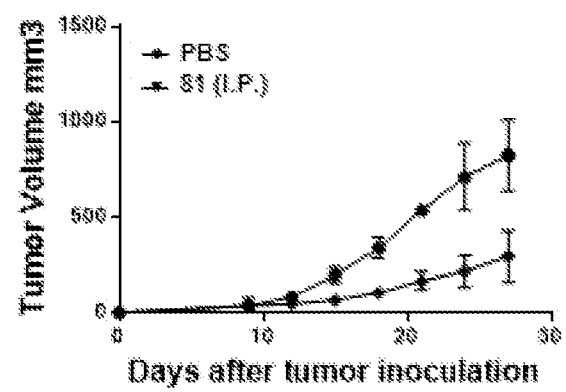
FIG. 6F shows tumor volume when palpable tumors are treated with Compound 81 (200 μg/300 μl) intraperitoneally (I.P.) three times every three days (nude mice (n=8) were inoculated intratumorally on the flank with $5 \times 10^5$ HT29 human cancer cells)

In an embodiment of the invention, a new compound that binds to and activates STING (Compound 28; 2-(4-benzylphenyl)-3-sulfanylidene-5,6,7,8-tetrahydro-[1,2,4]triazolo[1,2-a]pyridazin-1-one) was isolated. In various embodiments of the invention, based on Compound 28 a variety (over 100) novel analogues of Compound 28 have been chemically synthesized. A number of these novel analogues have been determined to retain the ability to bind to and activate STING signaling. Several retained the ability to trigger STING-dependent innate immune signaling including Compound 81 (see Tables I and II). Compound 81 exerted ability to bind to STING, to activate STING, to activate NF-κB and IRF3, to activate the transcription of STING-dependent genes, such as type I IFN, IIT, CCL5 and CLCX10 amongst others, in human cells including immune cells (FIGS. 4 and 5). Compound 81 is highly human specific as it does not bind to or activate murine STING but does function on human and monkey STING. Toxicology studies indicated that Compound 81 did not exert any off target toxicity in mice (data not shown). FIG. 6G shows a statistical evaluation demonstrating that Compound 81 exerts direct anti-tumor activity in vivo on human tumors even in the absence of adaptive immune responses (nude mice). Toxicology studies indicated that Compound 81 does not react with murine STING or exert any off target toxicity in mice. Compound 81 did not exert toxicity in vitro on normal human cells (FIG. 6D). Compound 81 was able to activate STING in human cancer cells (HT29) and exhibited the triggering of SASP and the induction of p16 leading to growth arrest and cell death (FIG. 6C). Compound 81 was found to suppress the growth of human tumors (HT29), in vivo, in nude mice (FIGS. 6D, 6E and 6F). Thus, Compound 81 can exert direct anti-suppressor activity on select cancer cells, even in the absence of adaptive immunity. In an embodiment of the invention, Compound 81 is a therapeutic agent for the treatment of cancer.

Figure 7A:
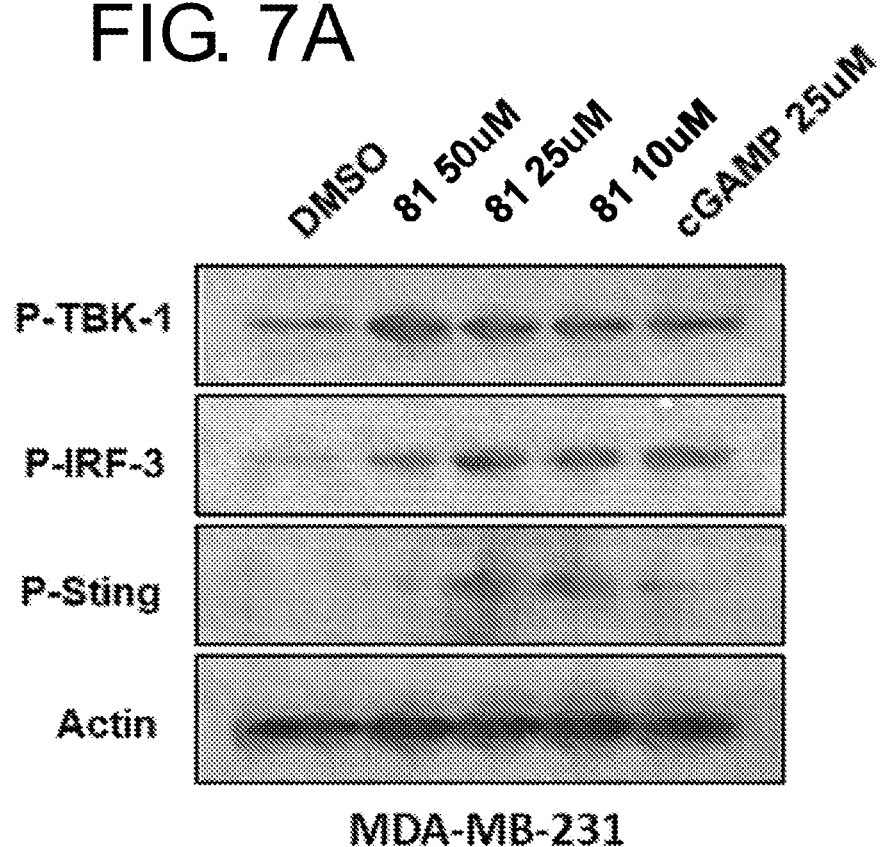
FIG. 7A shows activity of Compound 81 (0.5% DMSO) after being placed onto the human breast cancer cell MDA-MB-213 for 6 hours and phospho-TBK1, phospho-IRF3, and phospho-STING by Western Blotting.
Figure 7B:
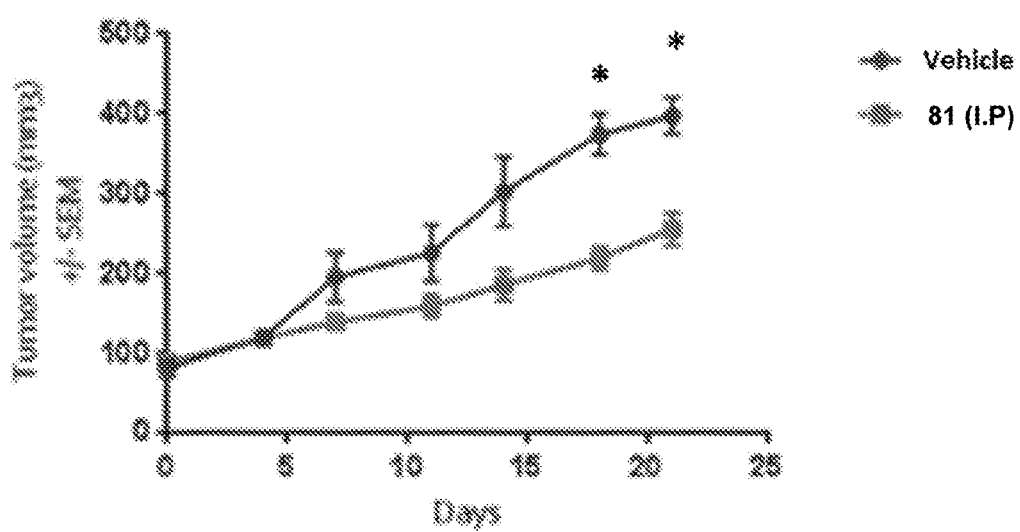
FIG. 7B shows tumor volume when palpable tumors are treated with Compound 81 (200 μg/300 ul) intraperitoneally (I.P.) three times every three days.

FIG. 7A shows activity of Compound 81 (0.5% DMSO) after being placed onto the human breast cancer cell MDA-MB-213 for 6 hours and phospho-TBK1, phospho-IRF3, and phospho-STING analyzed by Western Blotting. The results show that phospho-TBK1 was dose dependently activated by Compound 81 (approximately four fold increase in luciferase induction compared to Compound 28). FIG. 7B shows tumor volume when palpable tumors are treated with Compound 81 (200 µg/300 µl) intraperitoneally (I.P.) three times every three days. Humanized mice (hu-CD34 NSG™ SGM3) (n=5) from CD34 donors were inoculated orthotopically in the mammary fat pad with $5 \times 10^6$ MDA-MB-231 cells re-suspended in a 1:1 mixture of Matrigel with PBS or serum free media.

Example 6

Cell culture. Normal human cell and human cancer cell lines (HT-29) were purchased from Lozna and ATCC respectively and cultured in their appropriate growth media according to the instructions. Media and supplements are from Invitrogen. hTERT-BJ1 Telomerase Fibroblasts (hTERT) were originally purchased from Clontech and were cultured in 4:1 ratio of DMEM:Medium 199 supplement with 10% FBS, 4 mM L-Glutamine and 1 mM sodium pyruvate at 37° C. in a 5% $CO_2$-humidified atmosphere. hTERT-BJ1 Telomerase Fibroblasts stably expressing the luciferase gene under the control of the interferon-beta promoter and SEAP gene under control of the CMV promoter) (hTERT-pIFNβ-Glu) were generated by the Barber laboratory. Human PBC's and macrophages were isolated as described in Ahn, et. al., Cancer Cell. 2018, 33(5), 862-873, which is herein incorporated by reference in its entirety and for all purposes.

Example 7

Purification of STING protein for binding assay. DNA sequence encoding human STING CBD-CTT (152-379) was inserted into pET 26b-6λHis-pelB (-) vector between NdeI/XhoI sites (STING152-379H). Protein was expressed in E. coli BL21 DE3 RIPL Codon Plus cell. E. coli cell was induced by 0.2 mM IPTG, when cell density reached 0.5-0.6 and grew at 10° C. overnight. Cells were spun down and lysed in lysis buffer (20 mM Tris pH7.5, 300 mM NaCl, 5 mM DTT and Protease Inhibitor Cocktail Tablets (Complete EDTA-Free-Roche 11873580001). Protein lysate was French Pressed (10-15 times) using the EmulsiFlex-C3 French Press (Avestin, Inc.), Imidazole was added to a final concentration of 50 mM. Cell debris was removed by centrifugation at 20,000 rpm, 4° C. Supernatant was applied, at a very slow rate, to a 5 mL HisTrap HP columns (GE Healthcare 17-5247-01). Before applying cell lysate, the column was equilibrated with the Lysis Buffer containing 50 mM Imidazole. Column containing the STING Protein was washed extensively using 3 column volumes of Lysis/Binding buffer. Protein was eluted with elution buffer (20 mM Tris pH7.5, 300 mM NaCl, 5 mM DTT, 300 mM Imidazole). Eluted fraction was applied in an S200 Chromatography Column to isolate pure STING Dimer. Fraction containing STING protein dimer was pooled, concentrated, and flash frozen for future use.

FIG. 8A shows a human STING protein structure. C-terminal portion from AA 152-379 (237aa long) was cloned into the pET26B vector NdeI-XhoI sites (STING152-379H); and FIG. 8B shows STING152-379H that was purified over a nickel column as described in materials and methods. Size Exclusion Chromatography on eluted samples was then carried out using a SEC 200 Column. Using the calibration curve, the major peak (arrow, 60 kDa) signifies dimers of STING 152-379 (predicted MW of the dimer is approximately 57 kDa). Protein gel (non-denaturing) shows eluted dimer, (1 and 2 µM of 50 mg/ml protein stock).

Example 8

Thermal high throughput screen. The denaturation profile of purified STING (STING152-379H) was calibrated using a fluorometer equipped with temperature control (a qPCR apparatus with 320 well capacity). Once this was established, purified STING (5 µL; 1 µM) was mixed with 2.5 µL DMSO and compound (1% DMSO final with 2.5% SYPRO orange). The total reaction mixture was 10 µL in 50 µM HEPES and 100 mM NaCl. SYPRO Orange binds nonspecifically to hydrophobic surfaces. When the protein unfolds, the exposed hydrophobic surfaces bind the dye, resulting in an increase in fluorescence by excluding water. The stability curve and its midpoint value (melting temperature, Tm also known as the temperature of hydrophobic exposure, Th) was obtained by gradually increasing the temperature to unfold the protein and measuring the fluorescence at each point. Curves were measured for STING only and STING+small molecule, and ΔTm was calculated. The temperature ramp was 0.1 Centigrade/second. Approximately 250,000 compounds were screened from the EMININE stock collection of compounds. Novel analogues of lead hits were generated by Enamine using standard chemistry procedures.

Example 9

Immunoblot analysis. Equal amounts of proteins were resolved on sodium dodecyl sulfate (SDS)-Polyacrylamide gels and then transferred to polyvinylidene fluoride (PVDF) membranes (Millipore). After blocking with 5% Blocking Reagent, membranes were incubated with various primary antibodies (and appropriate secondary antibodies). The image was resolved using an enhanced chemiluminescence system ECL (Thermo Scientific) and detected by autoradiography (Kodak). Antibodies: rabbit polyclonal antibody against STING was developed in our laboratory as described previously in Ishikawa et al., 2008; other antibodies were obtained from following sources: β-actin (Sigma Aldrich), p-IRF3 (Cell Signaling), IRF3 (Santa Cruz Biotechnology), p-p65 (Cell Signaling), p65 (Cell Signaling), p-TBK1 (Cell Signaling), TBK1 (Abcam), cGAS (Cell Signaling).

Example 10

Interferon β RELISA analysis. Interferon β RELISA was performed using either the IFNβ human ELISA Kit from Invitrogen or the Human IFNβ ELISA Kit from PBL Interferon Source following the manufacturer's protocol.

Example 11

Immunofluorescence microscopy. Cells were cultured and treated in their appropriate media on Lab-Tek II chamber slides. Cell were fixed with 4% paraformaldehyde for 15 minutes in at 37° C. and permeabilized with 0.05% Triton X-100 for 5 minutes at room temperature. Immunostaining was performed with rabbit-anti-STING polyclonal, rabbit-anti-IRF3 (Santa Cruz Biotechnology) or rabbit-anti-p65 (Cell Signaling) followed by fluorescence conjugated secondary antibodies (FITC-goat-anti-rabbit) (Invitrogen). Images were taken with Leika LSM confocal microscope.

Example 12

Quantitative real-time PCR (qPCR). Total RNA was reverse transcribed using QuantiTect Reverse Transcription Kit (Qiagen). Real-time PCR was performed with the TaqMan gene Expression Assay (Applied Biosystems).
Total RNA were reverse-transcribed using M-MLV Reverse Transcriptase (Promega). Real-time PCR was performed using Taqman Gene Expression Assay (Applied Biosystems) for innate immune genes and inflammatory cytokines (IFNβ: Mm010439546, TNF: Mm00443258, IL6: Mm00446190, IL1β: Mm01336189, Cxcl10: Mm00445235, IFIT3: Mm0170846, ICAM1: Mm00516023, Cxcr3: Mm1249867).

Example 13

SASP analysis. SASP analysis was carried out as described in Takahashi et al Nat. Commun. 2018, 9(1), 1249 which is herein expressly incorporated by reference in its entirety and for all purposes.

Example 14

Mouse treatment. Balb/C nu/nu mice were purchased from Charles River and maintained in the institutional Division of Veterinary Resources (DVR). All experiments were performed with institutional animal care and use committee (IACUC) approval and in compliance with IACUC guidelines. Tumor cells (HT29) were introduced in the flanks of Balb/c nude mice by subcutaneous injection of 5E105 of the appropriate tumor cells and tumors allowed to develop to an average diameter of approximately 0.5 cm. 100 g/μL of Compound 81 (in 0.5% DMSO) was used to treat mice. DMSO (0.5%) was used as vehicle control. Effect on tumor growth was monitored. Mice were euthanized when tumor diameter exceeded 10 mm.

Example 15

Statistical analysis. All statistical analysis was performed by Student's t test unless specified. The data were considered to be significantly different when P<0.05. Human STING c-terminal portion amino acid sequence 152-379 SEQ. ID. 1 MNFNVAHGLA WSYYIGYLRL ILPELQARIR TYNQHYNNLL RGAVSQRLYI LLPLDCGVPD NLSMADPNIR FLDKLPQQTG DHAGIKDRVY SNSIYELLEN GQRAGTCVLE YATPLQTLFA MSQYSQAGFS REDRLEQAKL FCR-TLEDILA DAPESQNNCR LIAYQEPADD SSFSLSQEVL RHLRQEEKEE VTVGSLKTSA VPSTSTMSQE PELLIS-GMEK PLPLRTDFSL EHHHHHH with a 6×His-Tag tail at the carboxyl end of the sequence (STING152-379H).

Example 16

Synthesis of Compound 81. A mixture of 5-(4-ethylphenyl)-4H-1,2,4-triazole-3-thiol (910) (0.0289 g, 0.14 mmol), 2-bromo-1-(3-fluorophenyl)propan-1-one (920) (0.039 g, 0.168 mmol) and N-ethyl-N-isopropylpropan-2-amine (930) (0.0636 g, 0.492 mmol) in DMF (4 mL) was heated at 60° C. for 12 h (940). After cooling to room temperature water (20 mL) and ethyl acetate (20 mL) were added to the mixture. The product was extracted with ethyl acetate (3×10 mL). The organic phases were combined, washed with brine, dried over sodium sulfate and concentrated. The residue was purified by reverse phase HPLC (water/acetonitrile) to afford Compound 81.

Example 17

Figure 10A:
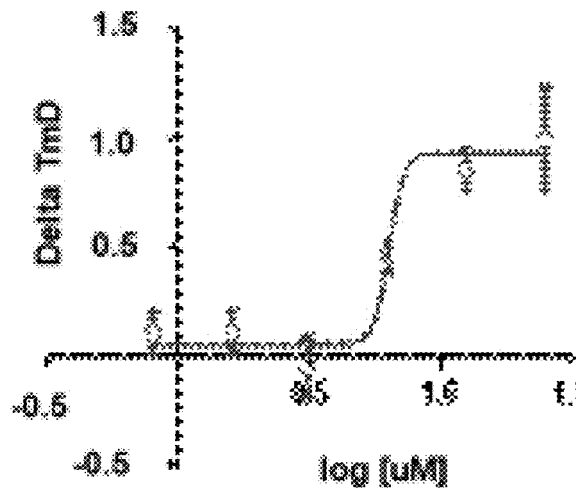
FIG. 10A shows cGAMP binding to the CDN binding domains of human STING (140-379)
Figure 10B:
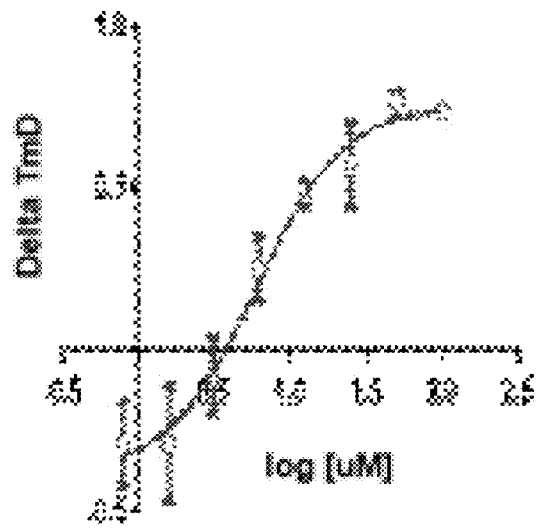
FIG. 10B shows Compound 81 binding to the CDN binding domains of human STING (140-379).

Evaluation of selectivity to human STING of Compound 8 using TSA. CDN binding domains of human STING (140-379) was purified by *E. coli* recombinant expression system. FIG. 10A shows 8 points 2-fold serial dilutions of cGAMP mixed with STING protein and 2×SYPRO orange dye mix. The Kd value for cGAMP binding to the CDN binding domains of human STING (140-379) was 6.3. FIG. 10B shows 8 points 2-fold serial dilutions of Compound 81 mixed with STING protein and 2×SYPRO orange dye mix. Compound 81 binding to the CDN binding domains of human STING (140-379) had a Kd of 5.9. Raw data was analyzed using ViiA7 and Protein Thermal Shift Software. The Kd values were calculated by plotting the delta TmD in GraphPad PRISM.

EQUIVALENTS

Those skilled in the art will recognize, or be able to ascertain using no more than routine experimentation, many equivalents to the specific embodiments and methods described herein. Such equivalents are intended to be encompassed by the scope of the present application. All patents, patent applications, and literature references cited herein are hereby expressly incorporated by reference.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. For example, it is envisaged that, irrespective of the actual shape depicted in the various Figures and embodiments described above, the outer diameter exit of the inlet tube can be tapered or non-tapered and the outer diameter entrance of the outlet tube can be tapered or non-tapered.

Thus, the breadth and scope of the present invention should not be limited by any of the above-described exem- Specific Embodiments Embodiments contemplated herein include embodiments P1-P30 following.

Embodiment P1

A compound of Formula Ip:

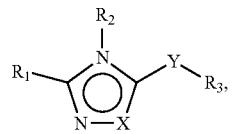

(Ip)

or a pharmaceutically acceptable salt, hydrate, solvate, prodrug, stereoisomer, or tautomer thereof, where:
- $R_1$ is $(C_1\text{-}C_6)$ alkyl, $(C_3\text{-}C_6)$ cycloalkyl, $(C_5\text{-}C_{10})$ aryl, or 5- to 14-membered heterocyclyl including 1-5 heteroatoms selected from N, O and S, where the alkyl, cycloalkyl, aryl or heterocyclyl is optionally substituted with one or more $R_{1a}$;
- each $R_{1a}$ is independently $(C_1\text{-}C_6)$ alkyl, $(C_3\text{-}C_6)$ cycloalkyl, $(C_1\text{-}C_6)$ haloalkyl, $(C_1\text{-}C_6)$ alkoxy, $(C_1\text{-}C_6)$ haloalkoxy, $(C_2\text{-}C_6)$ alkenyl, $(C_2\text{-}C_6)$ alkynyl, halogen, nitro, CN, oxo, $B(OH)_2$, OH, COOH, SH, $NH_2$, $NH(C_1\text{-}C_4)$ alkyl, or $N((C_1\text{-}C_4)$ alkyl$)_2$;
- $R_2$ is H, $(C_1\text{-}C_4)$ alkyl, or $(C_5\text{-}C_{10})$ aryl, where the alkyl or aryl is optionally substituted by OH, alkoxy, or halogen;
- X is —N— or —O—, provided when X is —O—, $R_2$ is absent;
- Y is a direct bond, —$NR_{xa}$—, —O—, or —S—;
- $R_{xa}$ is H, $(C_1\text{-}C_6)$ alkyl, $(C_3\text{-}C_6)$ cycloalkyl, $(C_5\text{-}C_{10})$ aryl, or 5- to 14-membered heterocyclyl including 1-5 heteroatoms selected from N, O and S;
- $R_3$ is $(C_3\text{-}C_6)$ cycloalkyl or $(C_1\text{-}C_6)$ alkyl, where the cycloalkyl or alkyl is optionally substituted with one or more halogen, —$OR_4$, oxo, —$NHS(O)_2R_4$, or $R_4$;
- each $R_4$ is independently H, $(C_5\text{-}C_{10})$ aryl, $(C_5\text{-}C_{10})$ cycloalkyl, $(C_5\text{-}C_{10})$ heteroaryl, or 5- to 14-membered heterocyclyl including 1-5 heteroatoms selected from N, O and S, where the aryl, heteroaryl, or heterocyclyl is optionally substituted with one or more $(C_5\text{-}C_{10})$ aryl, $(C_1\text{-}C_6)$ alkyl, $(C_3\text{-}C_6)$ cycloalkyl, $(C_1\text{-}C_6)$ haloalkyl, $(C_1\text{-}C_6)$ alkoxy, $(C_1\text{-}C_6)$ haloalkoxy, $(C_2\text{-}C_6)$ alkenyl, $(C_2\text{-}C_6)$ alkynyl, halogen, nitro, —CN, oxo, —$B(OH)_2$, —OH, —COOH, —SH, —$NH_2$, —$NH(C_1\text{-}C_4)$ alkyl, —$N((C_1\text{-}C_4)$ alkyl$)_2$, or —$(CH_2)_nNC(O)(C_1\text{-}C_4)$ alkyl, where n is 0, 1, 2, or 3.

Embodiment P2

The compound of embodiment P1, where Formula (Ip) is of Formula Ipa:

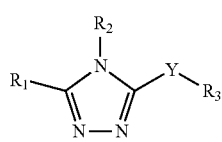

(Ipa)

or a pharmaceutically acceptable salt, hydrate, solvate, prodrug, stereoisomer, or tautomer thereof.

Embodiment P3

The compound of embodiments P1 or P2, where Y is —$NR_{xa}$—, —O—, or —S—.

Embodiment P4

The compound of embodiments P1 to P3, where Y is —S—.

Embodiment P5

The compound of any proceeding embodiments P1 to P4, where $R_1$ is selected from the group consisting of

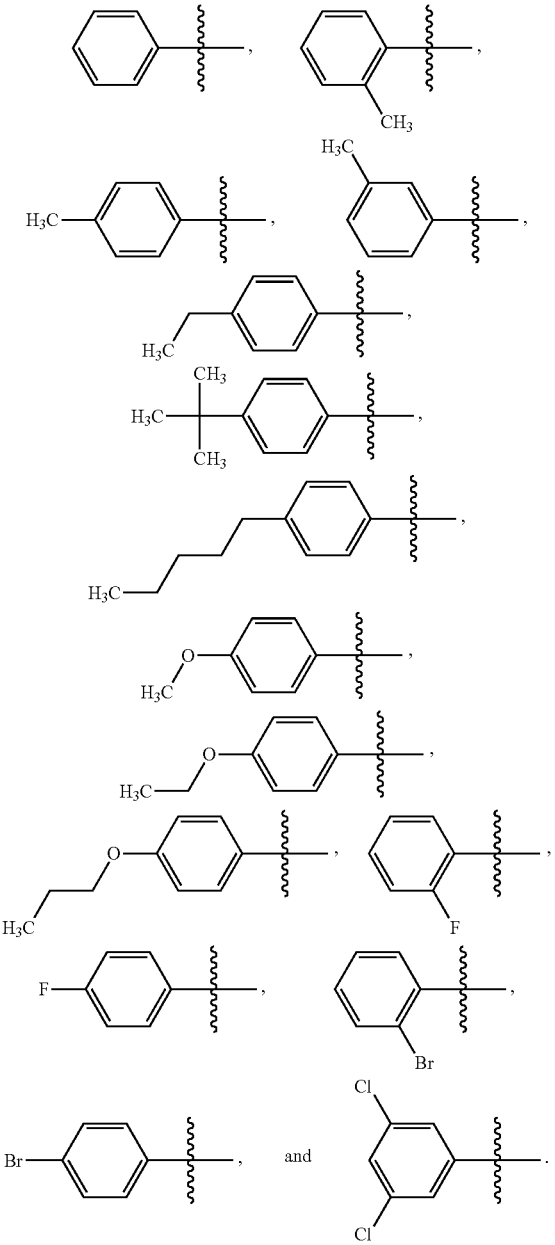

Embodiment P6
The compound of any embodiments P1 to P5, where Formula (Ip) is of Formula (Ipb) or (Ipc),
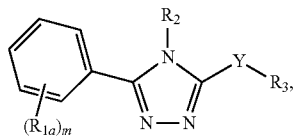
(Ipb)
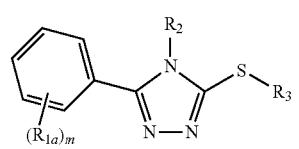
(Ipc)
or a pharmaceutically acceptable salt, hydrate, solvate, prodrug, stereoisomer, or tautomer thereof, where m is 0, 1, 2, 3, 4 or 5.
Embodiment P7
The compound of any proceeding embodiments P1 to P6, where $R_3$ is selected from the group consisting of
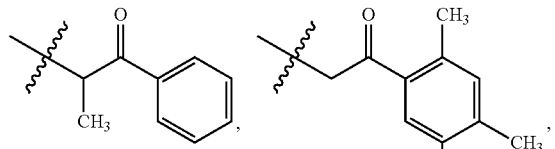
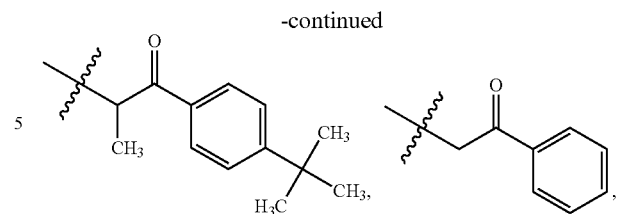
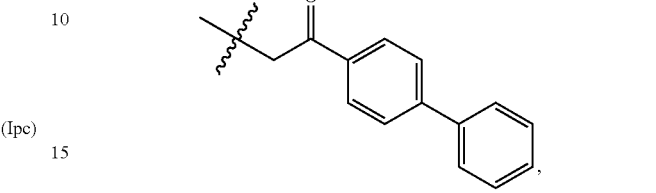
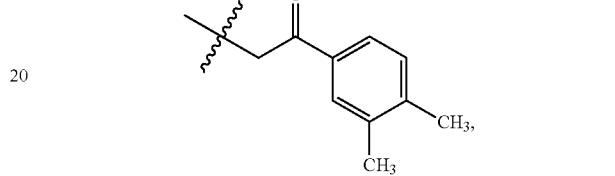
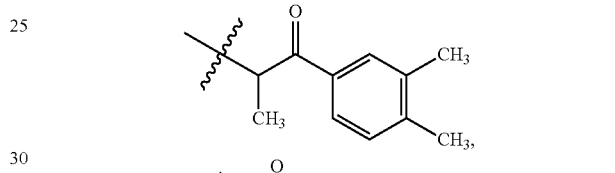
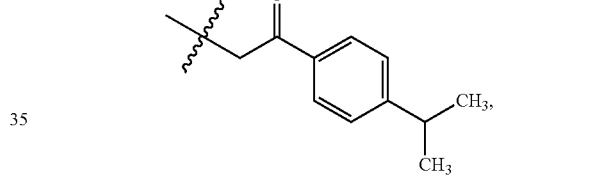
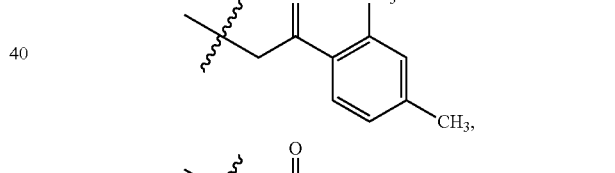
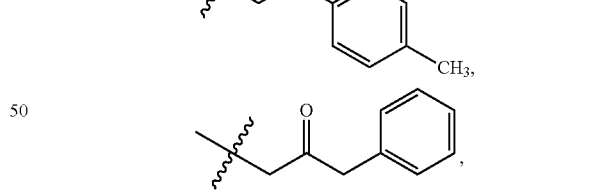
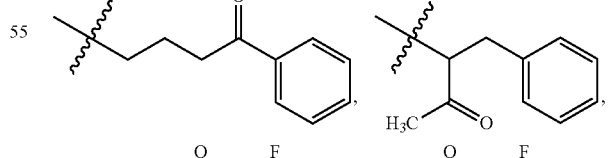
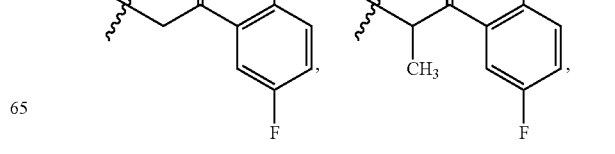

-continued

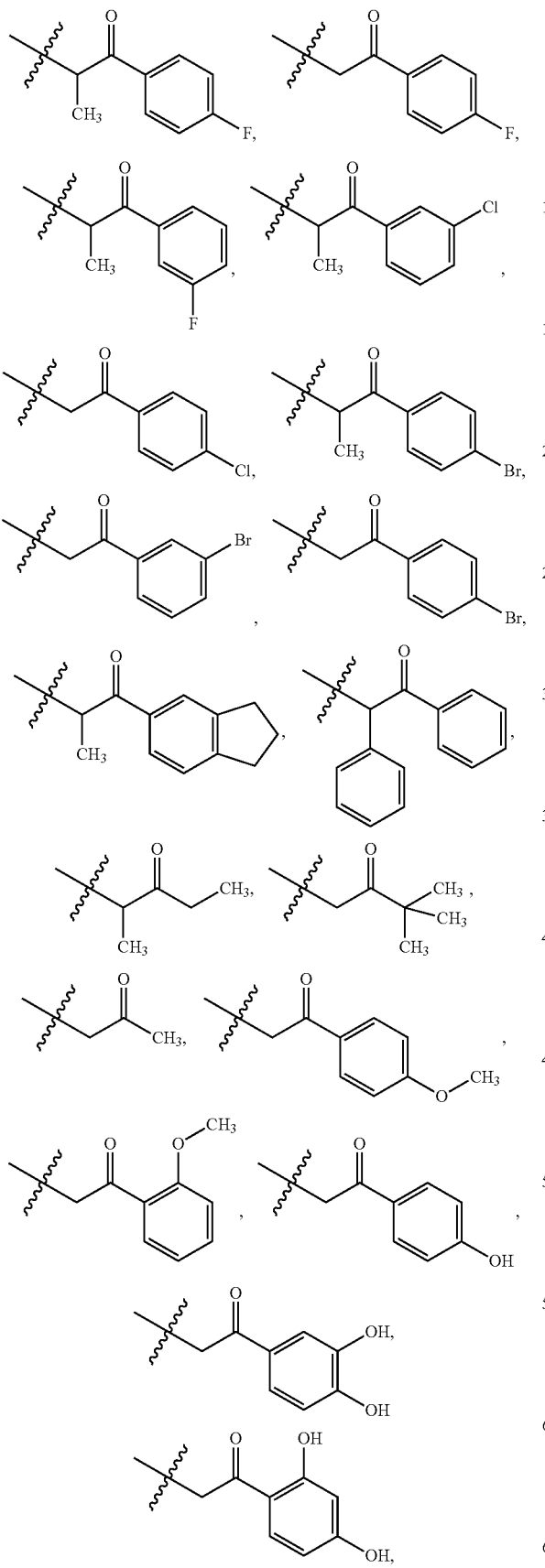

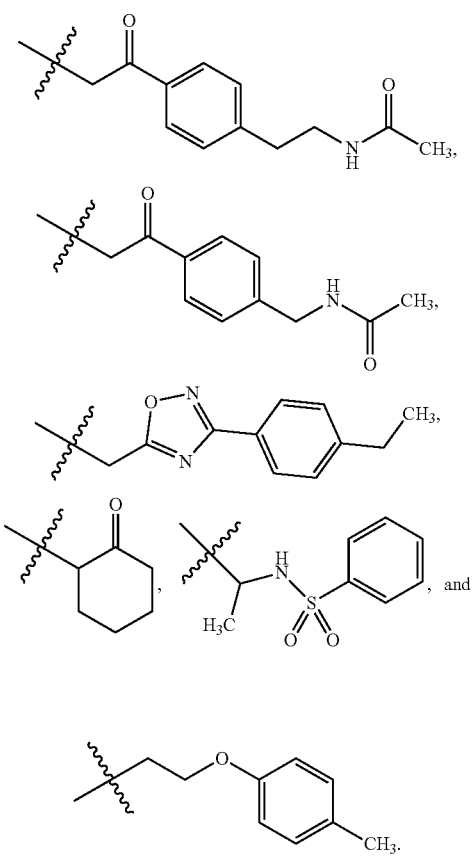

Embodiment P8

The compound of any proceeding embodiments P1 to P7, where Formula (Ip) is a compound of Formula (Ipd) or (Ipe),

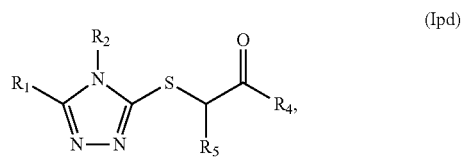

(Ipd)

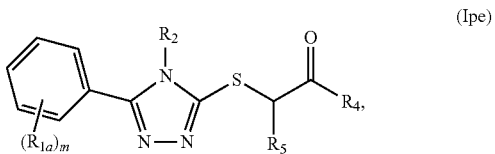

(Ipe)

or a pharmaceutically acceptable salt, hydrate, solvate, prodrug, stereoisomer, or tautomer thereof, where $R_5$ is H, $(C_1\text{-}C_6)$ alkyl, $(C_5\text{-}C_{10})$ aryl, where the alkyl, or aryl is optionally substituted with $(C_5\text{-}C_{10})$ aryl, $(C_1\text{-}C_6)$ alkyl, $(C_1\text{-}C_6)$ alkoxy, $(C_3\text{-}C_6)$ cycloalkyl, $(C_1\text{-}C_6)$ haloalkyl, $(C_1\text{-}C_6)$ alkoxy, halogen, or oxo, and m is 0, 1, 2, 3, 4 or 5.

Embodiment P9

The compound of any proceeding embodiments P1 to P8, where Formula (Ip) is a compound of Formula (Ipf),

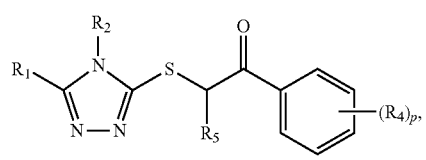

(Ipf)

or a pharmaceutically acceptable salt, hydrate, solvate, prodrug, stereoisomer, or tautomer thereof, where p is 0, 1, 2, 3, 4, or 5.

Embodiment P10

The compound of any preceding embodiments P1 to P9, where Formula (Ip) is a compound of Formula (Ipg),

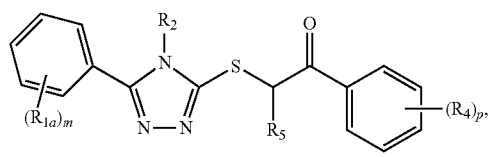

(Ipg)

or a pharmaceutically acceptable salt, hydrate, solvate, prodrug, stereoisomer, or tautomer thereof where m is 0, 1, 2, 3, 4 or 5 and p is 0, 1, 2, 3, 4, or 5.

Embodiment P11

The compound of any preceding embodiments P1 to P10, where $R_4$ is selected from the group consisting of

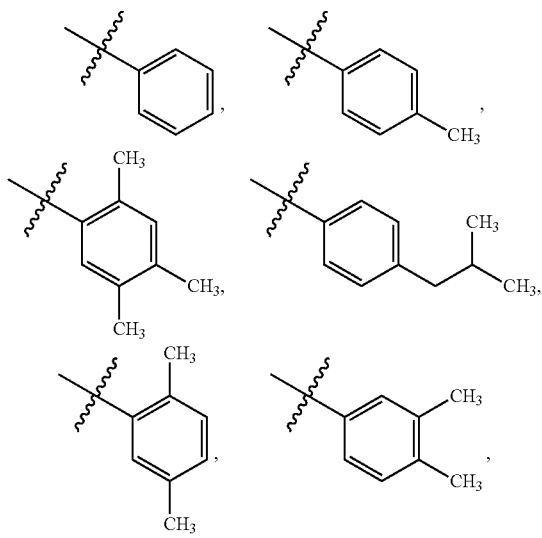

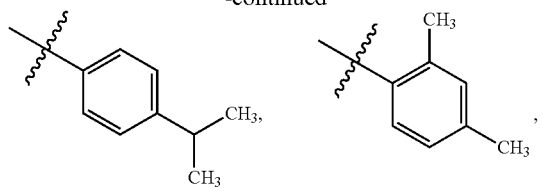

Embodiment P12

The compound of any preceding embodiments P1 to P11, where $R_5$ is selected from the group consisting of H, $(C_1-C_6)$ alkyl.

Embodiment P13

The compound of any preceding embodiments P1 to P12, where m is 1 or 2.

Embodiment P14

The compound of any preceding embodiments P1 to P13, where p is 1 or 2.

Embodiment P15

The compound of any preceding embodiments P1 to P14, where p is 1 or 2 and m is 1 or 2.

Embodiment P16

The compound of any preceding embodiments P1 to P15, where m is 1 and p is 1

Embodiment P17

A compound selected from Table I.

Embodiment P18

A pharmaceutical composition including a therapeutically effective amount of a compound of any one of the preceding embodiments or a pharmaceutically acceptable salt thereof, and a pharmaceutically acceptable carrier.

Embodiment P19

A method of modulating a stimulator of interferon genes (STING) protein, including administering to a subject in need thereof a therapeutically effective amount of a compound of any one of the preceding embodiments or a pharmaceutically acceptable salt thereof, or the pharmaceutical composition of embodiment P18.

Embodiment P20

A method of treating or preventing a disease, where the diseases is caused by, or associated with, STING expression, activity, and/or function, or is associated with deregulation of one or more of the intracellular pathways in which a STING protein is involved, including administering to the subject a therapeutically effective amount of a compound of any one of the preceding embodiments or a pharmaceutically acceptable salt thereof, or the pharmaceutical composition of embodiment P18.

Embodiment P21

A compound of any one of the preceding embodiments P18 to P20 or a pharmaceutically acceptable salt or ester thereof, or the pharmaceutical composition of embodiment P18, for use in modulating a STING protein, or in treating or preventing a disease caused by, or associated with, STING expression, activity, and/or function, or associated with deregulation of one or more of the intracellular pathways in which a STING protein is involved.

Embodiment P22

A compound of any one of the preceding embodiments P18 to P21 or a pharmaceutically acceptable salt or ester thereof, or the pharmaceutical composition of embodiment P18, for use in the manufacture of a medicament for modulating a STING protein, or for treating or preventing a disease caused by, or associated with, STING expression, activity, and/or function, or associated with deregulation of one or more of the intracellular pathways in which a STING protein is involved.

Embodiment P23

Use of a compound of any one of the preceding embodiments P18 to P22 or a pharmaceutically acceptable salt thereof, or the pharmaceutical composition of embodiment P18, in the manufacture of a medicament for modulating STING, for treating or preventing a disease, or for treating or preventing cancer in a subject, where the subject is identified as being in need of STING modulation for the treatment or prevention of cancer.

Embodiment P24

Use of a compound of any one of the preceding embodiments P18 to P23 or a pharmaceutically acceptable salt thereof, or the pharmaceutical composition of embodiment P18, in the manufacture of a medicament for modulating STING, for treating or preventing a disease, or for treating or preventing cancer in a subject, where the subject is identified as being in need of immune system modulation for the treatment or prevention of cancer.

Embodiment P25

Use of a compound of any one of the preceding embodiments P18 to P24 or a pharmaceutically acceptable salt thereof, or the pharmaceutical composition of embodiment P18, in the manufacture of a medicament for modulating STING, for treating or preventing a disease, or for treating or preventing cancer in a subject, where the subject is identified as being in need of activating STING for the treatment or prevention of cancer.

Embodiment P26

A kit including a compound of any one of the preceding embodiments P18 to P25, or a pharmaceutically acceptable salt or ester thereof, or the pharmaceutical composition of embodiment P18.

Embodiment P27

A method for treating a subject, wherein the subject is suffering from cancer, the method including the steps of: a) determining whether the subject has a defective functional activity of Stimulator of Interferon Genes (STING) by: isolating a sample from the subject having cancer; and performing a PCR assay on the sample to determine if a cell population has a defective functional activity of STING; b) if the subject has a defective functional activity of STING, then identifying a selected therapy, wherein the selected therapy is administering one or more compounds of Table I; and c) internally treating the subject with the selected therapy.

Embodiment P28

A method for treating a subject, wherein the subject is suffering from cancer, the method including the steps of: a) determining whether the subject has a defective functional activity of Stimulator of Interferon Genes (STING) by: isolating a sample from the subject having cancer; and performing a PCR assay on the sample to determine if a cell population has a defective functional activity of STING; b) if the subject has a defective functional activity of STING, then identifying a selected therapy, wherein the selected therapy is administering a pharmaceutical composition including a therapeutically effective amount of a compound of Table I or a pharmaceutically acceptable salt thereof, and a pharmaceutically acceptable carrier; and c) internally treating the subject with the selected therapy.

Embodiment P29

A method for treating a subject, where the subject is suffering from cancer, the method including the steps of: a) determining whether the subject has a defective functional activity of cyclic Guanosine Monophosphate (cGMP)-Adenosine Monophosphate (AMP) Synthase (cGAS) by; isolating a sample from the subject having cancer; and performing a PCR assay on the sample to determine the cellular levels of one or more mRNA's selected from the group consisting of Interleukin-1 (IL-1), IL-3, IL-18 and IL-22 to determine if a cell population has a defective functional activity of cGAS; b) if the subject has a defective functional activity of cGAS, then selecting a therapy where the selected therapy is administering one or more compounds of Table I; and c) internally treating the subject with the selected therapy.

Embodiment P30

A method for treating a subject, where the subject is suffering from cancer, the method including the steps of: a) determining whether the subject has a defective functional activity of cyclic Guanosine Monophosphate (cGMP)-Adenosine Monophosphate (AMP) Synthase (cGAS) by; isolating a sample from the subject having cancer; and performing a PCR assay on the sample to determine the cellular levels of one or more mRNA's selected from the group consisting of Interleukin-1 (IL-1), IL-3, IL-18 and IL-22 to determine if a cell population has a defective functional activity of cGAS; b) if the subject has a defective functional activity of cGAS, then selecting a therapy, where the selected therapy is administering a pharmaceutical composition including a therapeutically effective amount of a compound of Table I or a pharmaceutically acceptable salt thereof, and a pharmaceutically acceptable carrier; and c) internally treating the subject with the selected therapy.

Embodiments contemplated herein include embodiments Q1-Q28 following.

Embodiment Q1

A compound of Formula I:

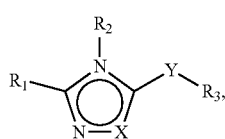

(I)

or a pharmaceutically acceptable salt, hydrate, solvate, prodrug, stereoisomer, or tautomer thereof, where:
$R_1$ is $(C_1-C_6)$ alkyl, $(C_3-C_6)$ cycloalkyl, $(C_5-C_{10})$ aryl, or 5-to 14-membered heterocyclyl including 1-5 heteroatoms selected from N, O and S, where the alkyl, cycloalkyl, aryl or heterocyclyl is optionally substituted with one or more $R_{1a}$;
each $R_{1a}$ is independently $(C_1-C_6)$ alkyl, $(C_3-C_6)$ cycloalkyl, $(C_1-C_6)$ haloalkyl, $(C_1-C_6)$ alkoxy, $(C_1-C_6)$ haloalkoxy, $(C_2-C_6)$ alkenyl, $(C_2-C_6)$ alkynyl, halogen, nitro, CN, oxo, $B(OH)_2$, OH, COOH, SH, $NH_2$, $NH(C_1-C_4)$ alkyl, or $N((C_1-C_4)$ alkyl$)_2$;
$R_2$ is H, $(C_1-C_4)$ alkyl, $SO_2-(C_1-C_{12})$-alkyl, or $(C_5-C_{10})$ aryl, where the alkyl or aryl is optionally substituted by OH, alkoxy, or halogen;
X is —N— or —O—, provided when X is —O—, $R_2$ is absent;
Y is a direct bond, $-NR_{xa}-$, $-O-$, or $-S-$;
$R_{xa}$ is H, $(C_1-C_6)$ alkyl, $(C_3-C_6)$ cycloalkyl, $(C_5-C_{10})$ aryl, or 5-to 14-membered heterocyclyl including 1-5 heteroatoms selected from N, O and S;
$R_3$ is $(C_3-C_6)$ cycloalkyl or $(C_1-C_6)$ alkyl, where the cycloalkyl or alkyl is optionally substituted with one or more halogen, $-OR_4$, oxo, $-NHS(O)_2R_4$, or $R_4$;
each $R_4$ is independently H, $(C_5-C_{10})$ aryl, $(C_5-C_{10})$ cycloalkyl, $(C_5-C_{10})$ heteroaryl, or 5-to 14-membered heterocyclyl including 1-5 heteroatoms selected from N, O and S, where the aryl, heteroaryl, or heterocyclyl is optionally substituted with one or more $(C_5-C_{10})$ aryl, $(C_1-C_6)$ alkyl, $(C_3-C_6)$ cycloalkyl, $(C_1-C_6)$ haloalkyl, $(C_1-C_6)$ alkoxy, $(C_1-C_6)$ haloalkoxy, $(C_2-C_6)$ alkenyl, $(C_2-C_6)$ alkynyl, halogen, nitro, —CN, oxo, —B(OH)$_2$, —OH, —COOH, —SH, —NH$_2$, —NH(C$_1$-C$_4$) alkyl, —N((C$_1$-C$_4$) alkyl)$_2$, or —(CH$_2$)$_n$NC(O)(C$_1$-C$_4$) alkyl, where n is 0, 1, 2, or 3.

Embodiment Q2

The compound of embodiment Q1, where Formula (I) is of Formula Ia:

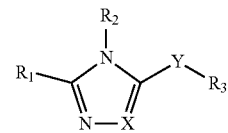

(Ia)

or a pharmaceutically acceptable salt, hydrate, solvate, prodrug, stereoisomer, or tautomer thereof.

Embodiment Q3

The compound of embodiments Q1 or Q2, where Y is $-NR_{xa}-$, $-O-$, or $-S-$.

Embodiment Q4

The compound of embodiments Q1 to Q3, where Y is $-S-$.

Embodiment Q5

The compound of any proceeding embodiments Q1 to Q4, where $R_1$ is selected from the group consisting of

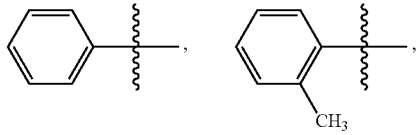

-continued
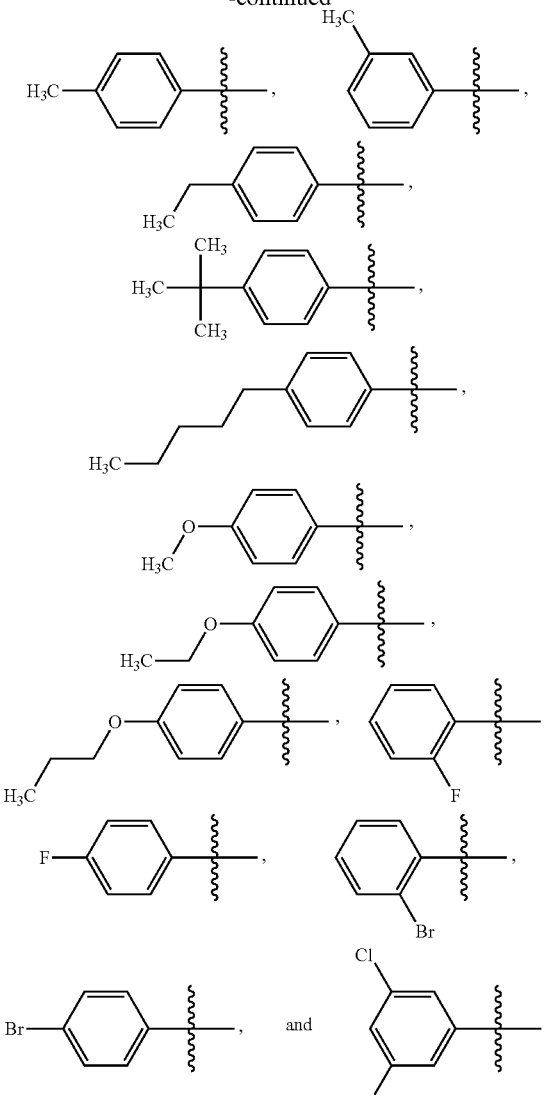
Embodiment Q6
The compound of any embodiments Q1 to Q5, where Formula (I) is of Formula (Ib) or (Ic),
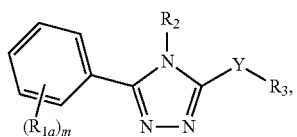
(Ib)
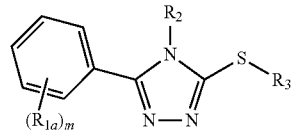
(Ic)
or a pharmaceutically acceptable salt, hydrate, solvate, prodrug, stereoisomer, or tautomer thereof, where m is 0, 1, 2, 3, 4 or 5.
Embodiment Q7
The compound of any proceeding embodiments Q1 to Q6, where $R_3$ is selected from the group consisting of
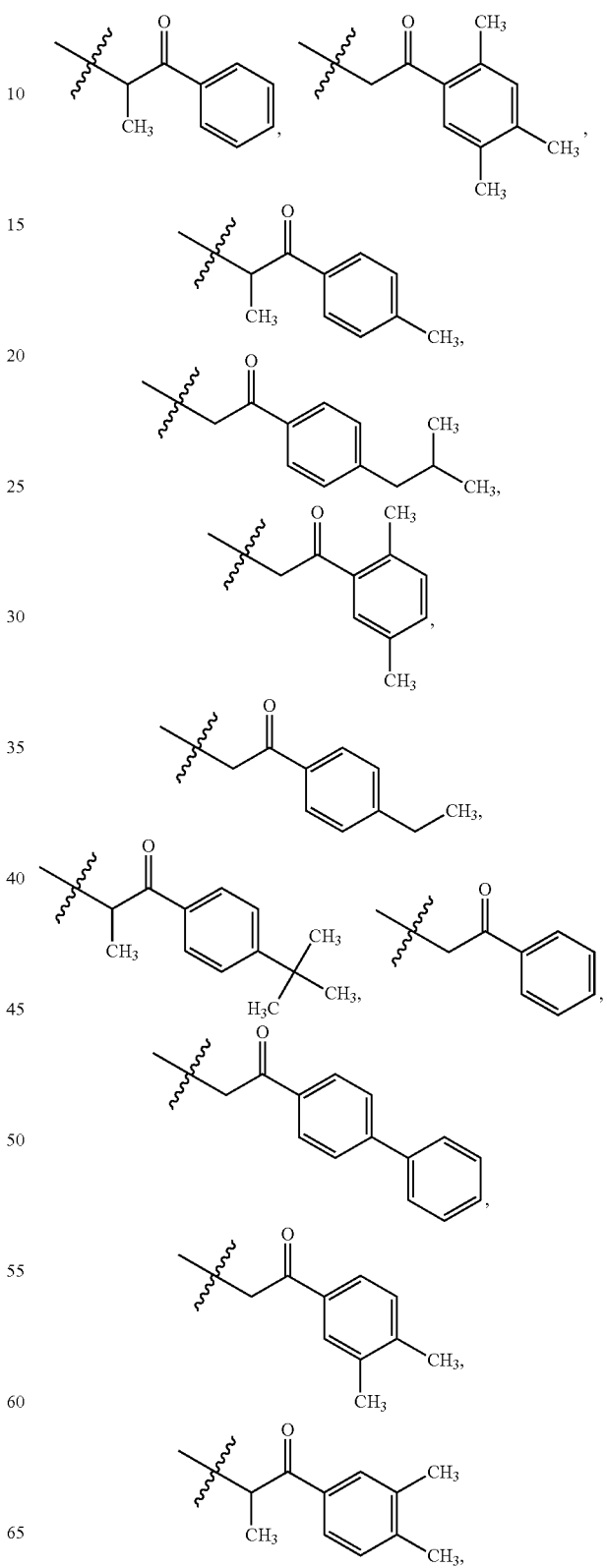

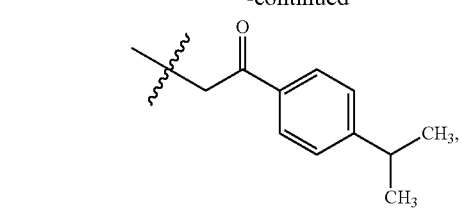
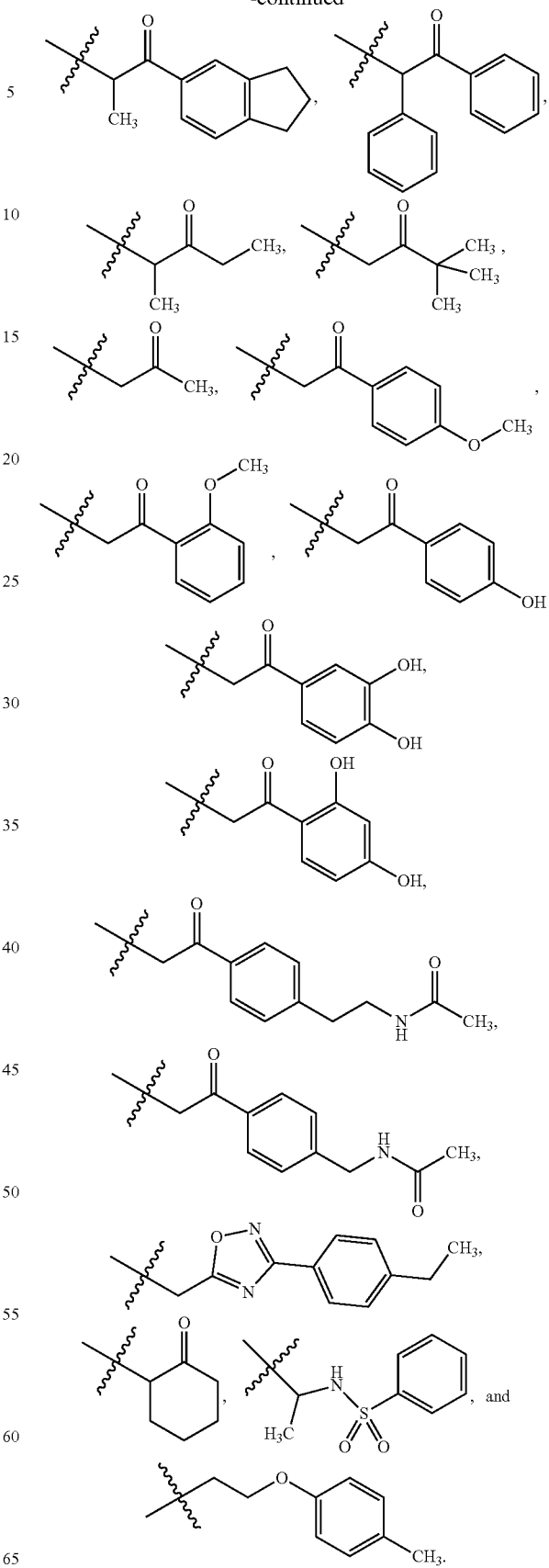

Embodiment Q8

The compound of any proceeding embodiments Q1 to Q7, where Formula (I) is a compound of Formula (Id) or (e),

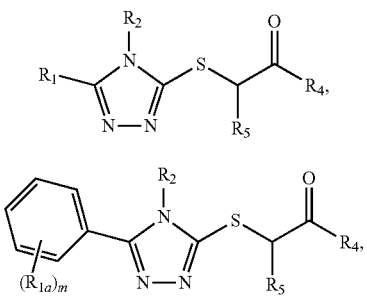

(Id)

(Ie)

or a pharmaceutically acceptable salt, hydrate, solvate, prodrug, stereoisomer, or tautomer thereof, where $R_5$ is H, $(C_1-C_6)$ alkyl, $(C_5-C_{10})$ aryl, where the alkyl, or aryl is optionally substituted with $(C_5-C_{10})$ aryl, $(C_1-C_6)$ alkyl, $(C_1-C_6)$ alkoxy, $(C_3-C_6)$ cycloalkyl, $(C_1-C_6)$ haloalkyl, $(C_1-C_6)$ alkoxy, halogen, or oxo, and m is 0, 1, 2, 3, 4 or 5.

Embodiment Q9

The compound of any proceeding embodiments Q1 to Q8, where Formula (I) is a compound of Formula (If),

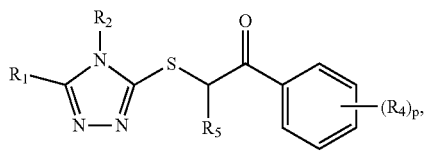

(If)

or a pharmaceutically acceptable salt, hydrate, solvate, prodrug, stereoisomer, or tautomer thereof, where p is 0, 1, 2, 3, 4, or 5.

Embodiment Q10

The compound of any preceding embodiments Q1 to Q9, where Formula (I) is a compound of Formula (Ig),

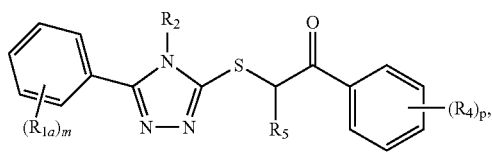

(Ig)

or a pharmaceutically acceptable salt, hydrate, solvate, prodrug, stereoisomer, or tautomer thereof where m is 0, 1, 2, 3, 4 or 5 and p is 0, 1, 2, 3, 4, or 5.

Embodiment Q11

The compound of any preceding embodiments Q1 to Q10, where $R_4$ is selected from the group consisting of

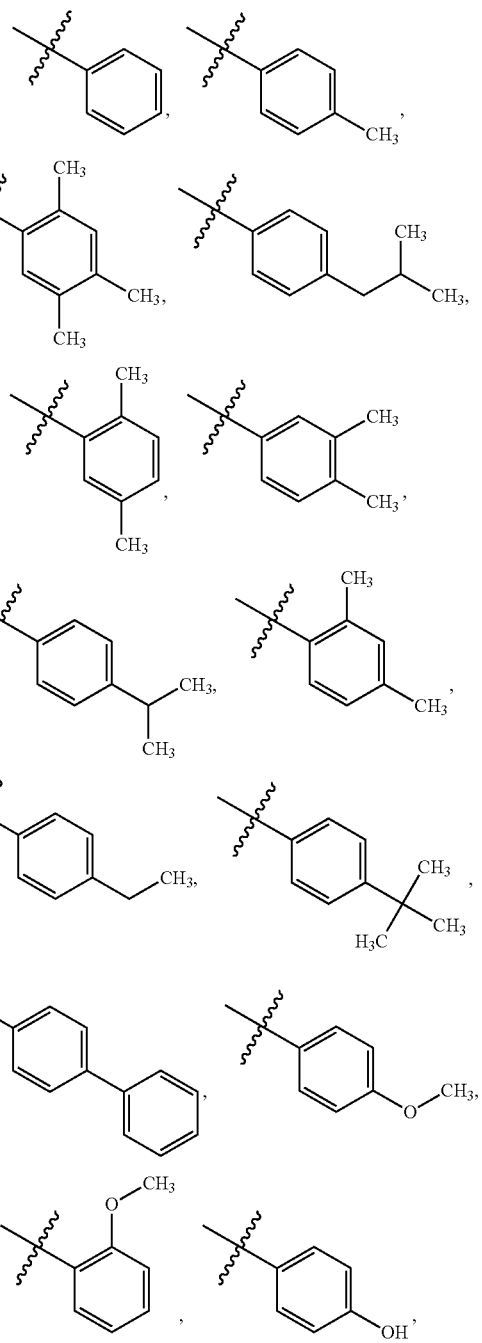

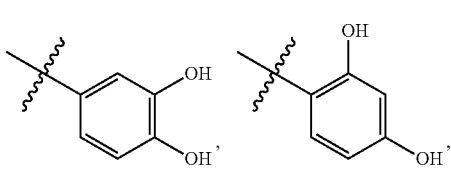

-continued

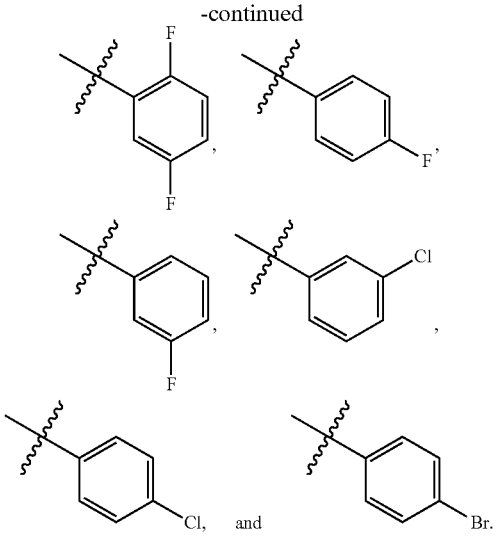

Embodiment Q12

The compound of any preceding embodiments Q1 to Q11, where $R_5$ is selected from the group consisting of H, $(C_1-C_6)$ alkyl.

Embodiment Q13

The compound of any preceding embodiments Q1 to Q12, where m is 1 or 2.

Embodiment Q14

The compound of any preceding embodiments Q1 to Q13, where p is 1 or 2.

Embodiment Q15

The compound of any preceding embodiments Q1 to Q14, where p is 1 or 2 and m is 1 or 2.

Embodiment Q16

The compound of any preceding embodiments Q1 to Q15, where m is 1 and p is 1

Embodiment Q17

A composition including the compound of any preceding embodiments, in the form of a liposomal particle, a nanoparticle, or a PEGylated compound.

Embodiment Q18

A composition including racemic mixtures of enantiomers of the compound of any preceding embodiments.

Embodiment Q19

A composition including the compound of any preceding embodiments, and a physiologically compatible excipient.

Embodiment Q20

The compound of any proceeding embodiments Q1 to Q19, where $R_1$ is selected from the group consisting of 4-methylpyridine, 5-ethyl-2-methylpyridine, and 4-methanesulfonylphenyl.

Embodiment Q21

The compound of any proceeding embodiments Q1 to Q20, where Y is —S—CH(CH$_3$)—C(=O)—R$_3$ and $R_3$ is selected from the group consisting of benzene, 4-ethyl benzene, 3-nitrobenzene, 3-fluorobenzene, 3-aniline, 2-pyridine, and 3-N-phenylmethanesulfonamide.

Embodiment Q22

The compound of any proceeding embodiments Q1 to Q21, where $R_2$ is selected from the group consisting of 4-methyl, and 4-methanesulfonamide.

Embodiment Q23

A compound selected from Table II.

Embodiment Q24

A pharmaceutical composition including a therapeutically effective amount of a compound of any one of the preceding embodiments or a pharmaceutically acceptable salt thereof, and a pharmaceutically acceptable carrier.

Embodiment Q25

The compound of any preceding embodiments, for use in a method of treating cancer.

Embodiment Q26

A method of treating or preventing a disease, where the disease is caused by, or associated with, STING expression, activity, and/or function, or is associated with deregulation of one or more of the intracellular pathways in which a STING protein is involved, including determining from a patient test sample that the patient has the disease and administering a therapeutically effective amount of a compound of any one of the preceding embodiments or a pharmaceutically acceptable salt thereof.

Embodiment Q27

A compound of any one of the preceding embodiments or a pharmaceutically acceptable salt or ester thereof, or the pharmaceutical composition of embodiment Q24, for use in modulating a STING protein, or in treating or preventing a disease caused by, or associated with, STING expression, activity, and/or function, or associated with deregulation of one or more of the intracellular pathways in which a STING protein is involved.

Embodiment Q28

A kit including a compound of any one of the preceding embodiments, or a pharmaceutically acceptable salt or ester thereof, or the pharmaceutical composition of embodiment Q24.

The invention claimed is:

1. A pharmaceutical composition comprising a therapeutically effective amount of a compound for activating the stimulator of interferon genes (STING) and a pharmaceutically acceptable carrier, wherein the compound is N-(1-(3-(4-ethylphenyl)-1,2,4-oxadiazol-5-yl)ethyl)benzenesulfonamide, a pharmaceutically acceptable salt, hydrate, solvate, stereoisomer, or tautomer thereof.

2. The pharmaceutical composition of claim 1, wherein the compound is in the form of a liposomal particle, a nanoparticle, or a PEGylated compound.

3. The pharmaceutical composition of claim 2, wherein the compound is in the form of a liposomal particle.

4. The pharmaceutical composition of claim 2, wherein the compound is in the form of a nanoparticle.

5. The pharmaceutical composition of claim 2, wherein the compound is in the form of a PEGylated compound.

6. The pharmaceutical composition of claim 1, wherein the compound is in a racemic mixture of its enantiomers.

* * * * *